United States Patent
Antzelevitch et al.

(10) Patent No.: US 8,754,087 B2
(45) Date of Patent: Jun. 17, 2014

(54) METHOD OF TREATING ATRIAL FIBRILLATION

(71) Applicant: Gilead Sciences, Inc., Foster City, CA (US)

(72) Inventors: Charles Antzelevitch, New Hartford, NY (US); Luiz Belardinelli, Palo Alto, CA (US); Alexander Burashnikov, New Hartford, NY (US); John Shryock, East Palo Alto, CA (US); Dewan Zeng, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/907,349

(22) Filed: May 31, 2013

(65) Prior Publication Data

US 2013/0317038 A1 Nov. 28, 2013

Related U.S. Application Data

(62) Division of application No. 12/972,949, filed on Dec. 20, 2010, now Pat. No. 8,513,254.

(60) Provisional application No. 61/288,739, filed on Dec. 21, 2009.

(51) Int. Cl.
*A61K 31/497* (2006.01)
*A61K 31/355* (2006.01)

(52) U.S. Cl.
USPC .................................... 514/252.12; 514/469

(58) Field of Classification Search
USPC ........................................ 514/252.12, 469
See application file for complete search history.

(56) References Cited

U.S. PATENT DOCUMENTS

| 4,567,264 A | 1/1986 | Kluge et al. |
| 5,223,510 A | 6/1993 | Gubin et al. |
| 5,955,103 A | 9/1999 | Jao et al. |
| 2002/0042405 A1 | 4/2002 | Schuh et al. |
| 2005/0065208 A1 | 3/2005 | Brandts et al. |
| 2008/0214555 A1 | 9/2008 | Jerling et al. |
| 2009/0247535 A1 | 10/2009 | Pitt |

FOREIGN PATENT DOCUMENTS

| WO | WO 2005/105096 | 10/2005 |
| WO | WO 2009/150535 | 12/2009 |

OTHER PUBLICATIONS

Burashnikov et al., J Am Coll Cardiol., 2010;56:1216-1224.*
Verrier et al., Heart Rhythm, 2013;10:121-127.*
Burashnikov et al., Ann N Y Acad Sci, 2008;1123:105-112.*
Singh et al., The New England Journal of Medicine, 2007;357(10):987-999.*
Antzelevitch et al., "Atrial-selective sodium channel block as a novel strategy for the management of atrial fibrillation", Journal of Electrocardiology, 2009, 42(6): 543-548.

(Continued)

*Primary Examiner* — San-Ming Hui
(74) *Attorney, Agent, or Firm* — Sheppard Mullin Richter & Hampton LLP

(57) ABSTRACT

The present invention relates to a method for the treatment or prevention of atrial fibrillation and/or atrial flutter comprising coadministration of a synergistically therapeutic amount of dronedarone or a pharmaceutically acceptable salt or salts thereof and a synergistically therapeutic amount of ranolazine or a pharmaceutically acceptable salt or salts thereof. Also provided are methods for modulating ventricular and atrial rhythm and rate. This invention also relates to pharmaceutical formulations that are suitable for such combined administration.

24 Claims, 24 Drawing Sheets

(56) References Cited

OTHER PUBLICATIONS

Author Unknown, "Dronedarone: Dronedarone, SR 33589, SR 33589B", Drugs R.D., 2007, 8(3): 171-175.
Burashnikov et al., "Atrial-Selective Sodium Channel Block as a Strategy for Suppression of Atrial Fibrillation", 2008, Ann N Y Acad Sci; 1123: 105-112.
Burashnikov et al., "Atrial-Selective Sodium Channel Block for the Treatment of Atrial Fibrillation", NIH Public Access, 2009, 1-25.
Burashnikov et al., Atrial-Selective Sodium Channel Block for the Treatment of Atrial Fibrillation, Expert Opin. Emerg. Drugs, 2009, 14(2):233-249.
Burashnikov et al., "Synergistic Effect of the Combination of Ranolazine and Dronedarone to Suppress Atrial Fibrillation," Journal of the American College of Cardiology, (2010), 56(15): 1216-1224.
Davy et al., "Dronedarone for the Control of Ventricular Rate in Permanent Atrial Fibrillation: The Efficacy and Safety of Dronedarone for the Control of Ventricular Rate During Atrial Fibrillation (ERATO) Study", American Heart Journal, 2008, 156(3): 527. el-527.e9.
Ehrlich et al., "Atrial-selective pharmacological therapy for atrial fibrillation: hype or hope?" Current Opinion in Cardiology, 2009, 24(1): 50-55.
Gramley et al., "Recent Advances in the Pharmacological Treatment of Cardiac Arrhythmias", Drugs of Today, 2009, 45(11): 807-825.
Hohnloser et al., "Effect of Dronedarone on Cardiovascular Events in Atrial Fibrillation", New England Journal of Medicine, 2009, 360(7): 668-678.
International Search Report for PCT/US2010/061257 dated May 27, 2011, 6 pages (045710-4210).
Kumar et al., "New and Emerging Antiarrhythmic Drugs for Atrial Fibrillation: What May Become Available to the Clinician in the Near Future", Current Treatment Options in Cardiovascular Medicine, 2009, 11(5), 373-380.

Mason et al. "New Pharmacological agents for arrhythmias", Circulation:Arrhythmia and Electrophysiology, 2009, 2: 588-597.
Office Action for U.S. Appl. No. 12/556,417, dated Mar. 21, 2011.
Office Action for U.S. Appl. No. 12/755,931, dated Apr. 27, 2011.
Office Action for U.S. Appl. No. 12/779,753, dated Jun. 16, 2011.
Opposition filed on Dec. 12, 2012 in Colombia Application No. 12-106.347.
Opposition filed Dec. 22, 2011, in Bolivian Application No. SP-00399-2010.
Opposition filed on Nov. 26, 2012 in Peruvian Application No. 852.
Scirica et al., Effect of Ranolazine, an Antianginal Agent with Novel Electrophysical Properties, on the Incidence of Arrhythmias in Patients with Non-ST-Segment-Elevation Acute Coronary Syndrome—Thrombolysis in Myocardial Infarction 36 (MERLIN-TIMI 36) Randomized Controlled Trial, Circulation, 2007, 116(15): 1647-1652.
Sicouri et al., "Antiarrhythmic Effects of Ranolazine in Canine Pulmonary Vein Sleeve Preparations", Heart Rhythm, 2008, 5(7): 1019-1026.
Singh et al., "Dronedarone for Maintenance of Sinus Rhythm in Atrial Fibrillation or Flutter", The New England Journal of Medicine, 2007, 357; 10: 987-999.
Tafreshi et al., "A review of the investigational antiarrhythmic agent dronedarone", Journal of Cardiovascular Pharmacology and Therapeutics, 2007, 12(1): 15-26.
Verrier et al. "Low doses of ranolazine and dronedarone in combination exert potent protection against atrial fibrillation and vulnerability to ventricular arrhythmias during acute myocardial ischemia," Heart Rhythm, (2013), 10: 121-127.

* cited by examiner

METHOD OF TREATING ATRIAL FIBRILLATION

CROSS-REFERENCE TO RELATED APPLICATIONS

This application is a divisional application of U.S. application Ser. No. 12/972,949, filed Dec. 20, 2010, which application claims the benefit under 35 U.S.C. §119(e) of U.S. Provisional Application No. 61/288,739, filed on Dec. 21, 2009, which are hereby incorporated by reference in their entirety.

FIELD OF THE INVENTION

The present invention relates to methods of treating and/or preventing atrial fibrillation and/or atrial flutter by coadministration of therapeutically effective amounts or less of ranolazine or pharmaceutically acceptable salts thereof and dronedarone or pharmaceutically acceptable salts thereof. This invention also relates to pharmaceutical formulations that are suitable for such coadministration.

BACKGROUND

Atrial fibrillation (AF) is the most prevalent arrhythmia, the incidence of which increases with age. It is estimated that 8% of all people over the age of 80 experience this type of abnormal heart rhythm and AF accounts for one-third of hospital admissions for cardiac rhythm disturbances. Over 2.2 million people are believed to have AF in the Unites States alone. Fuster et al *Circulation* 2006 114 (7): e257-354. Although atrial fibrillation is often asymptomatic it may cause palpitations or chest pain. Prolonged atrial fibrillation often results in the development of congestive heart failure and/or stroke. Heart failure develops as the heart attempts to compensate for the reduced cardiac efficiency while stroke may occur when thrombi form in the atria, pass into the blood stream and lodge in the brain. Pulmonary emboli may also develop in this manner.

Current methods for treating AF include electric and/or chemical cardioversion and laser ablation. Anticoagulants, such as warfarin, dabigatran, and heparin, are typically prescribed in order to avoid stroke. While there is currently some debate regarding the choice between rate and rhythm control, see Roy et al. *N Engl J Med* 2008 358:25; 2667-2677, rate control is typically achieved by the use of beta blockers, cardiac glycosides, and calcium channel blockers.

One of the most common anti-arrhythmic agents is amiodarone which is commonly administered for both acute and chronic arrhythmias, including acute and/or chronic AF. Unfortunately, amiodarone is a highly toxic drug and has a wide range of undesirable side effects. The most dangerous of these effects is the development of interstitial lung disease. Thyroid toxicity, both hypothyroidism and hyperthyroidism, is often seen, as are effects in the eye and liver. Additionally, many patients (8-18%) discontinue use of amiodarone after one year due to intolerant side effects.

Dronedarone, a non-iodinated derivative of amiodarone, reduces cardiovascular hospitalization and mortality in patients with atrial fibrillation and/or atrial flutter (AFL), but its anti-AF efficacy in the clinic is inferior to that of amiodarone.[2,3] After several large trials,[4-8] the Unites States Food and Drug Administration (FDA) approved dronedarone (400 mg BID) in July of 2009 for the reduction of risk of cardiovascular hospitalization in patients with paroxysmal or persistent AF or AFL. In the clinical studies, doses of dronedarone 400, 600, or 800 mg twice daily (BID) were studies in patients with AF/AFL. Dronedarone 400 mg BID was associated with significant reduction in the risk of recurrent atrial fibrillation, but doses of dronedarone 600 mg BID and 800 mg BID were not effective and were poorly tolerated. Thus, methods of increasing the anti-arrhythmic efficacy of dronedarone are highly desirable.

It has now been found that the combination of dronedarone and ranolazine has synergism resulting in potent electrophysiologic actions leading to marked suppression of atrial arrhythmias among other cardiac conditions. For example, the combination of dronedarone and ranolazine has synergism in reducing AV nodal conduction and ventricular tachyarrhythmia.

SUMMARY OF THE INVENTION

The invention is based on the surprising and unexpected discovery that coadministration of dronedarone and ranolazine to patients provides ventricular and/or atrial rate and/or rhythm control. The ability to control the rate and the rhythm is useful for treating and preventing atrial fibrillation and/or atrial flutter in patients, as well as a variety of other cardiac conditions, which are described throughout. It is further contemplated that the coadministration is useful when dronedarone is administered in a therapeutically effective dose and ranolazine is administered in a therapeutically effective dose. It is further contemplated that either one or both of dronedarone and ranolazine may be effective if being administered in an amount less than their respective therapeutic doses, such as a synergistically effective amount, due to their synergistic effect.

Accordingly, in one aspect, the invention is directed to a method for treatment and/or prevention of atrial fibrillation and/or atrial flutter in a patient in need thereof. The method comprises coadministration of a synergistically therapeutic amount of dronedarone or pharmaceutically acceptable salt or salts thereof and a synergistically therapeutic amount of ranolazine or pharmaceutically acceptable salt or salts thereof.

In another aspect, the invention is directed to a method for reducing the undesirable side effects of dronedarone or pharmaceutically acceptable salt or salts thereof comprising coadministering a synergistically therapeutic amount of ranolazine or a pharmaceutically acceptable salt or salts thereof.

In another aspect, the invention is directed to a method for reducing the therapeutically effective dose of dronedarone or salt or salts thereof comprising coadministering a synergistically therapeutic amount of ranolazine or salt or salts thereof.

In another aspect, the invention is directed to a method for reducing the prolongation of the QT interval in a patient caused by ranolazine or salt or salts thereof, wherein the method comprises administering to the patient a synergistically therapeutic amount of dronedarone or salt or salts thereof. In another aspect, the invention is directed to a method for reducing the prolongation of the QT interval in a patient caused by dronedarone or salt or salts thereof, wherein the method comprises administering to the patient a synergistically therapeutic amount of ranolazine or salt or salts thereof.

In another aspect, the invention is directed to a method for modulating ventricular and/or atrial rate in a patient in need thereof, said method comprising coadministering to the patient synergistically therapeutic amounts of dronedarone and ranolazine or pharmaceutically acceptable salt or salts thereof.

In another aspect, the invention is directed to a method for modulating ventricular and/or atrial rhythm in a patient in need thereof, said method comprising coadministering to the patient synergistically therapeutic amounts of dronedarone and ranolazine or pharmaceutically acceptable salt or salts thereof.

In another aspect, the invention is directed to a method for providing rhythm and rate control of the ventricles and/or atria in a patient in need thereof, said method comprising coadministering to the patient synergistically therapeutic amounts of dronedarone and ranolazine or pharmaceutically acceptable salt or salts thereof.

In another aspect, the invention is directed to a method for reducing or preventing torsades de pointes ventricular tachycardia in a patient in need thereof, said method comprising coadministering to the patient synergistically therapeutic amounts of dronedarone and ranolazine or pharmaceutically acceptable salt or salts thereof.

In another aspect, the invention is directed to a method of preventing ventricular fibrillation in patients susceptible to ventricular fibrillation, said method comprising coadministering to the patient synergistically therapeutic amounts of dronedarone and ranolazine or pharmaceutically acceptable salt or salts thereof.

In another aspect, the invention is directed to a method for modulating electrical and structural remodeling in a patient in need thereof, said method comprising coadministering to the patient synergistically therapeutic amounts of dronedarone and ranolazine or pharmaceutically acceptable salt or salts thereof.

In another aspect, the invention is directed to a method of treating or preventing supraventricular tachyarrhythmia or ventricular tachyarrhythmia in a patient in need thereof comprising coadministering a synergistically therapeutic amount of dronedarone or pharmaceutically acceptable salt or salts thereof and equal to a synergistically therapeutic amount ranolazine or pharmaceutically salt or salts thereof.

In another aspect, the invention is directed to a method of preventing hospitalization and death in a patient in need thereof comprising coadministering a synergistically therapeutic amount of dronedarone or pharmaceutically acceptable salt or salts thereof and equal to a synergistically therapeutic amount ranolazine or pharmaceutically salt or salts thereof. In some embodiments, the patient suffers from atrial fibrillation and/or atrial flutter.

In another aspect, the invention is directed to a method of preventing stroke and heart failure in a patient in need thereof comprising coadministering a synergistically therapeutic amount of dronedarone or pharmaceutically acceptable salt or salts thereof and equal to a synergistically therapeutic amount ranolazine or pharmaceutically salt or salts thereof.

In another aspect, the invention is directed to a pharmaceutical formulation comprising a synergistically therapeutic amount of dronedarone or pharmaceutically acceptable salt or salts thereof, a synergistically therapeutic amount of ranolazine or pharmaceutically acceptable salt or salts thereof, and a pharmaceutically acceptable carrier.

In another aspect of the invention a method is provided a treatment of atrial fibrillation comprising the coadministration of a synergistic therapeutically effective amount of dronedarone and synergistic therapeutically effective amount of ranolazine. The two agents may be administered separately or together in separate or a combined dosage unit. If administered separately, the ranolazine may be administered before or after administration of the dronedarone but typically the ranolazine will be administered prior to the dronedarone.

In another aspect of the invention is provided a method for reducing the undesirable side effects of dronedarone is presented. The method comprises coadministration of a synergistic therapeutically effective dose of dronedarone and a synergistic therapeutically effective dose of ranolazine. As before, the two agents may be administered separately or together in separate or a combined dosage unit. If administered separately, the ranolazine may be administered before or after administration of the dronedarone but typically the ranolazine will be administered prior to the dronedarone.

BRIEF DESCRIPTION OF THE DRAWINGS

As used throughout the Figures, the term "Ran 5" refers to ranolazine 5 μM (micromolar) and the term "Dron 10" refers to dronedarone 10 μM.

decreased the incidence of AF in the presence of ACh (left panel). In the presence of dronedarone (0.3 μM), a lower and therapeutically-relevant concentration of ranolazine (6-10 μM) decreased the incidence of AF in the presence of ACh. Flec refers to flecamide.

Figure 22:
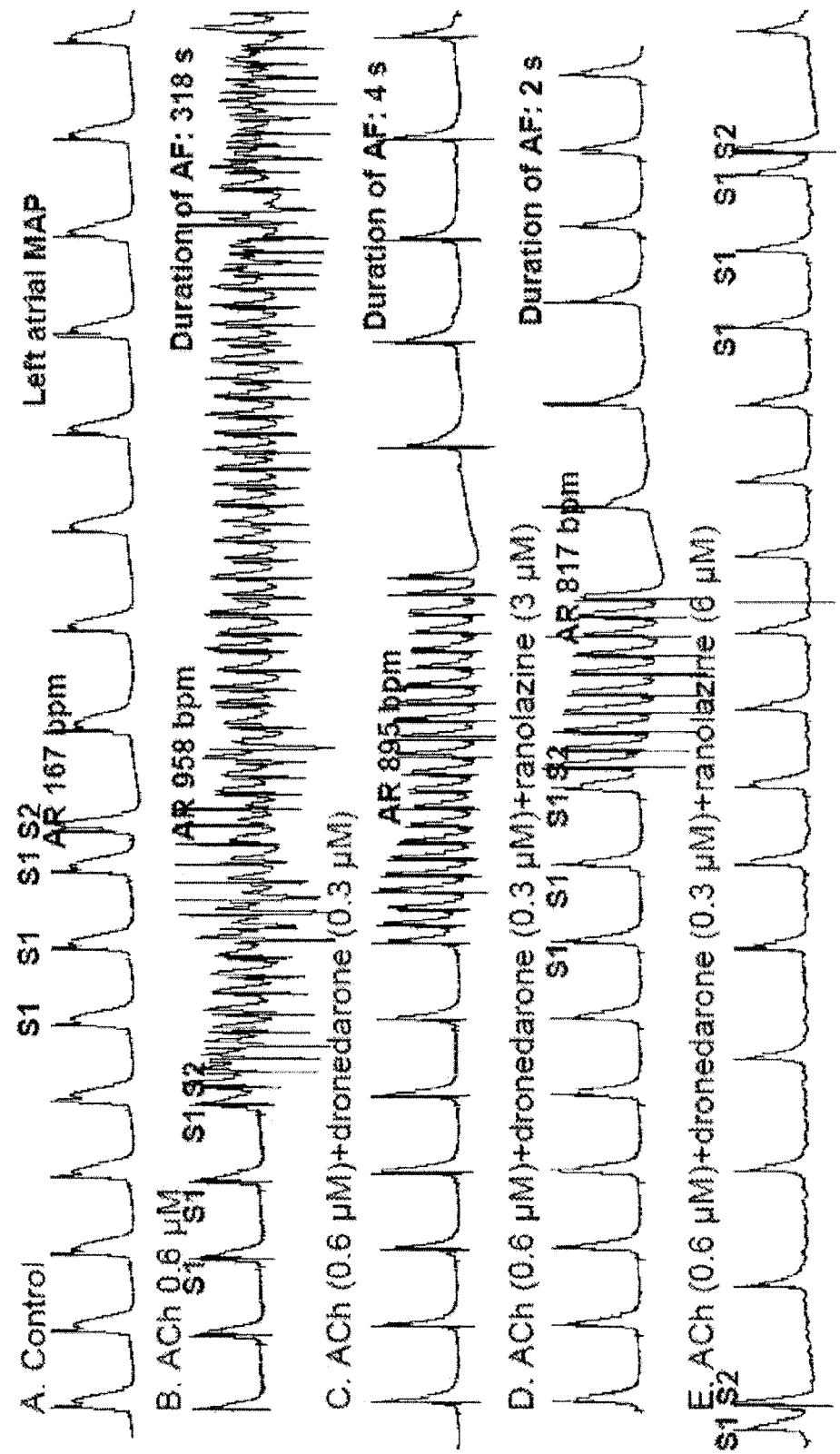

FIG. 22. Dronedarone and ranolazine abolished the premature beat-induced AF (i.e., that caused by S1S2 electrical stimulation) in the presence of acetylcholine (ACh). Representative records of left atrial monophasic action potentials (MAPs) obtained in a heart in the absence of drug (control, A) and in the presence of 0.6 μM ACh (B), 0.6 μM ACh plus 0.3 μM dronedarone (C) and 0.6 μM ACh plus the combination of 0.6 μM dronedarone and 3 or 6 μM ranolazine (D and E, respectively).

Figure 23:
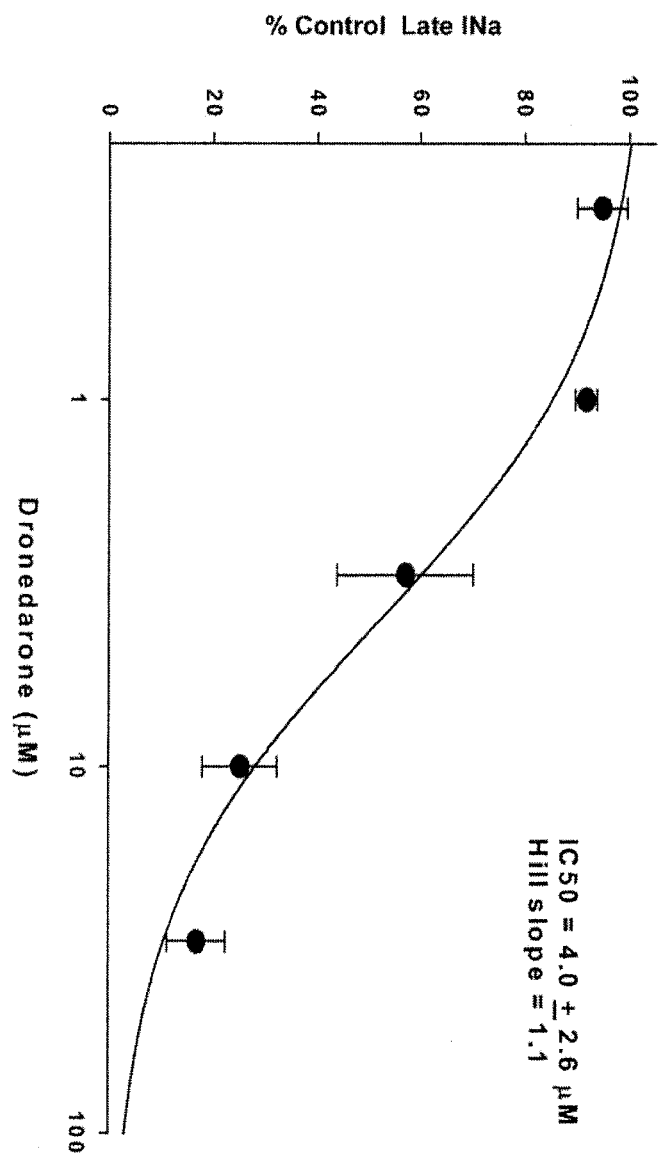

FIG. 23. Dronedarone decreased late $Na^+$ induced by exposure of HEK293 cells expressing $hNa_v1.5$ to the late $Na^+$ enhancer, tefluthrin (10 μM). The concentration of dronedarone causing a half-maximal inhibition of late $Na^+$ was calculated to be 4 μM.

Figure 24:
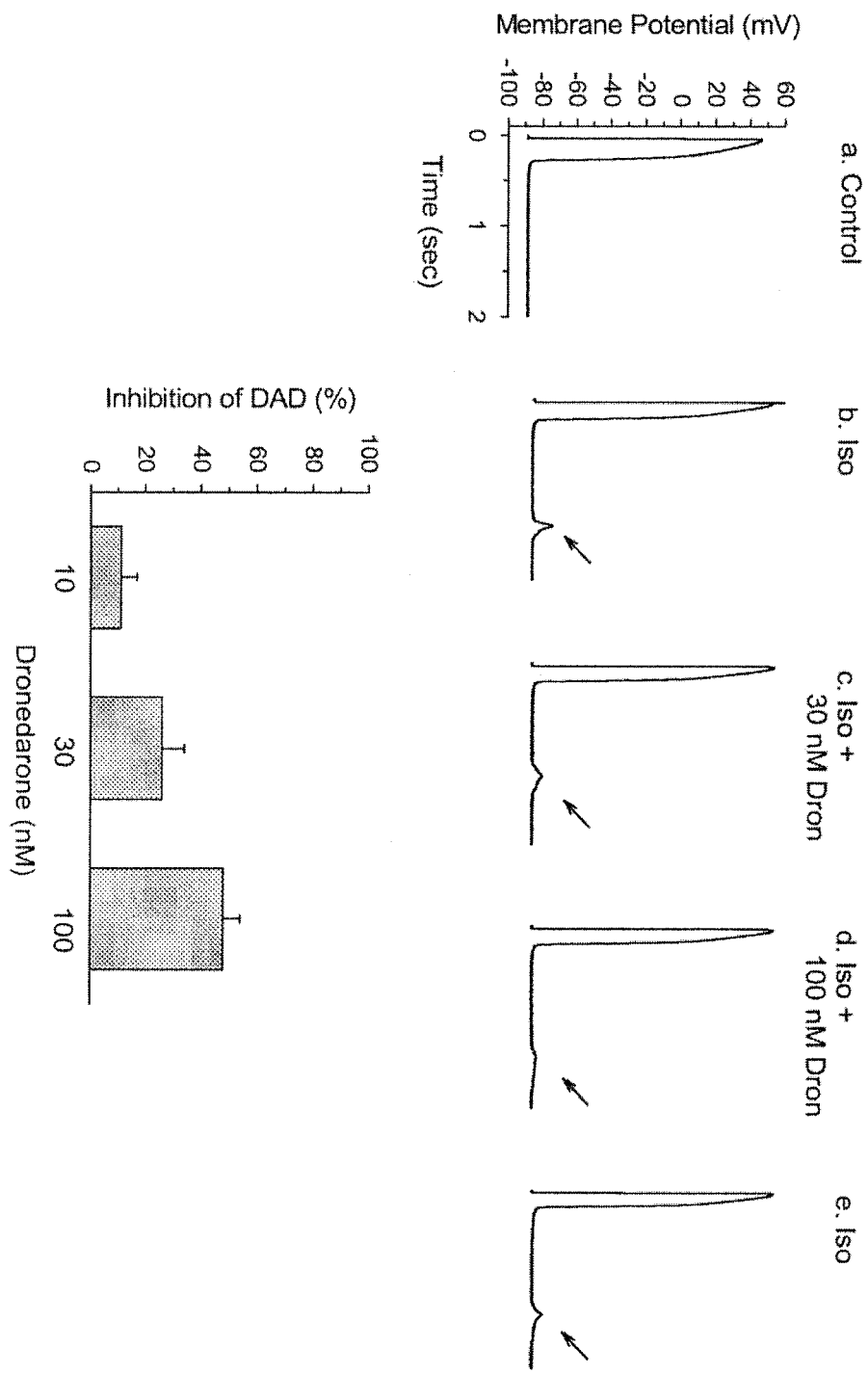

FIG. 24. Dronedarone (Dron, 30 and 100 nM) reduced the amplitude of isoproterenol (Iso, 50 nM)-induced delayed after-depolarizations (DADs) in single myocytes (n=7) isolated from guinea pig left ventricles. Each arrow indicates a DAD; the amplitude of the DAD was calculated electronically. The graph at the bottom represents the percent inhibition of DADs due to varying concentrations of dronedarone (i.e., 10 nM, 30 nM, and 100 nM).

Figure 25:
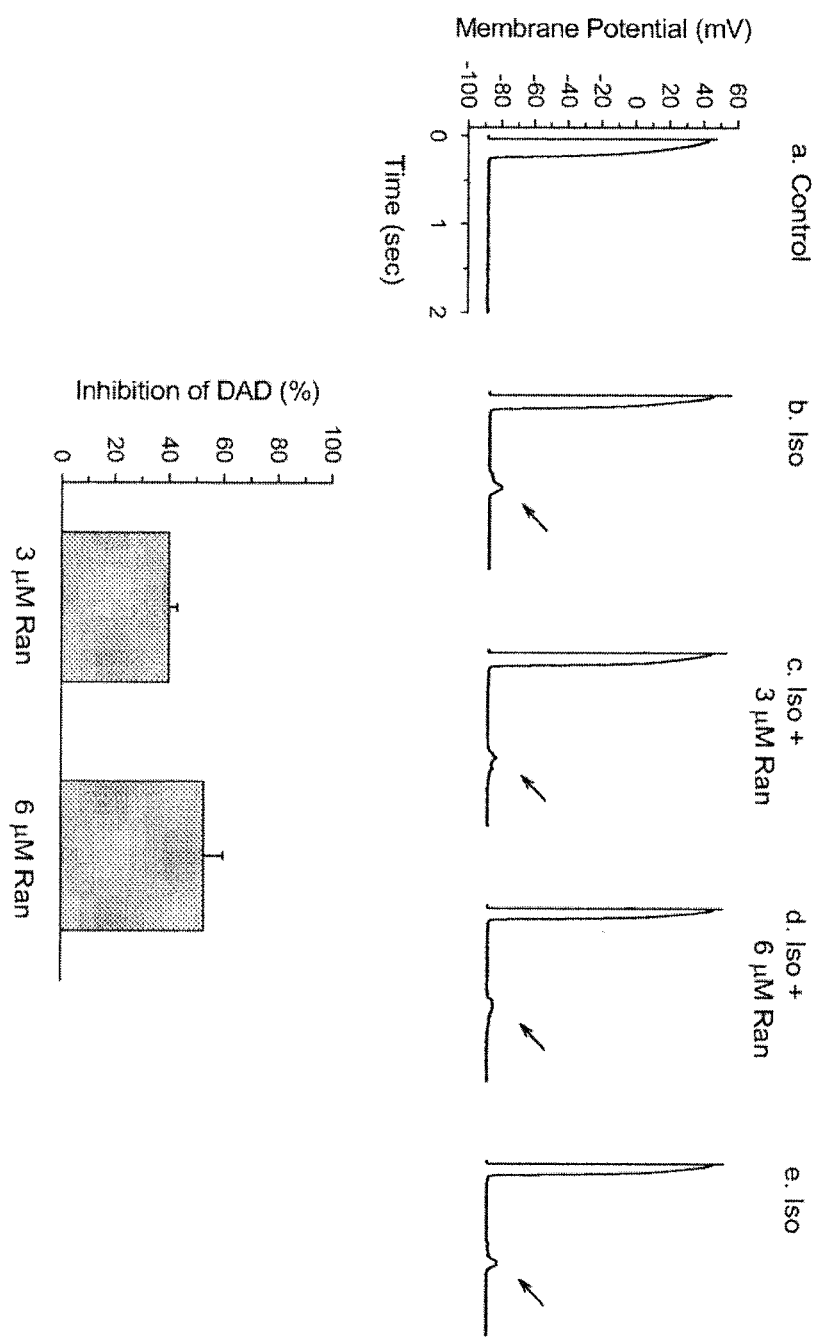

FIG. 25. Ranolazine (Ran, 3 and 6 μM) reduced the amplitude of isoproterenol (Iso, 50 nM)-induced delayed after-depolarizations (DADs) in single myocytes (n=7) isolated from guinea pig left ventricles. Each arrow indicates a DAD; the amplitude of the DAD was calculated electronically. The graph at the bottom represents the percent inhibition of DADs due to varying concentrations of ranolazine (i.e., 3 μM and 6 μM).

Figure 26:
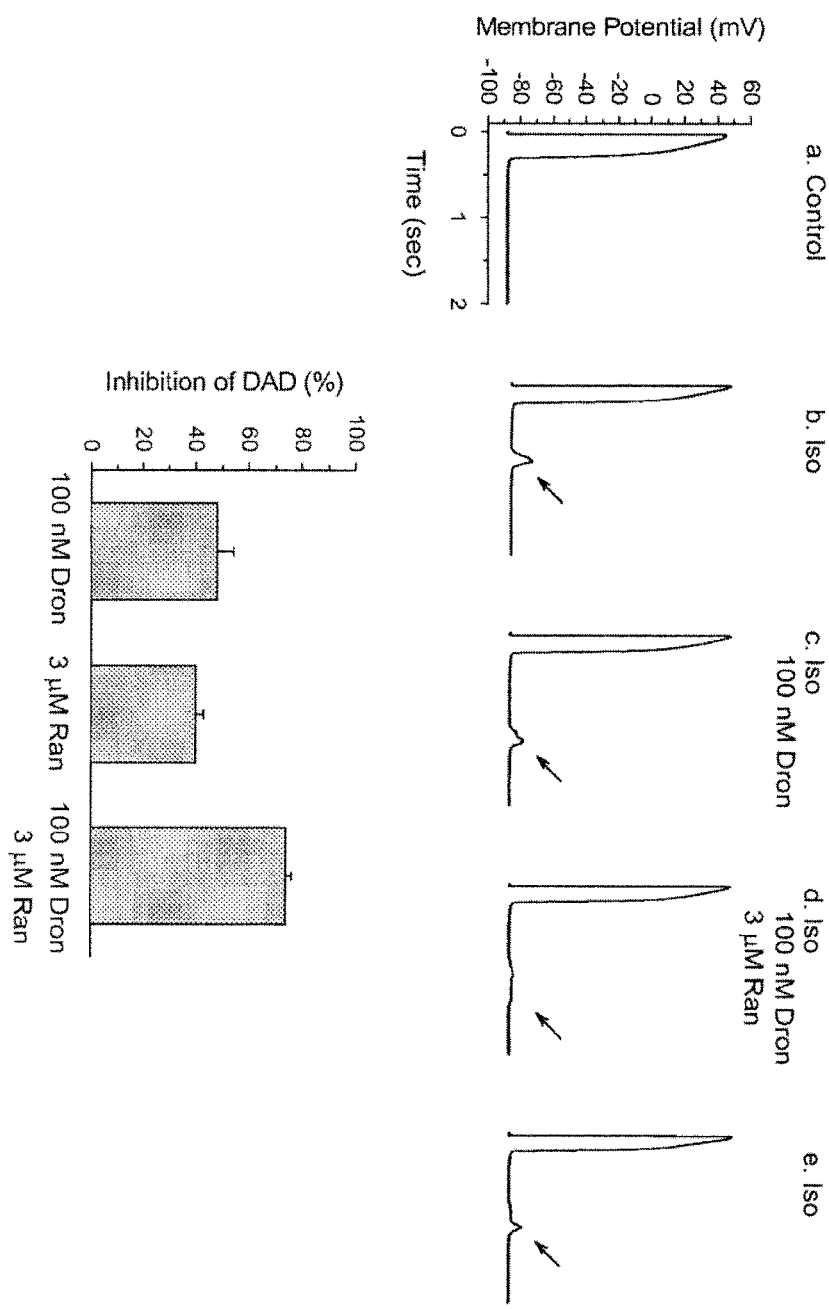

FIG. 26. A combination of dronedarone (100 nM) and ranolazine (3 μM) reduced the amplitude of isoproterenol (Iso, 50 nM)-induced delayed after-depolarizations (DADs) in single myocytes (n=5) isolated from guinea pig left ventricles. The effects of dronedarone and ranolazine were additive. Each arrow indicates a DAD; the amplitude of the DAD was calculated electronically. The graph at the bottom represents the percent inhibition of DADs due to dronedarone (100 nM), ranolazine (3 μM), and dronedarone (100 nM) and ranolazine (3 μM).

DETAILED DESCRIPTION OF THE INVENTION

1. Definitions and General Parameters

As used in the present specification, the following words and phrases are generally intended to have the meanings as set forth below, except to the extent that the context in which they are used indicates otherwise.

It is to be noted that as used herein and in the claims, the singular forms "a," "an" and "the" include plural referents unless the context clearly dictates otherwise. Thus, for example, reference to "a pharmaceutically acceptable carrier" in a composition includes two or more pharmaceutically acceptable carriers, and so forth.

"Comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

"Dronedarone" or "Dron" is described in U.S. Pat. No. 5,223,510. It refers to the chemical compound, N-{2-butyl-3-[4-(3-dibutylaminopropoxy)benzoyl]benzofuran-5-yl} and has the following chemical formula:

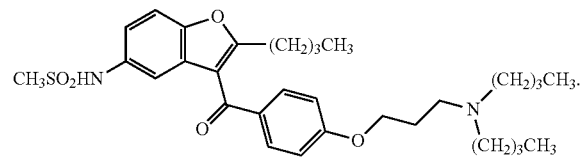

Dronedarone, as used throughout, refers to both the free base or a pharmaceutically acceptable salt. In one embodiment, dronedarone is in its hydrochloride salt form and has the following chemical formula:

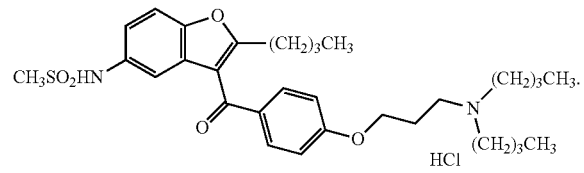

"Ranolazine" or "Ran" is described in U.S. Pat. No. 4,567,264. It refers to the chemical compound (±)-N-(2,6-dimethylphenyl)-4-[2-hydroxy-3-(2-methoxyphenoxy)-propyl]-1-piperazineacetamide, and its pharmaceutically acceptable salts. In its dihydrochloride salt form, ranolazine is represented by the formula:

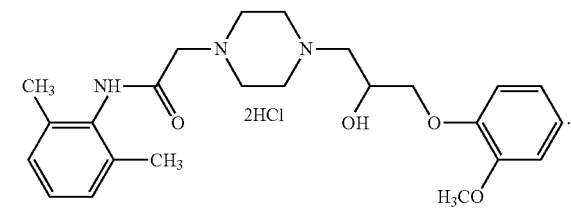 [SMILES: COc1ccccc1OCC(O)CN1CCN(CC(=O)Nc2c(C)cccc2C)CC1]

As used herein, the term "pharmaceutically acceptable salt" refers to a salt of a compound that is derived from a variety of physiologically acceptable organic and inorganic counter ions. Such counter ions are well known in the art and include, by way of example only, sodium, potassium, calcium, magnesium, aluminum, lithium and ammonium, for example tetraalkylammonium, and the like when the molecule contains an acidic functionality; and when the molecule contains a basic functionality, salts of organic or inorganic acids, such as hydrochloride, sulfate, phosphate, diphosphate, nitrate hydrobromide, tartrate, mesylate, acetate, malate, maleate, fumarate, tartrate, succinate, citrate, lactate, pamoate, salicylate, stearate, methanesulfonate, p-toluenesulfonate, and oxalate, and the like. Suitable pharmaceutically acceptable salts also include those listed in Remington's Pharmaceutical Sciences, 17th Edition, pg. 1418 (1985) and P. Heinrich Stahl, Camille G. Wermuth (Eds.), Handbook of Pharmaceutical Salts Properties, Selection, and Use; 2002. Examples of acid addition salts include those formed from acids such as hydroiodic, phosphoric, metaphosphoric, nitric and sulfuric acids, and with organic acids, such as alginic, ascorbic, anthranilic, benzoic, camphorsulfuric, citric, embonic (pamoic), ethanesulfonic, formic, fumaric, furoic, galacturonic, gentisic, gluconic, glucuronic, glutamic, glycolic, isonicotinic, isothionic, lactic, malic, mandelic, methanesulfonic, mucic, pantothenic, phenylacetic, propionic, saccharic, salicylic, stearic, succinic, sulfinilic, trifluoroacetic and arylsulfonic for example benzenesulfonic and p-toluenesulfonic acids. Examples of base addition salts formed with alkali metals and alkaline earth metals and organic bases include chloroprocaine, choline, N,N-dibenzylethylenediamine, diethanolamine, ethylenediamine, lysine, meglumaine (N-methylglucamine), and procaine, as well as internally formed salts. Salts having a non-physiologically acceptable anion or cation are within the scope of the invention as useful intermediates for the preparation of physiologically acceptable salts and/or for use in non-therapeutic, for example, in vitro, situations.

The invention specifically contemplates using salts of both ranolazine and dronedarone and further contemplates mixtures of salts of dronedarone and/or ranolzine.

In certain embodiments, it is contemplated that the ranolazine and/or dronedarone as used herein has not been sufficiently ionized and may be in the form a co-crystal. In one embodiment, the present invention provides a co-crystal composition comprising a co-crystal of ranolazine and/or dronedarone, wherein said co-crystal comprises ranolazine and/or dronedarone and a co-crystal former. The term "co-crystal" refers a crystalline material which comprises ranolazine and/or dronedarone and one or more co-crystal formers, such as a pharmaceutically acceptable salt. In certain embodiments, the co-crystal can have an improved property as compared to the free form (i.e., the free molecule, zwitter ion, hydrate, solvate, etc.) or a salt (which includes salt hydrates and solvates). In further embodiments, the improved property is selected from the group consisting of: increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are well to those of skill in the art.

The term "therapeutically effective amount" refers to that amount of a compound, such as ranolazine or dronedarone, that is sufficient to effect treatment, as defined below, when administered to a mammal in need of such treatment. The therapeutically effective amount will vary depending upon the specific activity of the therapeutic agent being used, the severity of the patient's disease state, and the age, physical condition, existence of other disease states, and nutritional status of the patient. Additionally, other medication the patient may be receiving will effect the determination of the therapeutically effective amount of the therapeutic agent to administer. In some embodiments, the term "therapeutically effective amount" refers to a synergistically effective amount or synergistically therapeutic amount.

"Synergistic" means that the therapeutic effect of dronedarone when administered in combination with ranolazine (or vice-versa) is greater than the predicted additive therapeutic effects of dronedarone and ranolazine when administered alone. The term "synergistically therapeutic amount" typically refers to a less than standard therapeutic amount of one or both drugs, meaning that the amount required for the desired effect is lower than when the drug is used alone. A synergistically therapeutic amount also includes when one drug is given at a standard therapeutic dose and another drug is administered in a less than standard therapeutic dose. For example, ranolazine could be given in a therapeutic dose and dronedarone could be given in a less than standard therapeutic dose to provide a synergistic result.

The term "treatment" or "treating" means any treatment of a disease or condition in a subject, such as a mammal, including: 1) preventing or protecting against the disease or condition, that is, causing the clinical symptoms not to develop; 2) inhibiting the disease or condition, that is, arresting or suppressing the development of clinical symptoms; and/or 3) relieving the disease or condition that is, causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "susceptible" refers to a patient who has had at least one occurrence of the indicated condition.

The term "patient" typically refers to a "mammal" which includes, without limitation, human, monkeys, rabbits, mice, domestic animals, such as dogs and cats, farm animals, such as cows, horses, or pigs, and laboratory animals.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Atrial fibrillation" or "AF" occurs when the heart's two upper chambers (the right and left atria) quiver instead of beating and contracting rhythmically. Electrocardiographically, AF is characterized by a highly disorganized atrial electrical activity that often results in fast beating of the heart's two lower chambers (the right and left ventricles). Symptoms experienced by patients with AF include palpitation, fatigue, and dyspnea (shortness of breath).

There are three types of AF based on the presentation and duration of the arrhythmia: a) Paroxysmal AF: recurrent AF (>2 episodes) that starts and terminates spontaneously within 7 days (paroxysmal AF starts and stops spontaneously); b) Persistent AF: sustained AF that lasts longer than 7 days or requires termination by pharmacologic or electrical cardioversion (electrical shock); and c) Permanent AF: long standing AF (for >1 year duration) in which normal sinus rhythm cannot be maintained even after treatment, or when the patient and physician have decided to allow AF to continue without further efforts to restore sinus rhythm.

"Atrial flutter" is an abnormal heart rhythm that occurs in the atria of the heart. When it first occurs, it is usually associated with a fast heart rate or tachycardia (230-380 beats per minute (bpm)), and falls into the category of supra-ventricular tachycardias. While this rhythm occurs most often in individuals with cardiovascular disease (e.g. hypertension, coronary artery disease, and cardiomyopathy), it may occur spontaneously in people with otherwise normal hearts. It is typically not a stable rhythm, and frequently degenerates into atrial fibrillation (AF).

Both "electrical and structural remodeling" contribute to the pathogenesis of AF. Electrical triggers (after potentials) and arrhythmogenic substrate (re-entry) are two main causes for the initiation and maintenance of AF. "Electrical remodeling" is caused by malfunctioning of ion channels (mainly sodium, calcium, and potassium channels). "Structural remodeling" is caused by proliferation and differentiation of fibroblasts into myofibroblasts and enhanced connective tissue deposition. Structural remodeling results in the electrical dissociation between cardiac muscle bundles and heterogeneity in the electrical conduction in the atrium. Thus, inflammation and/or fibrosis of atrial tissue create a milieu conducive for AF. The electrical and structural remodeling of the atria leads to the perpetuation of AF. Hence, "AF begets AF". Prolonged episodes of AF frequently cause mechanical dysfunction of the atrium resulting in adverse hemodynamic consequences and may contribute to heart failure.

"Ventricular fibrillation" occurs when the heart beats with rapid, erratic electrical impulses which causes pumping chambers in the heart (i.e. the ventricles) to quiver uselessly, rather than pump blood. Ventricular fibrillation requires immediate medical attention as blood pressure plummets, cutting off blood supply to vital organs. A person with ventricular fibrillation will collapse within seconds and soon will not be breathing or have a pulse. Symptoms include chest pain, rapid heartbeat (tachycardia), dizziness, nausea, shortness of breath, and loss of consciousness or fainting. It is not always known what causes ventricular fibrillation, but most cases of ventricular fibrillation begin as a rapid heartbeat called "ventricular tachycardia" or "VT".

"Torsades de pointes (or TdP) ventricular tachycardia" refers to a specific variety of ventricular tachycardia that exhibits distinct characteristics on the electrocardiogram (ECG). The ECG reading in torsades demonstrates a rapid, polymorphic ventricular tachycardia with a characteristic twist of the QRS complex around the isoelectric baseline. It is also associated with a fall in arterial blood pressure, which can produce fainting. Although "torsades de pointes" is a rare ventricular arrhythmia, it can degenerate into "ventricular fibrillation", which will lead to sudden death in the absence of medical intervention. Torsades de pointes is associated with long QT syndrome, a condition whereby prolonged QT intervals are visible on the ECG. Long QT intervals predispose the patient to an R-on-T phenomenon, where the R wave representing ventricular depolarization occurs simultaneously to the relative refractory period at the end of repolarization (represented by the latter half of the T-wave). An R-on-T can initiate torsades. Long QT syndrome can either be inherited as congenital mutations of ion channels carrying the cardiac impulse/action potential or acquired as a result of drugs that block these cardiac ion currents.

Common causes for torsades de pointes include diarrhea, hypomagnesemia, and hypokalemia. It is commonly seen in malnourished individuals and chronic alcoholics. Drug interactions such as erythromycin or moxifloxacin, taken concomitantly with inhibitors like nitroimidazole, dietary supplements, and various medications like methadone, lithium, tricyclic antidepressants or phenothiazines may also contribute. It can also be the side effect of some anti-arrhythmic medications such as sotalol, procainamide, and quinidine. Factors that are associated with an increased tendency toward torsades de pointes include: class IA antiarrhythmics, class III antiarrhythmics, hypomagnesemia, hypokalemia, hypocalcemia, hypoxia, acidosis, heart failure, left ventricular hypertrophy, slow heart rate, female gender, hypothermia, subarachnoid hemorrhage.

"AV conduction" or "atrioventricular conduction" is the forward conduction of the cardiac impulse from the atria to ventricles via the "atrioventricular node" or "AV node", represented in an electrocardiogram by the P-R interval. The AV node is a part of electrical control system of the heart that electrically connects atrial and ventricular chambers and coordinates heart rate. The AV node is an area of specialized tissue between the atria and the ventricles of the heart, specifically in the posteroinferior region of the interatrial septum near the opening of the coronary sinus, which conducts the normal electrical impulse from the atria to the ventricles. "AV conduction" during normal cardiac rhythm occurs through two different pathways: the first has a slow conduction velocity but shorter refractory period, whereas the second has a faster conduction velocity but longer refractory period.

The term "modulate" means to increase or decrease or otherwise provide control.

"Modulating ventricular and/or atrial rate" has been shown to significantly improve AF. Typically, this has been accomplished with the use of a pacemaker, where the pacemaker detects the atrial beat and after a normal delay (0.1-0.2 seconds) triggers a ventricular beat, unless it has already happened—this can be achieved with a single pacing lead with electrodes in the right atrium (to sense) and ventricle (to sense and pace). The "atrial rate" is specific to the rate (measured in beats per unit time) of only the atrial beat. Pacemakers can also monitor and modulate the ventricular and/or atrial rhythm. The "ventricular and/or atrial rhythm" refers to the beat-to-beat time period of either the ventricular beat or the atrial beat.

"Coadministering" or "coadministration" refers to the administration of two or more therapeutic agents together at one time. The two or more therapeutic agents can be coformulated into a single dosage form or "combined dosage unit", or formulated separately and subsequently combined into a combined dosage unit, typically for intravenous administration or oral administration.

"Intravenous administration" is the administration of substances directly into a vein, or "intravenously". Compared with other routes of administration, the intravenous (IV) route is the fastest way to deliver fluids and medications throughout the body. An infusion pump can allow precise control over the flow rate and total amount delivered, but in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used, which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, a "flush", following the injection to push the medicine into the bloodstream more quickly.

"Oral administration" is a route of administration where a substance is taken through the mouth, and includes buccal, sublabial and sublingual administration, as well as enteral administration and that through the respiratory tract, unless made through e.g. tubing so the medication is not in direct contact with any of the oral mucosa. Typical form for the oral administration of therapeutic agents includes the use of tablets or capsules.

A "sustained release formulation" is a formulation which is designed to slowly release a therapeutic agent in the body over an extended period of time, whereas an "immediate release formulation" is an formulation which is designed to quickly release a therapeutic agent in the body over a shortened period of time. In some cases the immediate release formulation may be coated such that the therapeutic agent is only released once it reached the desired target in the body (e.g. the stomach).

Some of the more common "undesirable side effects of dronedarone" include diarrhea, lack or loss of strength, abdominal or stomach pain, acid or sour stomach, belching, blistering, crusting, irritation, itching, or reddening of the skin, cracked, dry, or scaly skin, heartburn, indigestion, itching skin, nausea, rash, redness or discoloration of the skin, skin rash, encrusted, scaly, and oozing, skin rash, hives, itching, or redness, stomach discomfort, upset, or pain, swelling, and vomiting. Some of the less common or rare side effects include chest pain or discomfort, lightheadedness, dizziness, or fainting, shortness of breath, slow or irregular heartbeat, unusual tiredness, change in taste, increased sensitivity of the skin to sunlight, loss of taste and severe sunburn.

2. Methods

Generally, the present invention relates to methods of treating or preventing atrial fibrillation and/or atrial flutter. The method comprises coadministration of a synergistically therapeutic amount of dronedarone or a pharmaceutically acceptable salt or salts thereof and a synergistically therapeutic amount of ranolazine or a pharmaceutically acceptable salt or salts thereof. In one embodiment, either one or both of ranolazine or dronedarone are administered in a synergistically effective amount. The two agents may be administered separately or together in separate or a combined dosage unit. If administered separately, the ranolazine may be administered before or after administration of the dronedarone but typically the ranolazine will be administered prior to the dronedarone.

As further discussed in the Examples, presented herewith is evidence of a potent effect of the combination of ranolazine and dronedarone to eliminate both the trigger and the substrate associated with the initiation and maintenance of AF. As also shown the Examples, the combination therapy described herein is useful in preventing atrial fibrillation or flutter in patients who are susceptible to the condition.

Ranolazine is an anti-ischemic and antianginal agent that has been shown in preclinical and clinical studies to inhibit the late sodium current ($I_{Na}$) and improve diastolic relaxation. In preclinical studies, ranolazine has also been shown to prevent cellular calcium overload and reduce cardiac electrical and mechanical dysfunction during ischemia.

Results of several recent studies have demonstrated that ranolazine reduces atrial arrhythmic activity. See Burashnikov et al. 2007; 116: 1449-1457; Song et al. *Am J Physiol* 2008; 294: H2031-2039; Sicouri et al. *Heart Rhythm* 2008; 5: 1019-1026. Ranolazine was reported to cause greater inhibition of sodium channels in atrial than in ventricular tissue (Burashnikov et al. 2007; 116: 1449-1457). Ranolazine at clinically relevant concentrations of 5 and 10 µM prolonged the duration of the action potential ($APD_{90}$, duration of the action potential at 90% of repolarization) in atria but had minimal or no effect on APD in ventricular myocardium (Burashnikov et al. 2007; 116: 1449-1457). Ranolazine (5 and 10 µM) caused significant use-dependent (i.e., the effect of ranolazine was greater at higher rates of pacing) depression of the maximum rate of rise of the action potential upstroke ($V_{max}$) and conduction velocity in atrial myocardium and pulmonary vein sleeves but not in ventricular myocardium (Antzelevitch et al. *Circulation* 2004; 110: 904-910, Burashnikov et al. *Circulation* 2007; 116: 1449-1457, and Sicouri et al. *Heart Rhythm* 2008; 5:1019-1026). Ranolazine increased the effective refractory period, induced post-repolarization refractoriness, and caused a loss of excitability of the tissue at higher pacing rates in atrial tissue (Antzelevitch et al. *Circulation* 2004; 110: 904-910, Burashnikov et al. *Circulation* 2007; 116:1449-1457, Sicouri et al. *Heart Rhythm* 2008; 5:1019-1026) and Kurriar et al. *J Cardiovasc Electrophysiol* 2009; 20:796-802.

These data suggest that ranolazine would be effective to terminate and to reduce both the initiation and continuation of atrial tachycardia and fibrillation, and indeed ranolazine significantly depressed atrial excitability and both prevented and terminated acetylcholine-induced fibrillation in atrial myocardium and in canine pulmonary vein sleeves and porcine hearts. Burashnikov et al. 2007; 116: 1449-1457, Sicouri et al. *Heart Rhythm* 2008; 5: 1019-1026, and Kumar et al. *J Cardiovasc Electrophysiol* 2009; 20:796-802 Ranolazine also abolished late $I_{Na}$-induced delayed afterdepolarizations and triggered activity of isolated atrial myocytes (Song et al. *Am J Physiol* 2008; 294: H2031-2039) and decreased diastolic depolarization and initiation of arrhythmic activity. Song et al. *Am J Physiol* 2009.

Ranolazine appears to reduce both the triggers (delayed afterdepolarizations, excitability, and triggered activity) and the electrical substrate (atrial tissue that can support rapid conduction and a high rate of electrical activity) that initiate and support atrial tachycardia and fibrillation Inhibition by ranolazine of specific ion channel currents (peak $I_{Na}$, $I_{Kr}$, and late $I_{Na}$) in atrial tissue is responsible for these anti-arrhythmic effects. First, atrial-selective reduction of peak $I_{Na}$ by ranolazine reduces electrical impulse conduction (conduction velocity) and excitability. Second, inhibition by ranolazine of the delayed rectifier current $I_{Kr}$ further slows the already slow terminal phase of repolarization of the atrial action potential and thereby reduces the availability of Na$^+$ channels for activation of a subsequent action potential upstroke.

These effects contribute to a lengthening of the atrial effective refractory period and result in the induction of post-repolarization refractoriness of the tissue. Tissue that is refractory to electrical stimulation cannot support either the re-entry of electrical activity or high rates of stimulation such as those that occur during atrial tachycardia and fibrillation. Thus the effect of ranolazine to cause a rate-dependent increase of atrial refractoriness reduces the excitable substrate capable of supporting atrial fibrillation.

Finally, the reduction by ranolazine of late $I_{Na}$ may contribute to reduction of cellular calcium loading and suppression of triggered activity in atria, particularly in the conditions of prolonged atrial repolarization, thus preventing the initiation of AF (Sicouri et al. *Heart Rhythm* 2008; 5:1019-1026; Song et al. 2008). Prolonged atrial APD may occur in a number of diseases associated with AF occurrence, such as the congestive heart failure (Li et al. *Circulation* 2000; 101: 2631-2638), atrial dilatation (Verheule at al. *Circulation* 2003; 107:2615-2622), hypertension (Kistler et al. *Eur Heart J* 2006; 27:3045-3056), and long QT syndrome (Kirchhof et al. *J Cardiovasc. Electrophysiol* 2003; 14:1027-1033).

However, AF is commonly associated with abbreviation of atrial repolarization. The integral of sodium ion influx is much smaller through late $I_{Na}$ versus early $I_{Na}$ under normal conditions. With abbreviation of APD, this difference is expected to increase. As a consequence, specific inhibition of late $I_{Na}$ may not significantly affect intracellular sodium concentration (compared to inhibition of early $I_{Na}$). Although ranolazine is a potent late $I_{Na}$ blocker in the ventricle (Antzelevitch et al. *Circulation* 2004; 110: 904-910), its anti-AF actions in the canine right atria and pulmonary vein preparations are attributed primarily to its inhibition of early $I_{Na}$ (Burashnikov et al. *Circulation* 2007; 116:1449-1457 and Sicouri et al. *Heart Rhythm* 2008; 5: 1019-1026). In summary, strong evidence from preclinical studies suggests that ranolazine may be effective in suppressing atrial fibrillation in humans.

As mentioned above, dronedarone is the first anti-arrhythmic drug shown to reduce cardiovascular hospitalization and death. Dronedarone has modest efficacy in maintaining sinus rhythm. As illustrated in the examples, there is a significant synergy between the anti-arrhythmic effects of ranolazine and dronedarone—the combination of ranolazine and dronedarone has significantly greater effects than either drug alone. For example, in canine perfused right atrial preparations, ranolazine alone or dronedarone alone reduced persistent AF by 29% or 17%, respectively, whereas the combination of the two drugs was found to suppress persistent AF by 90%. These and other data presented herewith indicate that the combination of ranolazine and dronedarone has the potential to be more efficacious than either drug alone to reduce the incidence and duration of AF. This combination therapy incorporates both rhythm and rate control.

Accordingly, in one embodiment, the invention is directed to a method for modulating ventricular and/or atrial rate in a patient in need thereof, said method comprising coadministering to the patient synergistically therapeutic amounts of dronedarone and ranolazine or pharmaceutically acceptable salt or salts thereof. In one embodiment, the AV conduction is slowed when atrial rate is high, such sa for example above 400 beats per minute or 600 beats per minute. It is contemplated that this may be beneficial to provide control of the ventricular rate during atrial fibrillation (see Example, Part 2 and FIG. 13A). In another embodiment, the atrial rate is decreased. This confirms the effect of the drug combination to provide control of the ventricular rate when the atrial rate is increased, as during AF (see Example, Part 2 and FIG. 13B). In still another embodiment, the heart rate is not significantly decreased during sinus rhythm.

In another embodiment, is provided a method for modulating ventricular and/or atrial rhythm in a patient in need thereof, said method comprising coadministering to the patient synergistically therapeutic amounts of dronedarone and ranolazine or pharmaceutically acceptable salt or salts thereof. In one embodiment, the sinus rhythm of the patient is maintained.

In still another embodiment, is provided a method for providing rhythm and rate control of the ventricles and/or atria in a patient in need thereof, said method comprising coadministering to the patient synergistically therapeutic amounts of dronedarone and ranolazine or pharmaceutically acceptable salt or salts thereof.

As shown in the example, the induction of torsades de points ventricular tachycardia is reduced by the combination therapy (see Example, Part 2 and FIGS. 17-20). Therefore, in one embodiment, the invention is directed to a method for reducing or preventing torsades de pointes ventricular tachycardia in a patient in need thereof, said method comprising coadministering to the patient synergistically therapeutic amounts of dronedarone and ranolazine or pharmaceutically acceptable salt or salts thereof.

It is contemplated that by preventing atrial fibrillation, both electrical and structural remodeling are modulated. This is because atrial fibrillation begets further atrial fibrillation, and fibrillation begets structural remodeling. The control provided by ranolazine and dronedarone of atrial rhythm (i.e., rhythm control) will prevent the progression of atrial tachyarrhythmias from occasional self-terminated episodes to permanent AF with electrical and structural remodeling. Further, reduction of atrial rate and Na/Ca loading is expected to reduce oxidative stress and decrease cell death, reduce inflammation, and limit fibrosis (Van Wagoner D., *J Cardiovasc Pharm* 52: 306-313, 2008). Accordingly, the invention is also directed to a method for modulating electrical and structural remodeling in a patient in need thereof, said method comprising coadministering to the patient synergistically therapeutic amounts of dronedarone and ranolazine or pharmaceutically acceptable salt or salts thereof.

It is also contemplated that by combining ranolazine and dronedarone any undesired side effects may be reduced. For example, coadministration of ranolazine to a patient already receiving dronedarone therapy reduces the side effects of dronedarone. The synergistic effect of combined administration will allow for a reduction in amount of dronedarone necessary to achieve a therapeutic effect, thereby resulting in a reduced incidence of undesirable side effects. As such, in one embodiment, the invention is directed to a method for reducing the undesirable side effects of dronedarone or pharmaceutically acceptable salt or salts thereof comprising coadministering a synergistically therapeutic amount of ranolazine or a pharmaceutically acceptable salt or salts thereof.

Figure 15:
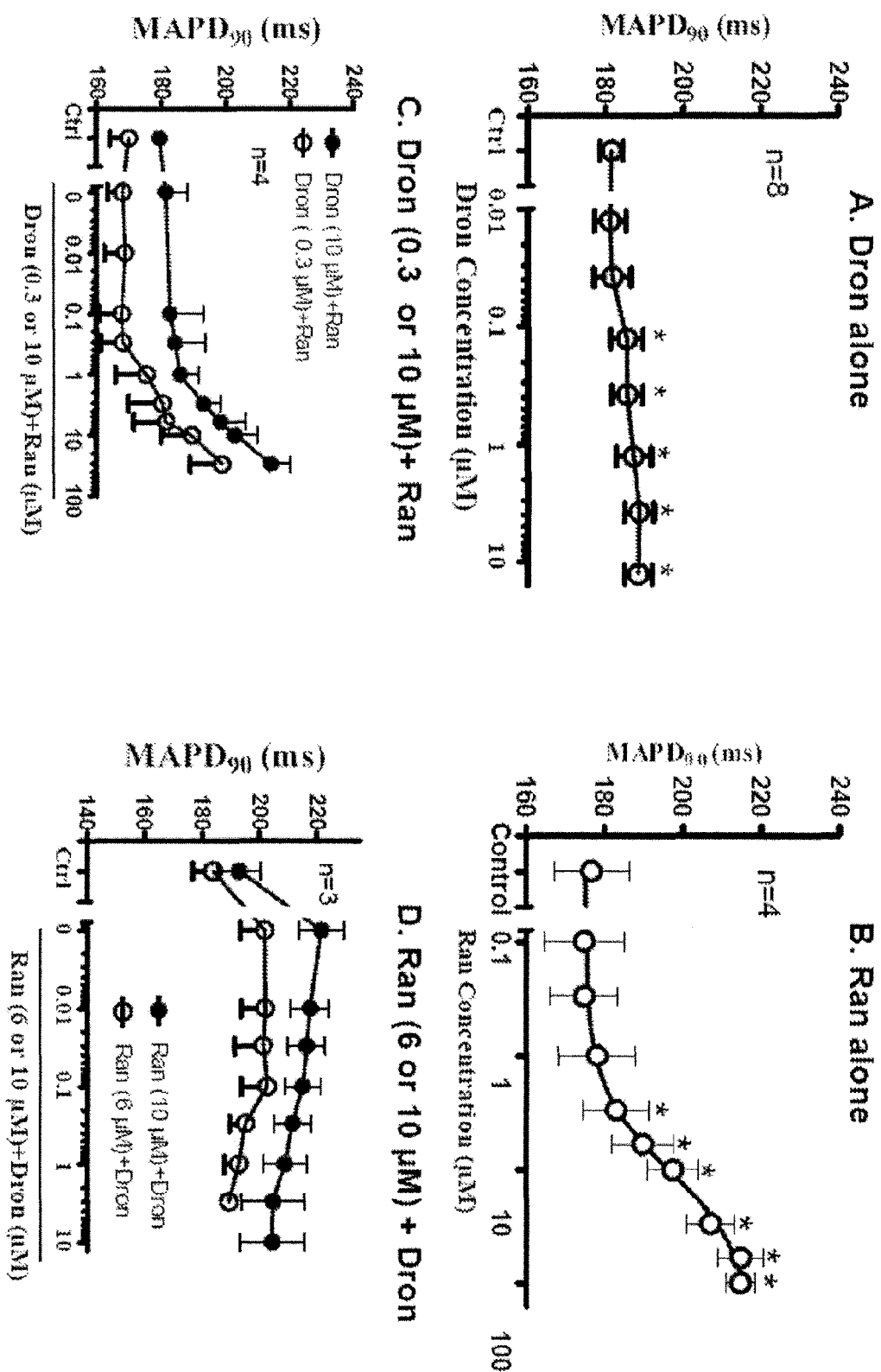
FIG. 15. Concentration-response relationships for Dron (A, n=8), Ran (B, n=4) and either Ran in presence of Dron (0.3 and 10 μM, C) or Dron in presence of Ran (6 and 10 μM, D). *, significantly different from either control (Dron or Ran alone), or Dron alone (C) or Ran alone (D), p<0.05.
Figure 16:
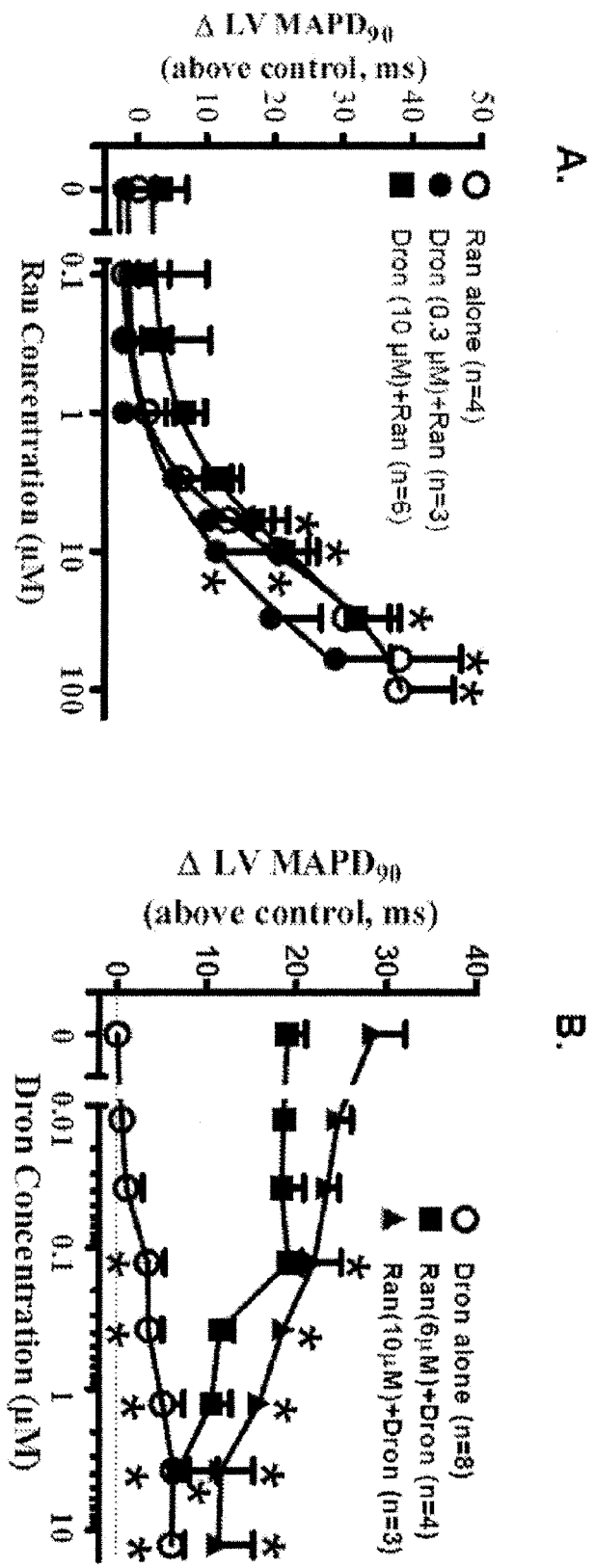
FIG. 16. Effects of ranolazine and dronedarone, alone and in combination, on ventricular action potential duration (MAPD$_{90}$) in female rabbit isolated heart (re-plot of data shown in FIG. 3). Panel A: ranolazine caused a similar relative increase in MAPD$_{90}$ in the absence and presence of dronedarone (0.3 and 10 μM). Panel B: dronedarone attenuated the increase in MAPD$_{90}$ caused by ranolazine (6 and 10 μM). LV refers to left ventricular.
Figure 17:
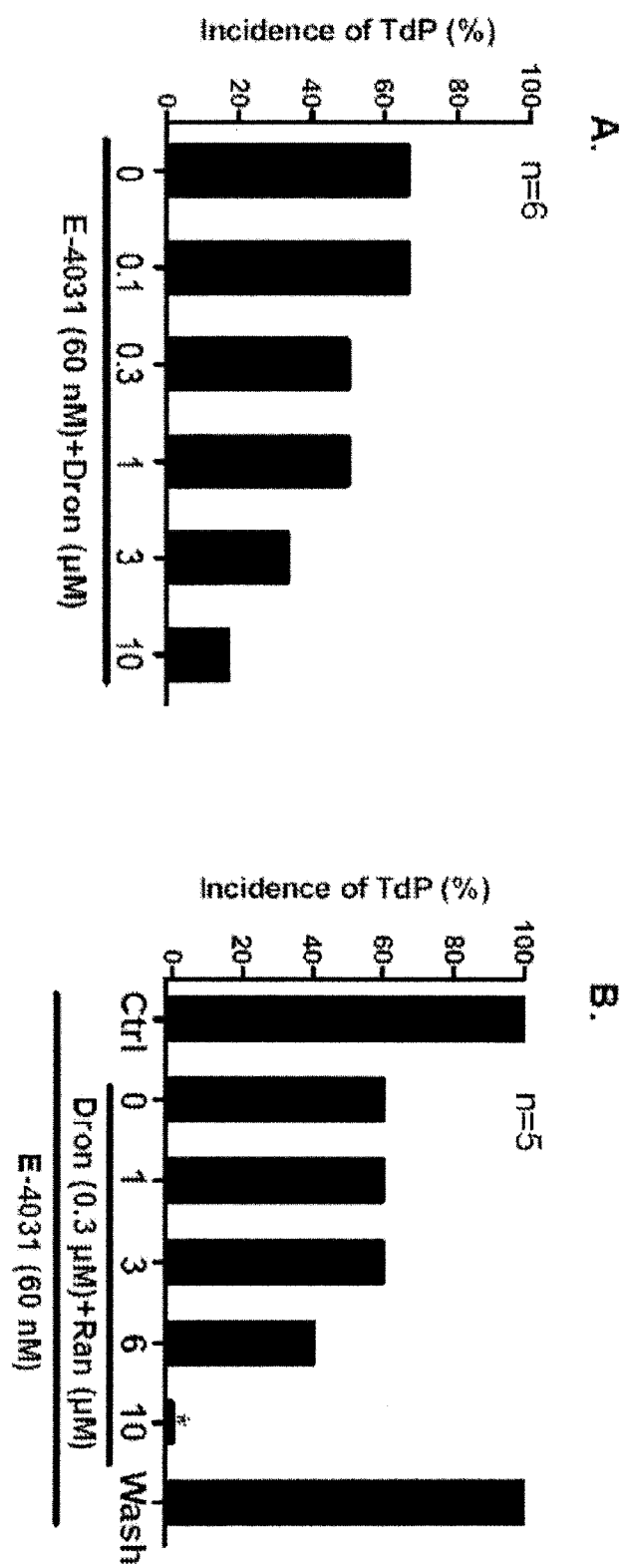
FIG. 17. Dronedarone at a high concentration of 10 μM decreased occurrences of torsades de pointes (TdP) caused by E-4031, an $I_{Kr}$ inhibitor, from 4/6 to 1/6 hearts. Ranolazine (10 μM) together with 0.3 μM dronedarone decreased the incidence of TdP in the presence of 60 nM of E-4031. Ctrl refers to control and Wash refers to washout.

Additionally, it is contemplated that by coadministration of dronedarone to a patient on ranolazine reduces the prolongation of the QT interval, which is sometimes seen in patients on ranolazine therapy (see Example, Part 2 and FIGS. 15D and 16B). Accordingly, in one embodiment, the invention is directed to a method for reducing the prolongation of the QT interval in a patient caused by ranolazine or salt or salts thereof, said method comprising administering to the patient a synergistically therapeutic amount of dronedarone or salt or salts thereof. In the reciprocal, dronedarone may also cause prolongation of the QT interval and as such, by administering dronedarone with ranolazine, it is contemplated a reduction of the QT interval will be seen.

As discussed above, it is contemplated that by administration of ranolazine, the therapeutically effective amount of dronedarone is reduced. As such, the invention, in one embodiment, is directed to a method for reducing the therapeutically effective dose of dronedarone or salt or salts thereof comprising coadministering of a synergistically therapeutic amount of ranolazine or salt or salts thereof.

Figure 5:
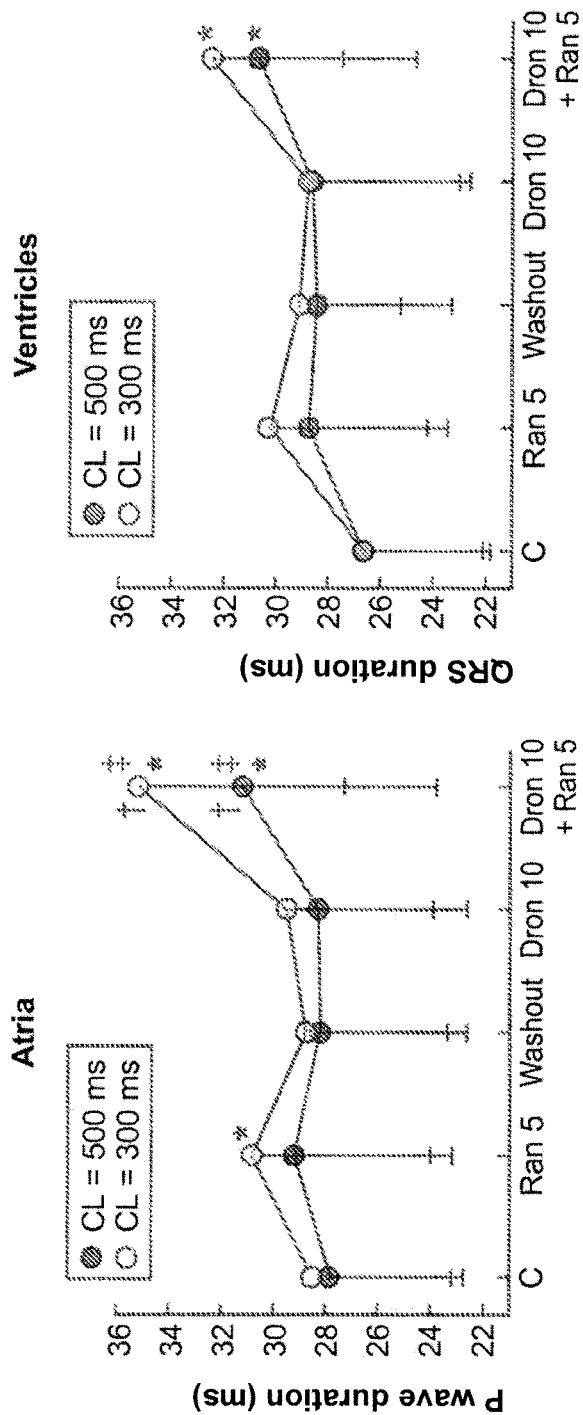
FIG. 5. Effects of ranolazine and dronedarone, alone or combined, on conduction time in coronary-perfused atrial and ventricular preparations. Conduction time was estimated by measuring the duration of "P wave" and "QRS" complexes of ECG recordings from coronary-perfused atrial and ventricular preparations. * p<0.05 versus respective control (C). † p<0.05 versus Washout. ‡ p<0.05 versus Dron 10. n=6-7.
Figure 6:
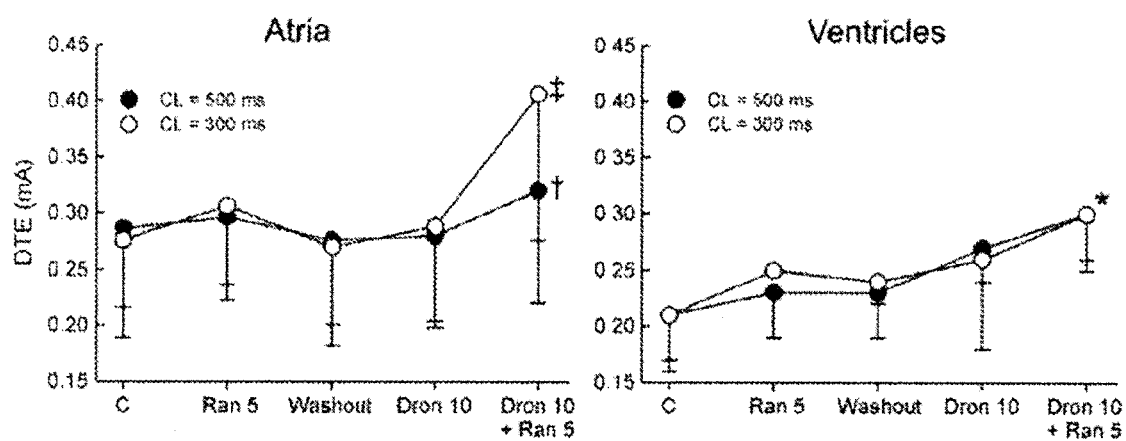
FIG. 6. Effects of ranolazine (5 μM) and dronedarone (10 μM), alone or combined to depress excitability (i.e. diastolic threshold of excitation, DTE). DTE measurements were obtained from endocardial pectinate muscle (atria) and epicardium (ventricles). * p<0.05 versus control (C); † p<0.05 versus Washout; ‡ p<0.05 versus control, Ran 5, Washout, and Dron 10. n=5-9.
Figure 13:
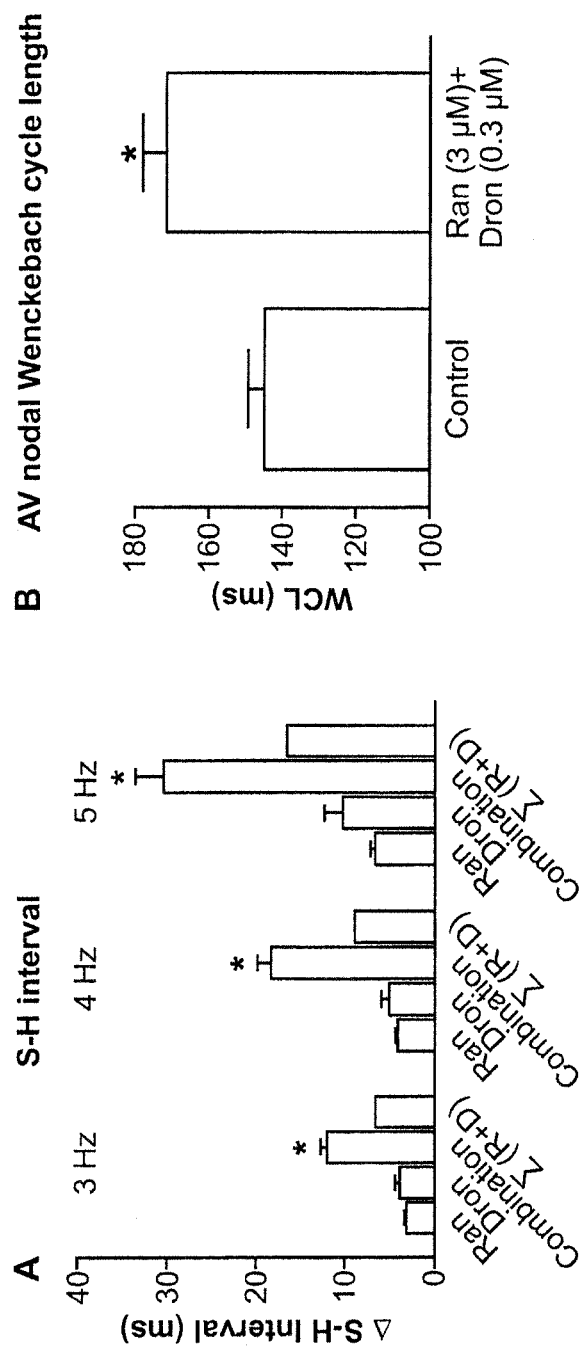
FIG. 13. Synergistic effect of ranolazine and dronedarone alone and in combination to increase the S-H interval (AV nodal conduction) and AV nodal Wenckebach cycle length in guinea pig isolated hearts. Baseline values of S-H interval at 3, 4 and 5 (Hertz) Hz were 35±2, 42±2 and 51±2 ms, respectively. Ran: ranolazine (3 μM, n=14): Dron: dronedarone (0.3 μM, n=14); significantly different from the Σ(R+D), a calculated sum of the experimentally measured individual effects of ranolazine and dronedarone; *, the experimentally measured value for the effect of the combination of ranolazine and dronedarone is significantly different from the calculated Σ(R+D), p<0.01.

Although the data in the dog model (FIGS. 1 to 12) focus on the synergistic effect of ranolazine and dronedarone in atrial fibrillation, FIG. 6 shows that ranolazine and dronedarone increased ventricular DTE (deceleration time of E-wave). This suggests that the combination therapy described herein may reduce ventricular excitability and thus, ventricular tachyarrhythmia. Further, FIG. 13 shows the synergistic effect of ranolazine and dronedarone on AV nodal conduction also suggests the combination's utility in ventricular rate control. Still further, FIGS. 15 to 20 shows that the combination does not present proarrhythmic risks suggesting that the combination is useful in treating ventricular tachyarrhythmia. FIGS. 24 to 26 shows the effect of ranolazine and dronedarone on DAD in ventricular myocytes suggesting the utility of the combination in ventricular tachyarrhythmia.

Accordingly, the invention is also directed to a method of treating or preventing supraventricular tachyarrhythmia or ventricular tachyarrhythmia in a patient in need thereof comprising coadministering a synergistically therapeutic amount of dronedarone or pharmaceutically acceptable salt or salts thereof and equal to a synergistically therapeutic amount ranolazine or pharmaceutically salt or salts thereof.

Additionally, it is contemplated that the combination therapy reduces ventricular fibrillation in addition to atrial fibrillation. Thus, in one embodiment, the invention is directed to a method of preventing ventricular fibrillation in patients susceptible to ventricular fibrillation, said method comprising coadministering to the patient synergistically therapeutic amounts of dronedarone and ranolazine or pharmaceutically acceptable salt or salts thereof.

As mentioned above, prolonged atrial fibrillation often results in development of congestive heart failure and/or stroke. In addition, patients with atrial fibrillation have increased risks of hospitalization and death. Thus, as a consequence of treating and preventing atrial fibrillation and ventricular arrhythmia, the combination therapy is expected to reduce hospitalization and death, the development of heart failure, and incidence of stroke. It is further contemplated that by reducing or preventing atrial fibrillation, emboli and blood clot formation is attenuated or reduced. Accordingly, in one aspect, the invention is directed to the method of preventing congestive heart failure and/or stroke in a patient by coadministration of dronedarone or a salt or salts thereof and ranolazine or a salt or salts thereof.

2.1 Dosing

For all of the methods just described, it is contemplated that at least one of either ranolazine or salt or salts thereof or dronedarone or salt or salts thereof is administered in a less than standard therapeutic dose which becomes therapeutically effective as a consequence of its coadministration with the other drug. However, it is also contemplated that dronedarone and ranolazine may also both be administered in a therapeutically effective amount. In some embodiments, the dronedarone is administered in a synergistically effective dose and ranolazine is administered in a standard therapeutically effective dose. In other embodiment, ranolazine is administered in a less than standard therapeutic dose and dronedarone is administered in a standard therapeutically effective dose. In still other embodiments, both ranolazine and dronedarone are administered in less than standard therapeutic doses. The expression "synergistically therapeutic amounts of dronedarone and ranolazine or pharmaceutically acceptable salt or salts thereof" is intended to encompass all possible combinations of standard and less than standard therapeutic doses of ranolazine and it therapeutically acceptable salts and dronedarone or its therapeutically acceptable salts.

In some embodiments, dronedarone or the salt or salts thereof and ranolazine or the salt or salts thereof are administered separately.

Ranolazine and dronedarone may be given to the patient in either single or multiple doses by any of the accepted modes of administration of agents having similar utilities, for example as described in those patents and patent applications incorporated by reference, including buccal, by intra-arterial injection, intravenously, intraperitoneally, parenterally, intramuscularly, subcutaneously, orally, or via an impregnated or coated device such as a stent, for example, or an artery-inserted cylindrical polymer. In one embodiment, ranolazine or the salt or salts thereof and dronedarone or the salt or salts thereof are administered intravenously.

In one embodiment, ranolazine or the salt or salts thereof and dronedarone or the salt or salts thereof are administered orally. Dronedarone or the salt or salts thereof and ranolazine or salt or salts thereof may also be administered as a combined dosage unit, such as, for example, in a tablet.

As mentioned above, dronedarone or the salt or salts thereof and ranolazine or the salt or salts thereof may be administered in a synergistically therapeutic amount or a synergistically effective amount. Therefore, in some embodiments, the amount of ranolazine or salt or salts thereof administered is from about 50 mg to about 3000 mg daily or from about 50 mg to about 2500 mg daily, or from about 50 mg to about 2000 mg daily, or from about 50 mg to about 1500 mg daily. Further, the amount of dronedarone or salt or salts thereof administered is from about 50 mg to about 800 mg daily or from about 50 mg to about 700 mg daily, or from about 50 mg to about 600 mg daily, or from about 50 mg to about 500 mg daily, or from about 50 mg to about 400 mg daily. These aggregate daily doses may be administered to the patient either once or twice a day.

Additionally, it is contemplated that ranolazine or the salt or salts thereof is administered as a sustained release formulation and/or dronedarone or salt or salts thereof is administered as an immediate release or sustained release formulation. This is more thoroughly discussed in the next section.

In one embodiment then, the patent under treatment is already taking a maintenance dose of dronedarone ranging from 400 to 800 mg with a typical dose being 400 mg twice daily. To this dosing regimen is then added ranolazine at from about 300 mg to about 1000 mg. Typically, the dose may be administered as follows: 1000 mg twice daily (2×500 mg), 750 mg twice daily (2×375 mg), 500 mg twice daily (1×500 mg), 375 mg twice daily (1×375 mg), or 600 mg twice daily (2×300 mg). By administering such therapeutic doses of ranolazine the amount of dronedarone can then be decreased to from about 50 to about 300 mg or about 200 mg daily thereby greatly reducing the incidence of adverse events.

3. Active Ingredients and Compositions 3.1 Ranolazine

U.S. Pat. No. 4,567,264, discloses ranolazine, (±)-N-(2,6-dimethylphenyl)-4-[2-hydroxy-3-(2-methoxyphenoxy)-propyl]-1-piperazineacetamide, and its pharmaceutically acceptable salts, and their use in the treatment of cardiovascular diseases, including arrhythmias, variant and exercise-induced angina, and myocardial infarction.

This patent also discloses intravenous (IV) formulations of dihydrochloride ranolazine further comprising propylene glycol, polyethylene glycol 400, Tween 80 and 0.9% saline.

U.S. Pat. No. 5,506,229, discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. Oral and parenteral formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers. This patent also discloses IV ranolazine formulations which at the low end comprise 5 mg ranolazine per milliliter of an IV solution containing about 5% by weight dextrose. And at the high end, there is disclosed an IV solution containing 200 mg ranolazine per milliliter of an IV solution containing about 4% by weight dextrose.

The presently preferred route of administration for ranolazine and its pharmaceutically acceptable salts and esters is oral. A typical oral dosage form is a compressed tablet, a hard gelatin capsule filled with a powder mix or granulate, or a soft gelatin capsule (softgel) filled with a solution or suspension. U.S. Pat. No. 5,472,707, discloses a high-dose oral formulation employing supercooled liquid ranolazine as a fill solution for a hard gelatin capsule or softgel.

U.S. Pat. No. 6,503,911, discloses sustained release formulations that overcome the problem of affording a satisfactory plasma level of ranolazine while the formulation travels through both an acidic environment in the stomach and a more basic environment through the intestine, and has proven to be very effective in providing the plasma levels that are necessary for the treatment of angina and other cardiovascular diseases.

U.S. Pat. No. 6,852,724, discloses methods of treating cardiovascular diseases, including arrhythmias variant and exercise-induced angina and myocardial infarction.

U.S. Patent Application Publication Number 2006/0177502, discloses oral sustained release dosage forms in which the ranolazine is present in 35-50%, preferably 40-45% ranolazine. In one embodiment the ranolazine sustained release formulations of the invention include a pH dependent binder; a pH independent binder; and one or more pharmaceutically acceptable excipients. Suitable pH dependent binders include, but are not limited to, a methacrylic acid copolymer, for example Eudragit® (Eudragit® L100-55, pseudolatex of Eudragit® L100-55, and the like) partially neutralized with a strong base, for example, sodium hydroxide, potassium hydroxide, or ammonium hydroxide, in a quantity sufficient to neutralize the methacrylic acid copolymer to an extent of about 1-20%, for example about 3-6%. Suitable pH independent binders include, but are not limited to, hydroxypropylmethylcellulose (HPMC), for example Methocel® E10M Premium CR grade HPMC or Methocel® E4M Premium HPMC. Suitable pharmaceutically acceptable excipients include magnesium stearate and microcrystalline cellulose (Avicel® pH101).

3.2 Dronedarone

U.S. Pat. No. 5,223,510 discloses dronedarone, N-(2-Butyl-3-(p-(3-(dibutylamino)propoxy)benzoyl)-5-benzofuranyl)methanesulfonamide, its pharmaceutically acceptable salts, and their use in the treatment of angina pectoris, hypertension, arrhythmias, and cerebral circulatory inefficiency. Dronedarone hydrochloride is an example of a commonly used pharmaceutically acceptable salt of dronedarone.

U.S. Pat. No. 6,939,865 discloses a pharmaceutical composition comprising dronedarone or its pharmaceutically acceptable salt as an active principle, physiologically acceptable buffer solution capable of maintaining the pH of the composition between 3 and 5, and a physiologically acceptable water-soluble beta-cyclodextrin derivative. The buffer solution is an aqueous solution comprising a buffer system chosen from the following: acetic acid/alkali metal acetate, fumaric acid/alkali metal fumarate, succinic acid/alkali metal succinate, citric acid/alkali metal citrate, tartaric acid/alkali metal tartarate, lactic acid/alkali metal lactate, maleic acid/alkali metal maleate, methanesulphonic acid/alkali metal methanesulphonate, or monoalkali metal phosphate. The composition is for parenteral administration in the form of an injectable solution.

U.S. Pat. No. 7,022,343 discloses a liquid pharmaceutical composition comprising 1) dronedarone or its pharmaceutically acceptable salt as an active principle, 2) an aqueous solvent comprising at least 50% by weight of water, 3) dispersed or solubilized within the solvent, biocompatible, biodegradable, synthetic, water soluble and covalently reactive macromers polymerizable to form a compliant tissue adhesive hydrogel degrading in a period of less than one month after application to the tissue, said macromers comprising on average per molecule at least one hydrophilic domain, at least one biodegradable region comprising carbonate linkages, and at least two polymerizable groups, and 4) a polymerization initiator. The composition is for reliable application and local controlled release of dronedarone to tissues of the heart or blood vessels, especially in conjunction with cardiac bypass or other cardiac surgery, have been developed. Dronedarone is incorporated into hydrogels that adhere to the tissues to which the anti-arrhythmic drugs are to be delivered and then biodegrade. The hydrogels compositions and patches containing anti-arrhythmic drugs may be formed in vitro or in vivo. Preferred hydrogels are tissue adherent and biodegradable within seven to ten days following application. Most preferred hydrogels are formed of synthetic polymers that provoke minimal inflammation or fibrosis. The hydrogels can be applied directly to the tissue where drug delivery is desired, by spraying or painting the gel onto the tissue, or in the form of a "patch" that provides a defined dosage of drug for release at the site of application.

U.S. Pat. No. 7,323,493 discloses a pharmaceutical composition comprising dronedarone or its pharmaceutically acceptable salt as an active principle, and a pharmaceutically acceptable nonionic hydrophilic surfactant selected from poloxamers, optionally in combination with one or more pharmaceutical excipients, wherein the nonionic hydrophilic surfactant is present in a proportion of from 5% to 15% by weight of the active principle in base form. The composition is for oral administration in the form of a tablet, a granule, a gelatin capsule, or a powder.

In one embodiment, the methods of the invention employ a tablet comprising dronedarone. The tablet optionally additionally comprises hypromellose, starch, crospovidone, poloxamer 407, lactose monohydrate, colloidal silicon dioxide, and magnesium stearate. The tablet may also optionally comprise ranolazine.

3.3 Pharmaceutical Formulations

As mentioned above, dronedarone and ranolazine may be coadministered, meaning that the two active ingredients may be formulated separately but administered at similar times (i.e., either together or one after the other). Coadministered also means that dronedarone and ranolazine may be co-formulated into a combined dosage unit. Accordingly, in one embodiment, the invention is directed to pharmaceutical formulations comprising a synergistically therapeutic amount of dronedarone or pharmaceutically acceptable salt or salts thereof, a synergistically therapeutic amount of ranolazine or pharmaceutically acceptable salt or salts thereof, and a pharmaceutically acceptable carrier.

In another embodiment, the formulation comprises a synergistically effective amount of ranolazine or salt or salts thereof and/or dronedarone or salt or salts thereof. In certain embodiments, the formulations are formulated for either intravenous or oral administration. In still other embodiment, the two active ingredients are co-formulated into a combined dosage unit. In still yet other embodiments, the two active ingredients are formulated separately for coadministration.

3.4 Coformulations

In certain embodiments of the present invention, the ranolazine and dronedarone are coformulated into a combined dosage unit or unitary dosage form suitable for oral administration. In certain embodiments, the ranolazine is formulated as a sustained release formulation. In certain embodiments, the dronedarone is formulated for immediate release or sustained release.

In one embodiment, the formulation is in tablet form or capsule form. In embodiment, the tablet or capsule comprises from about 10 mg to about of 800 mg of dronedarone or a pharmaceutically acceptable salt or salts thereof. In another embodiment, the tablet or capsule comprises from about 25 mg to about 600 mg of dronedarone or a pharmaceutically acceptable salt or salts thereof. In yet another embodiment, the tablet or capsule comprises from about 25 mg to about 400 mg of dronedarone or a pharmaceutically acceptable salt or salts thereof. In still yet another embodiment, the tablet or capsule comprises from about 50 mg to about 200 mg of dronedarone or a pharmaceutically acceptable salt or salts thereof.

In one embodiment, the tablet or capsule comprises from about 50 mg to about 1000 mg of ranolazine or a pharmaceutically acceptable salt or salts thereof. In another embodiment, the tablet or capsule comprises from about 100 mg to about 750 mg of ranolazine or a pharmaceutically acceptable salt or salts thereof. In yet another embodiment, the tablet or capsule comprises from about 150 mg to about 375 mg of ranolazine or a pharmaceutically acceptable salt or salts thereof.

In one such embodiment, the ranolazine composition is placed in a portion of the tablet which is separate from, but in contact with, the portion of the tablet containing the dronedarone composition. It will be understood that the unitary dosage form may comprise simply compressing the ranolazine composition and the dronedarone composition into a multilayer tablet or conventionally processed into other conventional unitary dosage forms such as a capsules. The multilayer tablets and capsules suitable for use in the present invention can be fabricated using methods known in the art using standard machinery.

The tablets may comprise two layers, i.e. a first layer which comprises the dronedarone and is formulated for immediate release or sustained release, and a second layer which comprises the ranolazine and is formulated for sustained release. Alternatively, the multilayer tablet may comprise an inner layer and an outer layer, where the inner layer comprises the sustained release ranolazine formulation and where the outer layer comprises the immediate release or sustained release dronedarone layer. In another embodiment, the ranolazine and dronedarone are coformulated into a capsule, where the capsule allows for the immediate release or sustained release of dronedarone and the sustained release of ranolazine. For example, the capsule may contain granules of both dronedarone and ranolazine, where the granules have been formulated such that the dronedarone is available for immediate release or sustained release and the Ranolazine is formulated for sustained release. Alternatively, the capsule may contain a liquid immediate release or sustained release formulation of dronedarone and a solid sustained release formulation of ranolazine. However, such embodiments are exemplary and are not intended to limit the formulations of the present invention.

A multilayer tablet can be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active agent or dispersing agent. Molded tablets may be made by molding in a suitable machine a mixture of the powdered active ingredient moistened with an inert liquid diluent. The tablets may optionally be coated or scored.

The tablets may contain one or more agents including sweetening agents, flavoring agents, coloring agents and preserving agents, in order to provide a palatable preparation. Tablets containing the active ingredients in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

3.5 Additional Formulations

Formulations also contemplated by the present invention may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. The same formulations are contemplated for separate administration of ranolazine and dronedarone.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The ideal forms of the apparatus for administration of the novel combinations for atrial fibrillation and other methods of the invention consist therefore of (1) either a syringe comprising 2 compartments containing the 2 active substances ready for use or (2) a kit containing two syringes ready for use.

In making a pharmaceutical compositions that include ranolazine and dronedarone, the active ingredients are usually diluted by an excipient or carrier and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. As discussed above, given the reduced bioavailability of ranolazine, sustained release formulations are generally preferred. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345.

The compositions are preferably formulated in a unit dosage form. The term "unit dosage forms" or "combined dosage unit" refers to physically discrete units suitable as unitary dosages for human subjects and other mammals, each unit containing a predetermined quantity of the active materials calculated to produce the desired therapeutic effect, in association with a suitable pharmaceutical excipient (e.g., a tablet, capsule, ampoule). The active agents of the invention are effective over a wide dosage range and are generally administered in a pharmaceutically effective amount. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredients are mixed with a pharmaceutical excipient to form a solid preformulation composition containing a homogeneous mixture of a compound of the present invention. When referring to these preformulation compositions as homogeneous, it is meant that the active ingredients are dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage element, the latter being in the form of an envelope over the former. Ranolazine and the co-administered agent(s) can be separated by an enteric layer that serves to resist disintegration in the stomach and permit the inner element to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Additional embodiments of the invention include kits comprising a synergistically therapeutic amount of ranolazine or a pharmaceutically acceptable salt or salts thereof and a synergistically therapeutic amount of dronedarone or a pharmaceutically acceptable salt or salts thereof.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Dronedarone as used in this invention is well known in the art, and is commercially available. Ranolazine is also commercially available or may be prepared by conventional methods such as in the manner disclosed in U.S. Pat. No. 4,567,264, the entire disclosure of which is hereby incorporated by reference. Additionally, the abbreviations used throughout have the following meanings:

μM=micromolar cm=centimeter kg=kilogram mA=milliamp min=minute mm=millimeter mM=millimolar ms=millisecond MΩ=Mega Ohms

Example 1

Atrial-Selective Depression of Sodium Channel Dependent Parameters and Suppression of Atrial Fibrillation by the Combination of Dronedarone and Ranolazine: a Synergistic Effect In experimental studies involving isolated canine atria, separate application of ranolazine and chronic amiodarone have been shown to exert atrial-selective depression of sodium channel current ($I_{Na}$)-dependent parameters and to effectively suppress AF.[9-13] The combination of chronic amiodarone and acute of ranolazine (at relatively low concentration) caused marked atrial-selective depression of $I_{Na}$-dependent parameters and very effective suppression of AF.[14] The present study tested the hypothesis that the combination of acute dronedarone and ranolazine has similar synergism to that of the combination of chronic amiodarone and acute ranolazine resulting in potent atrial-selective electrophysiologic actions leading to marked suppression of atrial arrhythmias.

Methods

Coronary-Perfused Atrial and Ventricular Preparations

Experiments were performed using isolated coronary-perfused canine right atrial (RA) and left ventricular (LV) preparations (≈3×1.5×1 cm). Isolation and perfusion of the preparations were as previously described.[9,15,16] Briefly, preparations were dissected from hearts removed from anesthetized (sodium pentobarbital) adult mongrel dogs (20-30 kg). Unfolded RA with attached rim of the right ventricle was cannulated and perfused with cold cardioplegic solution (4-8° C.) through the ostium of the right coronary artery; the LV wedge was perfused through a diagonal branch of the left anterior descending coronary artery. Unperfused tissue was removed with a razor blade. Cut ventricular and atrial branches were ligated using silk thread. The preparations were then transferred to a temperature-controlled bath and arterially-perfused with Tyrode's solution by use of a roller pump. The composition of the Tyrode's solution was (in mM): NaCl 129, KCl 4, $NaH_2PO_4$ 0.9, $NaHCO_3$ 20, $CaCl_2$ 1.8, $MgSO_4$ 0.5, and D-glucose 5.5, buffered with 95% $O_2$ and 5% $CO_2$ (37±0.5° C., pH=7.35)

Transmembrane action potential (AP) recordings were obtained using floating glass microelectrodes at a sampling rate of 40 kHz. A pseudo-electrocardiogram (ECG) was recorded using two electrodes consisting of Ag/AgCl half cells placed in the Tyrode's solution bathing the preparation, 1.0 to 1.5 cm from the two opposite sides of the atrial or ventricular coronary-perfused preparations. Conduction time was approximated by the duration of "P wave" in atria and "QRS complex" in ventricles, at a level representing 10% of "P wave" and "QRS" amplitude. Diastolic threshold of excitation (DTE) was determined by increasing stimulus intensity in 0.01 mA steps. Effective refractory period (ERP) was measured by delivering premature stimuli at progressively shorter S1-S2 intervals after every 10 basic beats at a pacing cycle length (CL) of 500 ms (5 ms steps; 2 times DTE). Post-repolarization refractoriness (PRR) was recognized when ERP exceeded action potential duration measured at 90% repolarization ($APD_{90}$) in the ventricle and APD measured at 70% repolarization ($APD_{70}$) in atria. Ventricular ERP was coincident with $APD_{90}$, whereas atrial ERP was generally coincident with $APD_{70-75}$.[9] The shortest $S_1$-$S_1$ permitting 1:1 activation was measured by progressively shortening pacing CL starting from a CL of 500 ms.

Stable AP recordings could not be readily obtained in the vigorously contracting perfused preparations. The largest recorded maximum rate of rise of the AP upstroke ($V_{max}$) values per experimental condition were taken for statistical comparison. Only APs having amplitudes of at least 100 mV were considered in the analysis. The largest $V_{max}$ criterion was used because this was associated with the largest amplitude and the most negative resting membrane potential, depicting full or near full impalement. In determining use-dependent depression of $V_{max}$, values were normalized to the $V_{max}$ value at a CL of 500 ms for each experiment and then averaged.

Because of their dependence on peak $I_{Na}$, $V_{max}$, DTE, PRR, and conduction time as well the shortest S1-S1 interval permitting 1:1 activation are referred to as $I_{Na}$-dependent parameters.

Experimental Protocols

The equilibration period for the coronary-perfused preparations was 30-120 min. The preparations were exposed to 5 μM ranolazine, 10 μM dronedarone (after 30 min washout of ranolazine), and the combination of these agents for at a period of at least 20 min. In time-control experiments, 20 minutes was sufficient to achieve steady-state in the effects of each of the drugs to alter electrophysiologic parameters. Recordings were obtained at a cycle length (CL) of 500 and 300 ms, unless otherwise indicated. Changes in $V_{max}$, QRS, DTE, and CT were measured from the 15 to 25th beats in atria and 16th to 20th beat in LV after acceleration from a CL of 500 to 300 ms and averaged; steady-state was achieved within 15 beats. When determining the shortest $S_1$-$S_1$ pacing rate permitting 1:1 activation, the stimulation intensity was DTE×2, determined at a CL of 500 ms.

To assess the anti-AF potential of ranolazine, dronedarone, and their combination, we used an acetylcholine (ACh, 1.0 μM)—mediated AF model. In the presence of ACh, premature electrical stimulation (PES) or rapid pacing (CL=50-80 ms) induces persistent AF in 100% of canine coronary-perfused right atrial preparations.[9] The effect of the drugs was assessed to prevent (series 1) the induction of AF. In a separate set of preparations, the ability of these agents was evaluated to terminate (series 2) persistent AF. In the first series, ACh was added to the perfusate 20-30 min after the start of perfusion with 5 μM ranolazine, 10 μM dronedarone, or the combination of these agents. This was followed by attempts to induce the arrhythmia electrically. In the second series, the agents were added to the perfusate during ACh-mediated persistent AF (on the 5-6th minutes after the start of the arrhythmia). In cases in which the drug terminated AF, we attempted to re-induce the arrhythmia with rapid pacing.

Superfused Pulmonary Vein Sleeve Preparation

Pulmonary vein (PV) sleeve preparations (approximately 2.0×1.5 cm) were isolated from left canine atria. The thickness of the preparation was approximately 2 mm. Left superior PVs were used preferentially in most experiments. The preparations were placed in a small tissue bath and superfused with Tyrode's solution of the following composition (mM): 129 NaCl, 4 KCl, 0.9 $NaH_2PO_4$, 20 $NaHCO_3$, 1.8 $CaCl_2$, 0.5 $MgSO_4$, 5.5 glucose, buffered with 95% $O_2$/5% $CO_2$ (35±0.5° C.). The PV preparations were stimulated at a basic cycle length (BCL) of 1000 ms during the equilibration period (1 h) using electrical pulses (1-3 ms duration, 2.5 times diastolic threshold intensity) delivered through silver bipolar electrodes insulated except at the tips. Transmembrane potentials were recorded (at a sampling rate of 40 kHz) using glass microelectrodes filled with 3 M KCl (10-20 MΩ DC resistance) connected to a high input-impedance amplification system (World Precision Instruments, model KS-700, New Haven, Conn.). The following parameters were measured: DTE, $V_{max}$, and shortest $S_1$-$S_1$ permitting 1:1 activation. Acetylcholine (ACh, 1 μM), isoproterenol (1 μM), high calcium or their combination were used to induce late phase 3 EADs, DADs and triggered activity. The combination of parasympathetic and sympathetic stimulation has been shown to facilitate the development of late phase 3 EADs in PV sleeve preparations,[17,18] whereas sympathetic stimulation is known to lead to calcium overload, a condition responsible for the development of DADs.[19,20] DADs or EADs were elicited using stimulation trains of 20 beats introduced at progressively faster rates followed by a pause.

Drugs

Dronedarone and ranolazine were dissolved in 100% dimethyl sulfoxide (DMSO) and distilled water, respectively, in stock solutions of 10 mM. Acetylcholine and isoproterenol (both SIGMA, MO) were dissolved in distilled water as stock solutions of 10 and 1 mM, respectively.

Statistics

Statistical analysis was performed using one-way analysis of variance (ANOVA) for multiple groups or repeated measures ANOVA followed by Bonferroni's test, as appropriate. All data are expressed as mean±SD. Statistical significance was assumed at p<0.05.

Results

Coronary Perfused Right Atrial and Left Ventricular Preparations

Figure 1:
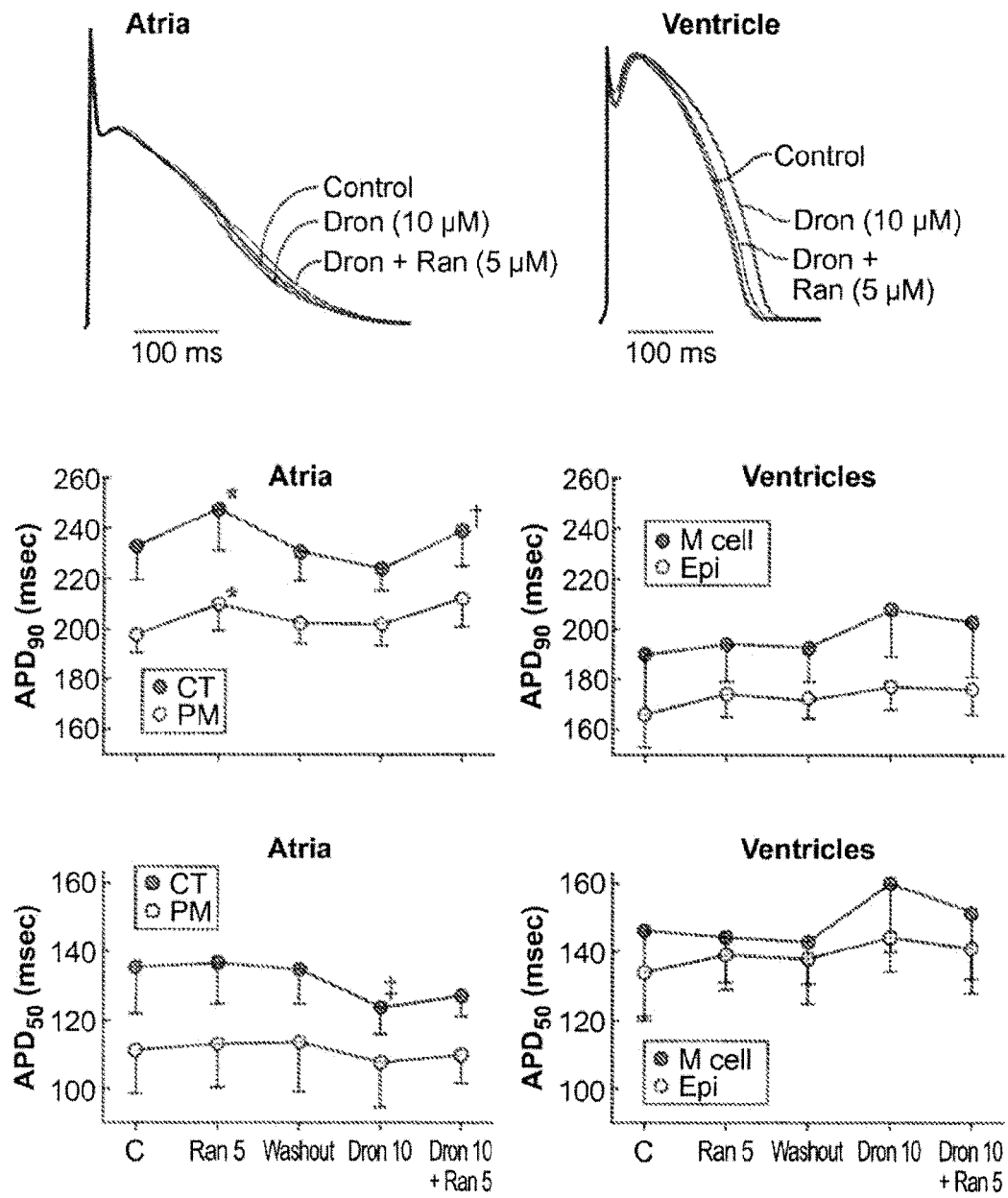
FIG. 1. Effects of ranolazine and dronedarone, alone or combined these agents on action potential duration (APD) from different atrial and ventricular regions. Shown are representative action potentials and summary data of the effect on $APD_{50}$ and $APD_{90}$ in coronary-perfused atrial and ventricular preparations stimulated at a cycle of length (CL) of 500 ms (millisecond or msec). n=7-8. CT=crista terminalis, PM=pectinate muscle, M cell=M cell region, Epi=epicardium. Ran 5=ranolazine 5 μM, Dron 10=dronedarone 10 μM. * $p<0.05$ versus respective control (C). † $p<0.05$ versus Dron 10, ‡ $p<0.05$ versus Washout.

Ranolazine (5 μM) moderately prolonged $APD_{90}$ in atria, but caused no statistically significant change in $APD_{90}$ of the ventricular preparations (FIG. 1). $APD_{50}$ was not altered by ranolazine in either atria or ventricles (FIG. 1). Washout of ranolazine restored the $APD_{90}$ values to control levels. In atria, dronedarone (10 μM) abbreviated repolarization, reaching statistical significance for abbreviation of $APD_{50}$ in CT (FIG. 1). In ventricular preparations, dronedarone slightly prolonged APD, although without reaching statistical significance. The addition of 5 μM ranolazine to the solution containing 10 μM dronedarone prolonged $APD_{90}$ in atria, while causing a non-statistically significant abbreviation in the ventricles (FIG. 1). $APD_{50}$ was not altered by the combination of ranolazine and dronedarone in either atria or ventricles.

Figure 2:
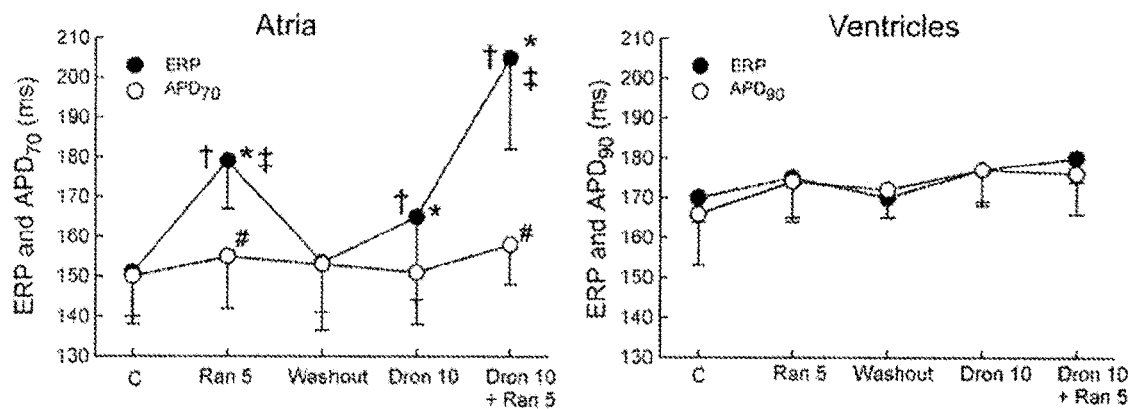
FIG. 2. Ranolazine and dronedarone induce prolongation of effective refractory period (ERP) and development of post-repolarization refractoriness in atria (PRR, the difference between ERP and $APD_{70}$ in atria and between ERP and $APD_{90}$ in ventricles; ERP corresponds to $APD_{70-75}$ in atria and to $APD_{90}$ in ventricles). CL=500 ms. Ventricular data were obtained from epicardium and atrial data from endocardial pectinate muscle (PM). n=7-8. * $p<0.05$ versus respective control (C). † $p<0.05$ versus washout. ‡ $p<0.05$ versus Dron 10. # $p<0.05$ versus respective ERP.

When applied separately, both ranolazine (5 μM) and dronedarone (10 μM) prolonged ERP more than $APD_{70}$ in atria, leading to the development of PRR (FIG. 2). The extent of PRR was greater following ranolazine than dronedarone. Ventricular ERP was not altered by either ranolazine or dronedarone. The combination of dronedarone and ranolazine caused a significant synergistic prolongation of ERP in atria, but did not change ERP in ventricles, thus resulting in a striking atrial-specific PRR (FIG. 2).

Figure 3:
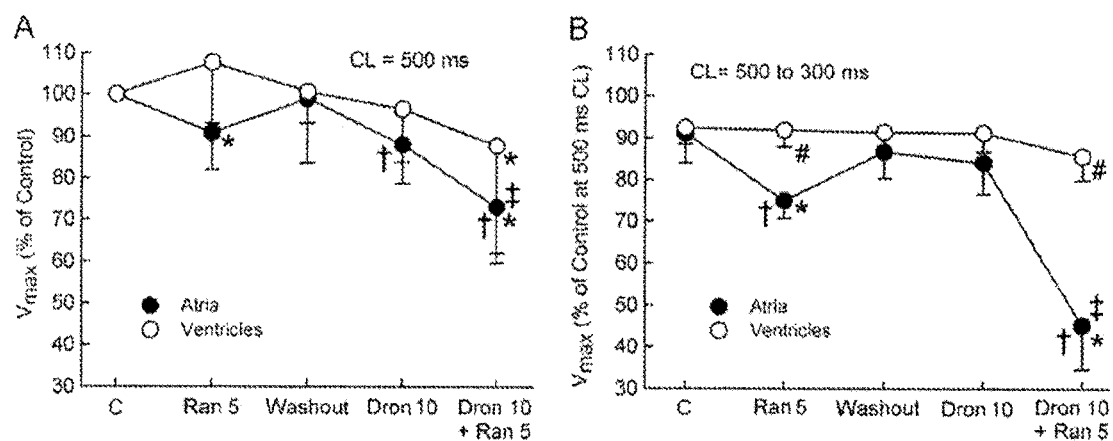
FIG. 3. Ranolazine and dronedarone alone or combined cause potent atrial-selective rate-dependent inhibition of $V_{max}$. A: $V_{max}$ of atrial and ventricular cardiac preparations paced at a cycle length (CL) of 500 ms (left panel) as a % of control. B: $V_{max}$ of atrial and ventricular action potentials following acceleration from a CL of 500 to 300 ms as a % of $V_{max}$ value recorded at a CL of 500 ms in Controls. "Atria" represent combined PM and CT data. "Ventricles" represent combined Epi and M cell data from ventricular wedge preparations. n=7-8. * $p<0.05$ versus respective control (C). † $p<0.05$ versus washout. ‡-$p<0.05$ versus Dron 10. #-$p<0.05$ versus respective atrial values.
Figure 4:
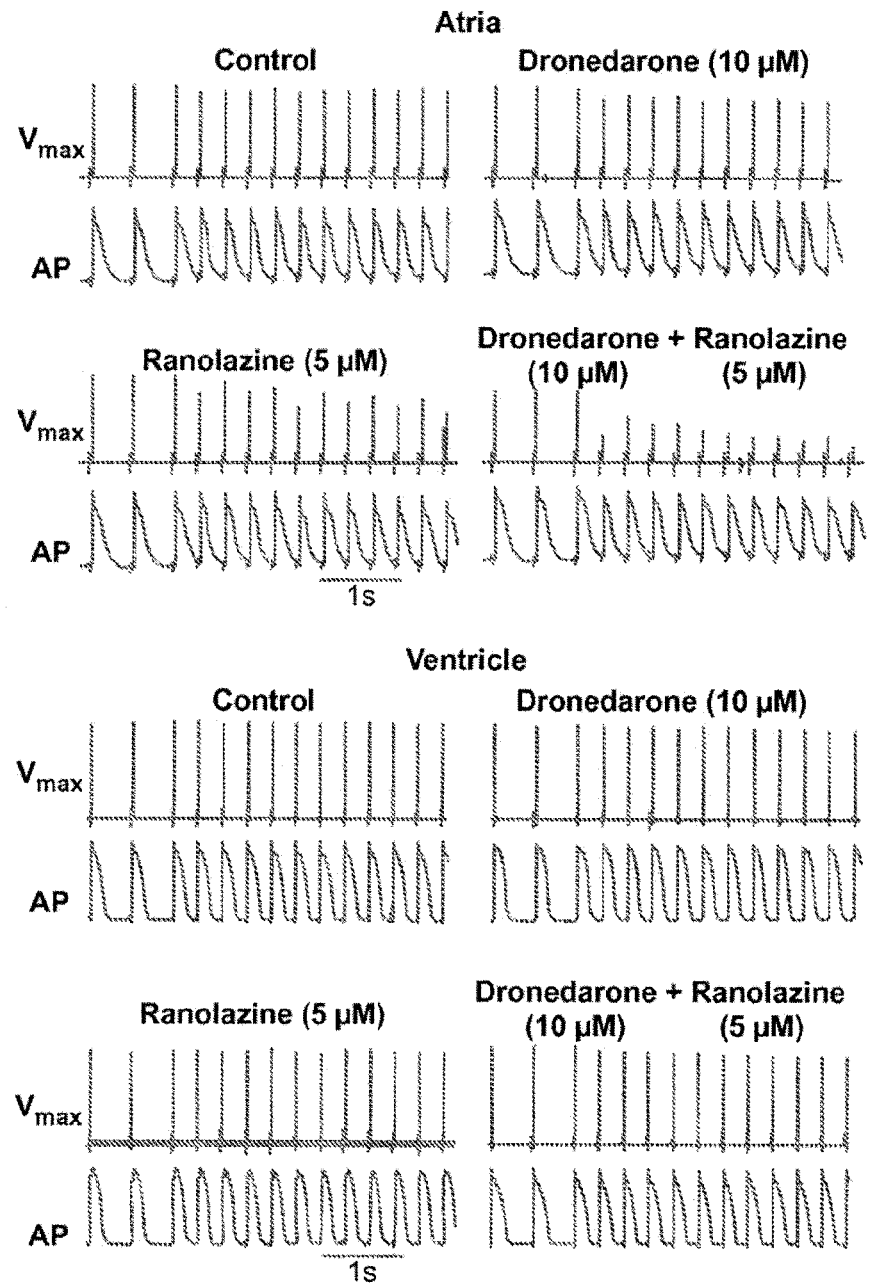
FIG. 4. Atrial-selective synergistic depression of the maximal action potential upstroke velocity ($V_{max}$) by the combination of dronedarone and ranolazine at rapid activation rates. Shown are action potential (AP) tracings and corresponding $V_{max}$ values recorded during acceleration of pacing rate from a CL of 500 to 300 ms. Mechanism contributing to rate-dependent atrial selectivity of ranolazine: the disappearance of the diastolic interval in atria, but not ventricles at the rapid activation rate (due to prolonged late phase 3 of the action potential in atria) reduces the rate of recovery of the sodium channel from drug-induced block, thus contributing to the atrial-selective effects of the drugs on $V_{max}$.

$V_{max}$ measured at a CL of 500 ms was reduced by ranolazine (5 μM) and by dronedarone (10 μM) in atria, but not in ventricles (FIGS. 3 and 4). At this pacing cycle length, a combination of these drugs led to a decrease in $V_{max}$ in both atria and ventricles, but predominantly in the former. In atria, an increase in pacing rate from a CL of 500 to 300 ms caused a much greater depression of $V_{max}$ when dronedarone and ranolazine were combined than when each of these drugs was used alone (FIGS. 3 and 4). In the ventricles, this acceleration of pacing rate led to only a modest reduction in $V_{max}$ under all conditions tested.

Conduction time estimated using the duration of "P wave" in atria and "QRS complex" in ventricles was not altered significantly in atria and ventricles by either ranolazine (5 μM) or dronedarone (10 μM) at a CL of 500 ms (FIG. 5). The combination of these drugs led to a statistically significant prolongation of "P wave" and "QRS complex" at a CL of 500 ms. At a faster pacing rate (CL=300 ms), atrial conduction time was statistically significantly increased by ranolazine, but not by dronedarone in atria, with neither agent causing a significant change in conduction time in ventricular myocardium. At a CL of 300 ms, the combination of dronedarone and ranolazine produced a significant conduction slowing in both atria and ventricles; with much more pronounced slowing in atria than ventricles.

DTE was not significantly affected by either ranolazine (5 μM) or dronedarone (10 μM) in either atria or ventricles at pacing CLs of 500 and 300 ms (FIG. 6). When these drugs were combined, DTE was increased significantly in both atria and ventricles at both pacing rates tested. The effect of the combination was most pronounced in atria and at a CL of 300 ms (FIG. 6).

Figure 7:
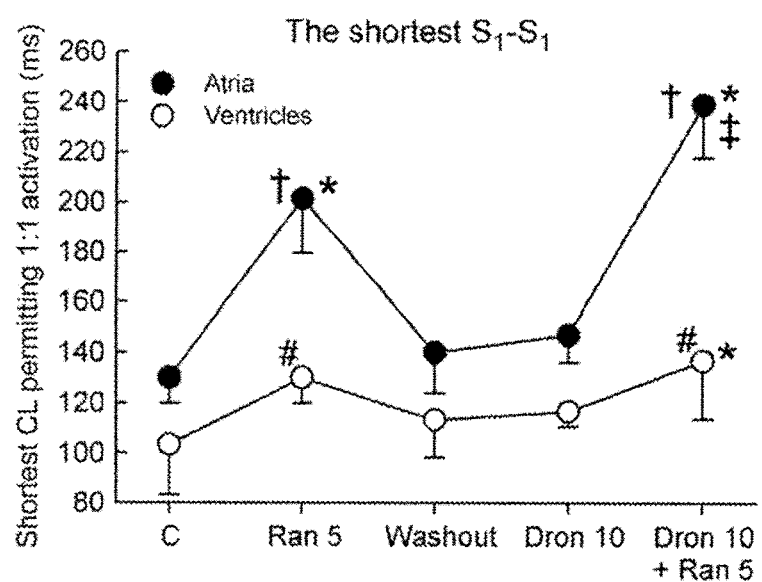
FIG. 7. Atrial-selective effect of ranolazine (5 μM) and dronedarone (10 μM) alone or combined to prolong the shortest cycle length (CL) permitting 1:1 activation. *<0.05 versus respective control; † P<0.05 versus Washout and Dron. ‡-P<0.05 versus Ran. #-p<0.001 versus respective atrial values.
Figure 8:
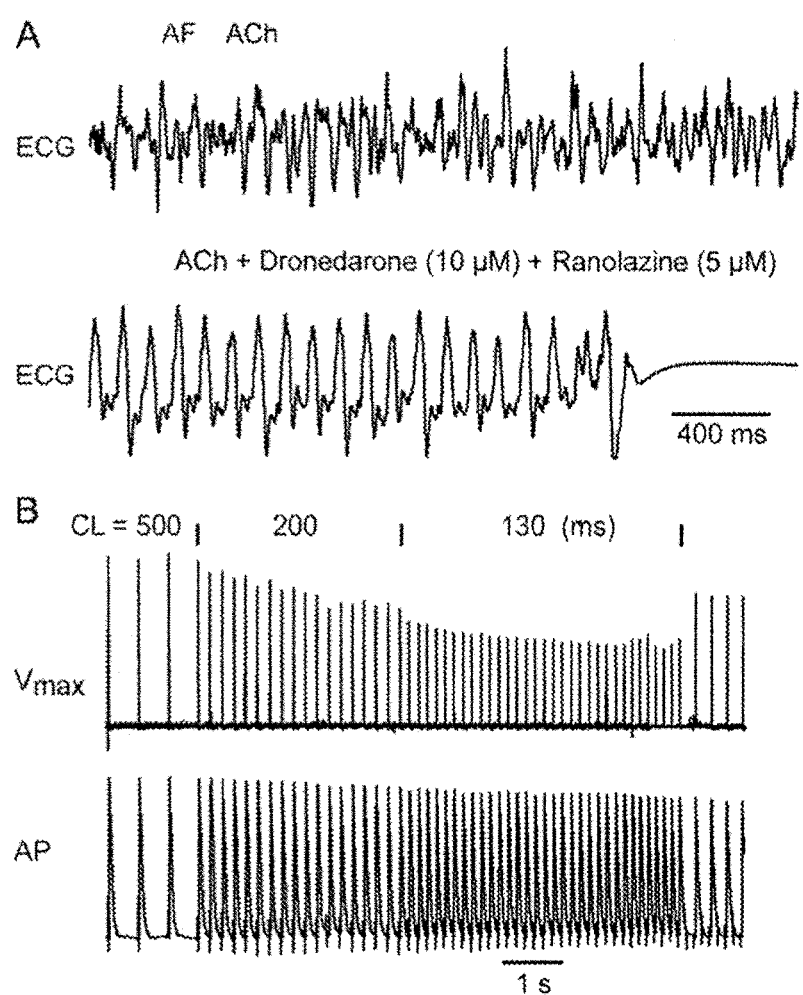
FIG. 8. The combination of dronedarone (10 μM) and ranolazine (5 μM) is effective in terminating persistent AF and/or preventing its induction in coronary-perfused right atria. A: Persistent acetylcholine (Ach) (0.5 μM)-mediated AF is terminated by the drug combination. AF is initially converted to flutter and then to sinus rhythm. B: The combination of dronedarone and ranolazine prevents rapid-pacing induction of AF following pretreatment with ACh (1 μM) due to depression of sodium channel (see $V_{max}$ reduction). Acceleration of pacing rate from a cycle length (CL) of 500 to 130 ms leads to failure of a 1:1 response.

Another sodium channel-mediated parameter, the shortest $S_1$-$S_1$ interval permitting 1:1 activation, was increased by ranolazine, but not by dronedarone in both atria and ventricles (FIG. 7). Ranolazine caused a greater increase in this parameter in atria than ventricles. When dronedarone and ranolazine were combined, the shortest $S_1$-$S_1$ interval was significantly increased in both atria and ventricles, but the extent of the change was much greater in atria than ventricles.

Atrial Fibrillation in Coronary-Perfused Right Atria

Persistent AF was induced in 100% of atria in the presence of 1 μM ACh.[9] Pretreatment of the coronary-perfused atrial preparations with a relatively low concentration of ranolazine (5 μM) prevented the induction of sustained AF in 2/7 atria (Table 1). In separate atrial preparations, 5 μM of ranolazine was effective in terminating persistent AF only in 1 out of 5 atria (Table 2). Dronedarone (10 μM) alone was not effective in preventing the induction of AF or terminating persistent AF (table 1 and 2). When dronedarone (10 μM) and ranolazine (5 μM) were combined, the success rate for preventing induction of persistent AF was markedly increased (in 8/9 atria per Table 1). This drug combination terminated persistent AF in 6 out of 10 atria (Table 2). AF could not be re-induced in any of the 6 preparations exposed to the drug combination. However, in 2 out of 6 atria, persistent atrial flutter or tachycardia (with a CL≥160 ms) could be induced by rapid pacing and/or PES.

TABLE 1

Effects of ranolazine (5 μM), dronedarone (10 μM), and their combination on atrial excitability and the induction of ACh-mediated persistent AF in the isolated canine coronary-perfused right atria.

|  | $APD_{90}$ (ms) | ERP (ms) | Shortest $S_1$-$S_1$ | Induction of Persistent AF |
|---|---|---|---|---|
| Control | 198 ± 7 | 153 ± 8 | 130 ± 10 | 0% |
| Ranolazine (5 μM) | 210 ± 10* | 181 ± 11* | 201 ± 22* | 0% |

TABLE 1-continued

Effects of ranolazine (5 μM), dronedarone (10 μM), and their combination on atrial excitability and the induction of ACh-mediated persistent AF in the isolated canine coronary-perfused right atria.

| | $APD_{90}$ (ms) | ERP (ms) | Shortest $S_1$-$S_1$ | Induction of Persistent AF |
|---|---|---|---|---|
| Dronedarone (10 μM) | 202 ± 9 | 171 ± 11* | 147 ± 11* | 0% |
| Ranolazine + Dronedarone | 212 ± 11 | 211 ± 16* | 239 ± 21 | 0% |
| ACh (1 μM) | 41 ± 6 | 52 ± 9 | 56 ± 7 | 100% (10/10) |
| Ranolazine (5 μM) + ACh | 52 ± 6† | 72 ± 13† | 94 ± 11† | 71% (5/7) |
| Dronedarone (10 μM) ACh + | 45 ± 5 | 59 ± 7 | 88 ± 13† | 83% (5/6) |
| Ranolazine + Dronedarone + ACh | 67 ± 14†‡ | 99 ± 18†‡ | 120 ± 24†‡ | 11% (1/9) |

Action potential duration (APD) and effective refractory period (ERP) data presented were obtained from the pectinate muscle region of coronary-perfused atria at a CL of 500 ms (n = 5-15).
*<0.05 versus control;
†P < 0.05 versus acetylcholine alone (ACh, 1.0 μM).
‡P < 0.05 versus Ranolazine + ACh and Dronedarone + ACh.
Shortest ($S_1$-$S_1$ = the shortest CL permitting 1:1 activation (at 2x threshold stimulus intensity determined at a cycle length of 500 ms).

TABLE 2

Effects of ranolazine (5 μM), dronedarone (10 μM), and their combination to terminate persistent ACh-mediated AF and prevent its re-induction in the isolated canine coronary-perfused right atria.

| | Termination Persistent AF | Prevention of AF re-induction |
|---|---|---|
| ACh (1 μM) | 0% 0/10 | — |
| ACh + Ranolazine (5 μM) | 20% (1/5) | 100% (1/1) |
| ACh + Dronedarone (10 μM) | 17% (1/6) | 0% (0/1) |
| ACh + Ranolazine + Dronedarone | 60% (6/10) | 100% (6/6) |

Superfused Pulmonary Veins

Figure 9:
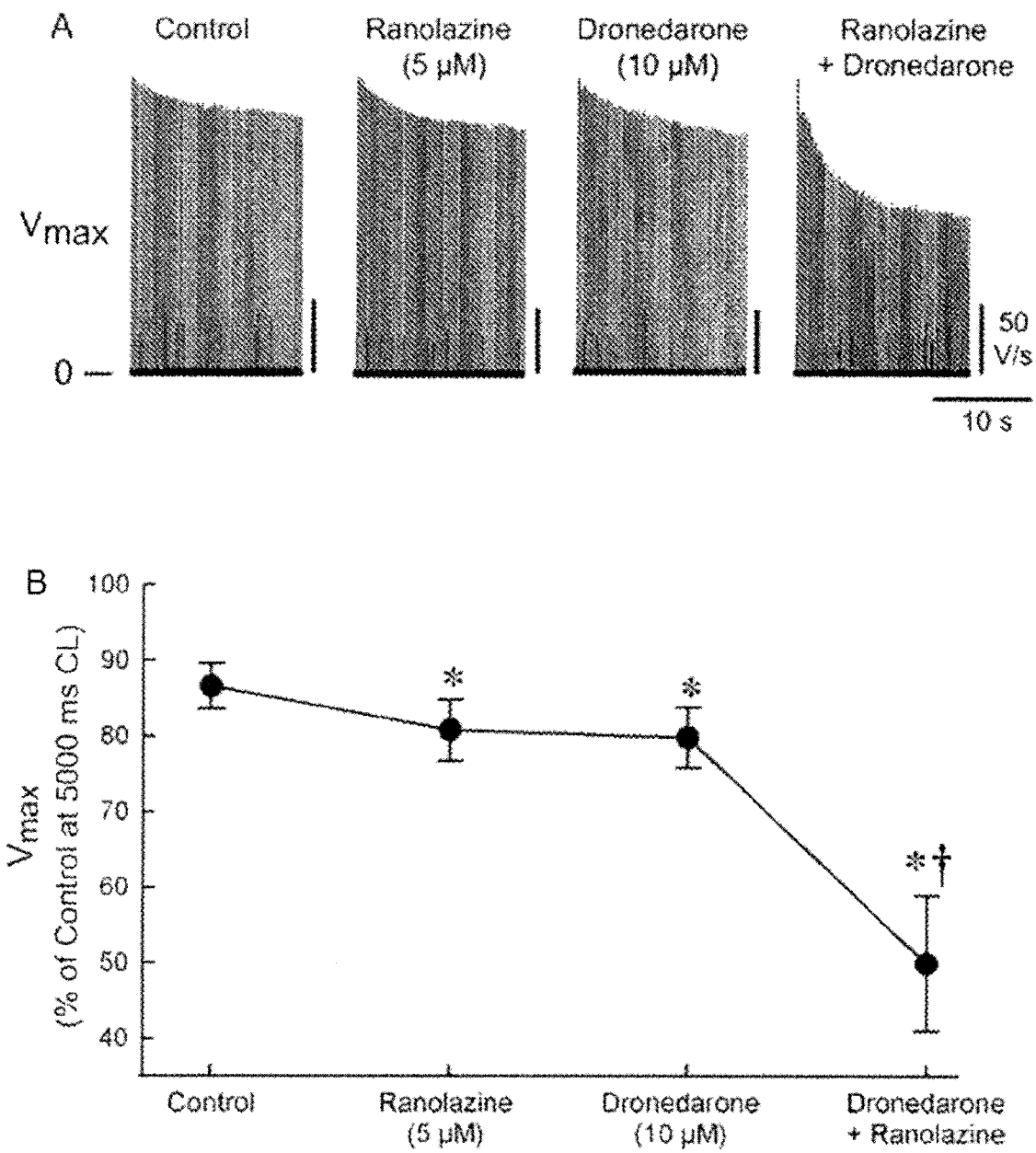
FIG. 9: Synergistic effect of the combination of ranolazine and dronedarone on $V_{max}$ following an abrupt change in rate in pulmonary vein (PV) sleeve preparations. A: $V_{max}$ traces recorded following a change in cycle length (CL) from 5000 to 300 ms B: Graph displaying composite data of $V_{max}$ changes. A change or rate from CL 5000 to 300 ms induces a 13% reduction in $V_{max}$ under control conditions and a 19, 20 and 50% reduction following ranolazine (5 μM) or dronedarone (10 μM) alone or combined, respectively. * p<0.05 vs Control. # p<0.05 vs Ranolazine or Dronedarone alone.

FIG. 9 illustrates the synergistic effect of combined ranolazine and dronedarone on $V_{max}$ following an abrupt change in rate of pacing of PV sleeves preparations. Panel A displays $V_{max}$ traces following a change in basic cycle length (BCL) from 5000 to 300 ms and panel B shows composite data of $V_{max}$ changes. A change of rate from CL of 5000 to 300 ms induced a 13% reduction in $V_{max}$ under control conditions and a 19, 20 and 50% reduction following ranolazine (5 μM) or dronedarone (10 μM) alone or combined, respectively.

Figure 10:
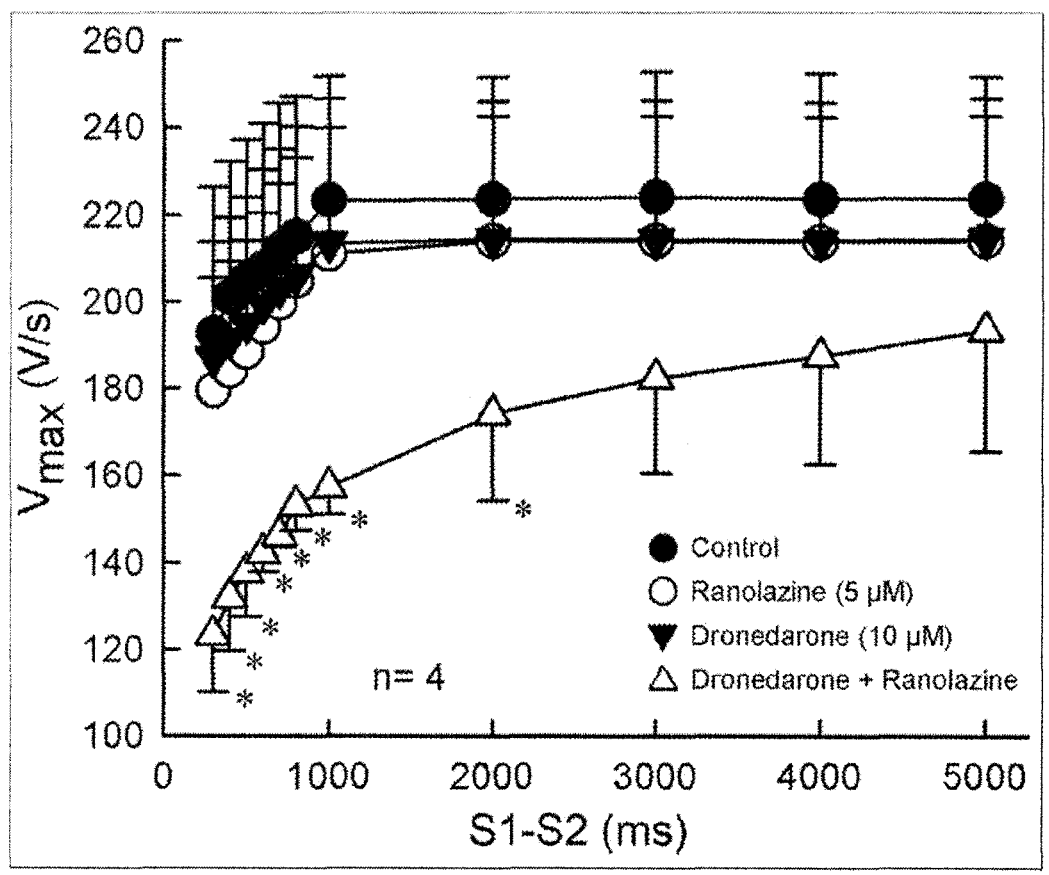
FIG. 10. Rate of recovery of the sodium channel from block by ranolazine (5 μM), dronedarone (10 μM) and their combination in PV sleeve preparations. n=4. Shown are the $V_{max}$ values as a function of S1-S2 at an S1-S1 of 300 ms. Recovery from block is markedly slowed following block with the drug combination, compared to ranolazine or dronedarone alone.* p<0.05 versus Control, Ranolazine alone and Dronedarone alone.
Figure 11:
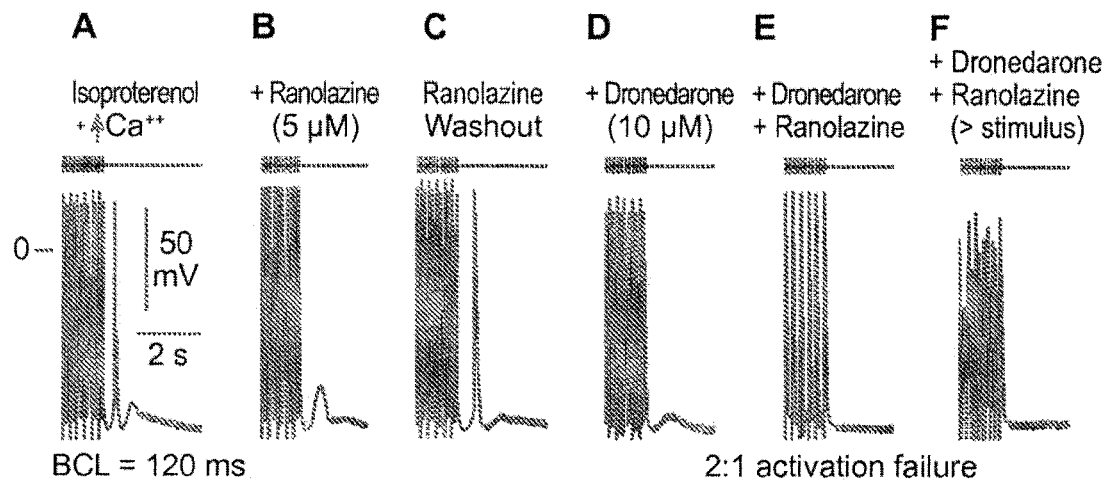
FIG. 11: Combination of ranolazine (5 μM) and dronedarone (10 μM) abolishes delayed afterdepolarization (DAD)-induced triggered activity in a PV sleeve preparation. A: Isoproterenol (1 μM) and high calcium (5.4 mM)-induced a triggered response followed by a DAD. B: Ranolazine (5 μM) eliminates the triggered beat but a prominent DAD persists. C: Washout of ranolazine restores triggered response followed by a DAD. D: Dronedarone (10 μM) eliminates the triggered response but a DAD persists. E: Combination of ranolazine and dronedarone abolishes all DAD and triggered activity and induces 2:1 activation failure. F: In the continued presence of the drug combination, an increase of stimulus intensity restores 1:1 activation, but not DAD activity. Basic cycle length (BCL)=120 ms.
Figure 12:
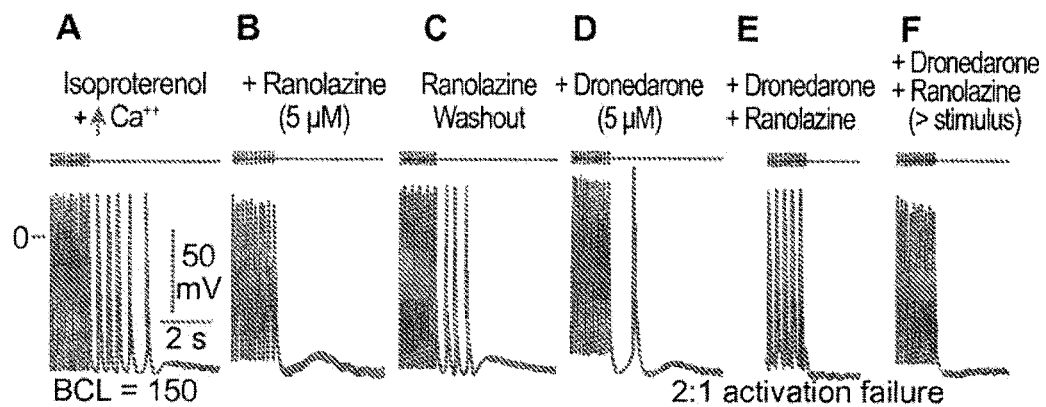
FIG. 12: Combination of ranolazine (5 μM) and dronedarone (5 μM) eliminates DAD-induced triggered activity in a PV sleeve preparation. A: Isoproterenol (1 μM) and high calcium (5.4 mM) give rise to DAD-induced triggered activity. B: Ranolazine (5 μM) eliminates triggered beats but a DAD persists. C: Washout of ranolazine restores triggered activity. D. Dronedarone (5 μM) reduces the number of triggered responses. A single triggered beat followed by a DAD persists. E: Combination of dronedarone and ranolazine abolishes all DAD and triggered activity, and induces 2:1 activation failure. F: In the continued presence of the drug combination, an increase of stimulus intensity restores 1:1 activation, but not DAD activity. Basic cycle length (BCL) =150 ms.

FIG. 10 illustrates the effect of ranolazine and dronedarone alone and in combination on the rate of recovery of $V_{max}$, reflecting unblocking of drug from the sodium channel, in PV sleeve preparations. The graph displays $V_{max}$ as a function of S1-S2 at a CL of 300 ms. Exposure of the preparation to combined dronedarone and ranolazine resulted in a much greater reduction of $V_{max}$ and a much slower recovery than ranolazine or dronedarone alone.

At a CL of 300 ms, ranolazine (5 μM) and dronedarone (10 μM) alone caused no significant changes in the diastolic threshold of excitation (DTE). DTE increased from 0.21±0.07 to 0.24±0.09 mA and 0.26±0.09 mA (n.s) following addition of ranolazine and dronedarone, respectively. The combination of ranolazine and dronedarone caused a significant increase in DTE from 0.21±0.07 to 0.53±0.11 mA. (p<0.05, n=4).

In PV sleeve preparations, the shortest pacing CL permitting a 1:1 response was 116±8 ms in untreated controls, 121±13 ms with ranolazine (5 μM), 120±12 ms after dronedarone (10 uM) and 200±67 ms after combined ranolazine and dronedarone (p<0.05, n=4). Thus, the combination of ranolazine and dronedarone reduced excitability and induced a synergistic increase in the CL permitting 1:1 activation in PV sleeves.

Previous studies have shown that ranolazine (10 μM) alone suppresses late phase 3 early afterdepolarizations (EADs), delayed afterdepolarizations (DADs) and triggered activity elicited by exposure of the PV sleeves to ACh, isoproterenol, or high [Ca2+]o+rapid pacing11. In the present study, DADs and triggered activity induced following a 20 beats train of rapid pacing rates plus isoproterenol and/or high calcium were reduced by ranolazine (5 μM) or dronedarone (10 μM) alone but abolished by exposure to a combination of ranolazine and dronedarone (FIG. 11-12) (n=6).

Discussion

Our data demonstrate a potent atrial-selective effect of the combination of dronedarone (10 μM) and ranolazine (5 μM) to depress sodium channel-dependent parameters and to suppress AF and triggered activity in experimental models of AF. When dronedarone (10 μM) or ranolazine (5 μM) were used alone, the electrophysiological changes in both atria and ventricles were either small or absent and their anti-AF efficacy was low. Considering the excellent safety profile of both agents, our results suggest that the synergistic atrial-selective action of ranolazine and dronedarone may offer a unique combination therapy for AF that is both safe and effective.

Mechanisms Contributing to the Development and Maintenance of Atrial Fibrillation The initiation of AF involves the development of both a trigger and a substrate. It is well established that the PV muscular sleeves are often the source of extrasystoles responsible for the initiation of paroxysmal AF.[26] Ectopic activity that serves as a trigger for AF can develop as a result of reentry, DAD-induced or late phase 3 EAD-induced triggered activity.[11,27] A principal substrate for the initiation of reentry involves a reduction in wavelength, secondary to an abbreviation of ERP. The maintenance of AF is facilitated by both electrical and structural remodeling. The electrical remodeling involves a further abbreviation of ERP caused by abbreviation of the atrial action potential.[28] The pharmacological approach to the management of AF therefore targets mechanisms capable of prolonging ERP.[29] The present study presents evidence of a potent effect of the combination of ranolazine and dronedarone to eliminate both the trigger and substrate associated with the initiation and maintenance of AF.

Electrophysiology and Antiarrhythmic Efficacy of Dronedarone

Acute dronedarone has been reported to produce variable but generally small or no effect to alter APD.[30-34] APD was not altered in superfused ventricular preparations isolated from canine and guinea pig hearts at concentration up to 10 μM dronedarone.[30,31] In canine left ventricular superfused tissue slice preparations, a high concentration dronedarone (30 μM) caused either no (at a CL of 300-800 ms) or slight abbreviation of $APD_{90}$ (7% abbreviation in M cell preparations at a CL of 2000 ms).[34] In rabbit superfused cardiac preparations, acute dronedarone prolonged APD in ventricles, but abbreviated it in atria.[32] Thus, our data on the effect of acute dronedarone APD (FIG. 1) are generally consistent with those reported previously.

Ventricular and atrial ERP have been reported to be prolonged by up to 23% following acute dronedarone in in vivo dogs and the extent of ERP prolongation in both chambers was similar.[35] In dog with chronic AV block in vivo, dronedarone did not change ventricular ERP.[36] In our current in vitro investigation, dronedarone prolonged both atrial and ventricular ERP, with preferential lengthening in atria (by 9 and 4%, respectively). ERP prolongation by dronedarone in the ventricles but not in the atria was associated by a comparable $APD_{90}$ lengthening (FIG. 2). Thus the increase of ERP in atria, but not in ventricles, is due to the development of PPR. Dronedarone therefore produces a atrial-selective effect to prolong ERP.

Acute dronedarone (10 μM) has been reported to produce a relatively small reduction in $V_{max}$ in both atrial and ventricular rabbit superfused preparations (CL of 1000 ms).[33] Even at rapid pacing rates (CL of 125 ms), 10 μM dronedarone reduced $V_{max}$ by only 16% in superfused rabbit atrial preparations.[33] Dronedarone (10 μM) depressed $V_{max}$ by 14% in superfused guinea pig papillary muscles (at a CL of 1000 ms).[31] In canine ventricular muscle and Purkinje fiber superfused preparations, acute exposure to dronedarone (10 μM) did not reduce $V_{max}$ significantly (also at a CL of 1000 ms).[30] Thus, the relative modest effect of acute dronedarone on $V_{max}$ observed in our study is consistent with those previously reported.

Interestingly, while several clinical investigations have shown anti-AF efficacy of dronedarone for the long term maintenance of sinus rhythm,[4,5] we could not find any full-length publications evaluating the efficacy of dronedarone against AF in any experimental model (acutely or chronically). We are also not aware of any clinical study testing the anti-AF ability of acute dronedarone. Thus, we are unable to compare our results of the relatively weak actions of acute dronedarone to suppress AF with any previous preclinical or clinical study. Acute dronedarone has been shown to effectively suppress ventricular arrhythmias related to ischemia/reperfusion[37] and long QT syndrome[36] in animal models.

Available clinical data indicate that the long-term efficacy of dronedarone for the maintenance of sinus rhythm in AF patients is inferior to that of amiodarone.[2,3] In the DIONYSOS trial direct comparison between amiodarone and dronedarone, showed that the rate of recurrence of AF was 63% with dronedarone and 42% with amiodarone (at 6 months of follow-up). In the combined EURIDIS and ADONIS trials, AF recurrence occurred in 64% of patients treated with dronedarone compared to 75% of patients taking placebo at 1 year follow up.[5] Data relative to the effect of dronedarone to convert AF to sinus rhythm are relatively scarce. The rate of conversion of persistent AF with dronedarone ranged from 5.8 to 14.8% (800-1600 mg/day) compared to 3.1% in the placebo arm, as determined on the 5-7th days after the start of drug treatment.[4] The relatively weak actions of acute dronedarone to suppress AF in the present study are consistent with the very modest effects on the drug on AF in the clinic. The marked potentiation of the effect of dronedarone to suppress AF and prevent its induction when combined with ranolazine in our experimental model bodes well for a similar potentiation in the clinic.

We observed fairly mild atrial-selective effects of dronedarone to suppress sodium-channel-dependent parameters, including $V_{max}$, DTE, ERP, conduction time, and the shortest $S_1$-$S_1$ permitting 1:1 activation. This is in contrast to chronic amiodarone, which causes marked atrial-selective electrophysiological effects.[10,12] It is noteworthy that while major differences in cardiac electrophysiological effects have been noted for acute versus chronic amiodarone, this does not appear to be the case for acute versus chronic dronedarone.[30,38] This is likely due in part to a much faster half-life of elimination of dronedarone than amiodarone (about 24 hours versus months).[38]

Electrophysiology and Antiarrhythmic Efficacy of Ranolazine

We have previously reported that 5 μM of ranolazine elicits moderate electrophysiological effects in canine atrial preparations, with little to no effect in ventricular preparations.[9,15] This concentration of ranolazine is well within the therapeutic range of the drug (2-10 μM). These findings are confirmed in the current study. $APD_{90}$ was slightly, but statistically significantly, prolonged by 5 μM ranolazine in atria, with no changes in the ventricles at a CL of 500 ms.[9] Sodium channel-dependent parameters were modestly depressed by ranolazine (5 μM) in atria, with practically no change in the ventricles. Ranolazine has also been shown to cause atrial-predominant prolongation of ERP in in vivo pigs.[13]

The anti-AF efficacy of 5 μM ranolazine was not tested in the ACh-mediated AF model in our previous studies. Higher concentrations of ranolazine, at the upper end of the therapeutic range, were shown to exert potent anti-AF effects in experimental models of vagally-mediated AF in canine atria in vitro (at 10 μM)[9] and porcine atria in vivo (~9 μM plasma concentration)[13] models. In an ischemia-reperfusion-isoproterenol model of AF, 5 μM ranolazine was observed to prevent the induction of AF in 60% of atrial preparations.[9] In superfused pulmonary vein preparations 10 μM ranolazine effectively suppressed intracellular calcium-dependent DAD and late phase 3 EAD-induced triggered activity.[11] Ranolazine has also been shown to reduce the onset of new AF and to terminate AF in patients.[39-41] A recent study indicates that a single high dose (2000 mg) of ranolazine used as a "pill-in-the-pocket" approach, was effective in terminating AF in 13 of 18 patients with paroxysmal AF and structural heart disease.[41] No adverse effects other than constipation were noted. The 72% conversion rate is comparable to other reported "pill in the pocket" approaches, suggesting that a high oral dose of ranolazine may have utility as a safe agent to convert new or paroxysmal AF.[41]

Drug Combination for Antiarrhythmic Therapy

Efficacy and Safety

We hypothesized that a combination of open and inactivated-state sodium channel block could produce a synergistic atrial-selective sodium channel inhibition, and, thus, be effective against AF, without eliciting significant electrophysiological effects in the ventricles. Following validation of this hypothesis,[14] we considered the combination of dronedarone and ranolazine, in that dronedarone is a congener of amiodarone and has a similar electrophysiological profile.[38] The results discussed herein provide validation of this concept as well, presenting further evidence in support of the hypothesis that a combination of predominantly open and inactivated-state blockers of the sodium channel can lead to synergistic effects to selectively inhibit $I_{Na}$-dependent parameters and thus exert potent atrial-selective actions to terminate and prevent the induction and re-induction of AF (Table 1).

A major concern in the pharmacologic management of AF agents is the risk for induction of ventricular arrhythmias and/or organ toxicity.[21] Sodium channel blockers are known to induce malignant ventricular arrhythmias particularly in patients with structural heart diseases (such as congestive heart failure, myocardial infarction, hypertrophy, etc). $I_{Kr}$-blockers are known to induce polymorphic ventricular tachycardia, known as Torsade de Pointes (TdP). Amiodarone is generally considered the best choice for the long-term maintenance of sinus rhythm following AF cardioversion. While amiodarone only rarely produces ventricular pro-arrhythmias and is generally safe in patients with structurally-compromised ventricles, it causes extracardiac complications (up to 15% in the first year of treatment and up to 50% with longer term treatment[42]). The iodine moiety in the amiodarone molecule is believed to be largely responsible for these adverse effects. Dronedarone, a non-iodinated derivative of amiodarone, was designed with the intention to reduce the risk of extracardiac toxicity of amiodarone. Dronedarone is generally considered to be safer compared to amiodarone in AF patients.[3] However, in patients with preexisting severe congestive heart failure (New York Heart Association (NYHA) Class III and IV), dronedarone worsens heart failure symptoms, leading to increased mortality.[7] It is noteworthy that amiodarone also increases mortality in patients with advanced heart failure (NYHA Class IV).[43] The clinical usefulness of dronedarone is not limited to its anti-AF efficacy. Dronedarone has been shown to reduce the incidence of stroke and to possess rate-control properties in AF patients.[6,44]

Clinical use of ranolazine, both acute and long-term, has not been associated with serious adverse effects, not even in patients with structural heart disease.[45,46] The rationale for combining dronedarone and ranolazine stems from the superiority of dronedarone over amiodarone with respect to safety.[3,5] Like the combination of amiodarone and ranolazine,[14] the combination of dronedarone and ranolazine produces potent atrial-selective anti-AF effects, but is likely to be associated with less adverse effects.

The dronedarone and ranolazine combination was more effective in preventing AF initiation than in terminating AF (see Tables 1 and 2). This appears to be the case with most anti-AF agents in both experimental and clinical settings, including ranolazine[9] and dronedarone.[4]

Conclusion

In canine cardiac preparations, a combination of dronedarone and ranolazine causes potent atrial-selective inhibition of sodium channel-dependent parameters, effectively suppressing atrial arrhythmias at concentrations causing little to no change of electrophysiologic parameters in the ventricles. These experimental data coupled with the clinical safety data available for the individual drugs, suggest that clinical studies specifically designed to evaluate the potential effectiveness and safety of this combination therapy are warranted.

Example 2

Part 1. Synergistic Chronotropic and Dromotropic Effects of Dronedarone and Ranolazine in Guinea Pig Isolated Hearts Anesthesia Guinea pigs (Hartley) of either sex weighing 300-350 g were anesthetized by inhalation of isoflurane.

Guinea Pig Heart Isolation

The chest of a guinea pig was cut open, and the heart was quickly removed and rinsed in ice-cold modified Krebs-Henseleit (K-H) solution. The contents of the modified K-H solution were (in mM) 117.9 NaCl, 4.8 KCl, 2.5 $CaCl_2$, 1.18 $MgSO_4$, 1.2 $KH_2PO_4$, 0.5 $Na_2$ EDTA, 0.14 ascorbic acid, 5.5 dextrose, 2.0 pyruvic acid (sodium salt), and 25 $NaHCO_3$. The K-H solution was continuously gassed with 95% $O_2$-5% $CO_2$, and the pH was adjusted to a value of 7.4.

Isolated Heart Perfusion

To perfuse the heart by the Langendorff method, the transected aorta was slid onto a glass cannula and secured by a ligature. Retrograde perfusion of the aorta was initiated immediately at a constant flow of 10 ml/min with modified K-H solution warmed to 37.0±0.5° C. A side port in the cannula was used to connect the perfusion line to a pressure transducer (AD Instruments, Australia) for measurement of coronary perfusion pressure (CPP). To facilitate the exit of fluid from the left ventricle, the leaflets of the mitral valve were trimmed with fine spring-handled scissors. Hearts were allowed to beat spontaneously in experiments to measure heart rate, or paced at a constant rate using external electrodes, in experiments to measure AV conduction time. After completion of dissection and instrumentation, heart rate or stimulus-to-His bundle (S-H) interval and CPP were monitored continuously. Each heart was allowed to equilibrate for 20-40 min before the administration of drug. Experimental interventions were always preceded and followed by control measurements.

Exclusion Criteria

Criteria for the exclusion of hearts from the study were: 1) absence of a stable CPP of 50 mm Hg or above, 2) inability to get a stable spontaneous heart rate (for heart rate measurement) or inability to pace a heart at a constant rate (for S-H interval measurement), and 3) heart deterioration during an experiment (as indicated by a>25% difference between pre- and post-drug control values of a measured parameter such as CPP). To maintain the heart in a suitable condition to respond to drug, the total duration of an experiment was limited to 2 hours. CPP was continuously monitored and recorded throughout each experiment using a Power Lab acquisition system (AD Instruments, Australia) connected to a computer. An increase of CPP suggests either drug precipitation with occlusion of small vessels, drug-induced vasoconstriction, or ischemia-induced contracture of the myocardium, whereas a decrease of CPP suggests either drug-induced contracture of the myocardium, whereas a decrease of CPP suggests either drug-induced vasodilation or damage to vessels during instrumentation of the heart. No effect of drug on CPP was noted in these studies.

Measurement of Cardiac Electrical Activity

Spontaneous Heart Rate Measurement

To measure the effect of drug on spontaneous atrial rate, the atria of each heart was left intact rather than excised. A unipolar Teflon-coated electrode was placed on the right atrium to record the atrial depolarization. Spontaneous heart rate was recorded continuously throughout an experiment before (control) and during exposures to increasingly higher concentration of dronedarone and ranolazine. The average of 1 min heart rate in the absence (control) and presence of each concentration of drug was calculated and plotted.

S-H Interval

To facilitate the recording of a drug effect on the S-H interval, parts of the left and right atrial tissues, including the region of the sinoatrial node, were removed, both to decrease the spontaneous heart rate and to expose the atrial septum for electrode placement. A bipolar Teflon-coated electrode was placed in the wall of the intra-atrial septum to pace the heart. Hearts were electrically paced at a fixed rate of 3.2 Hz. Stimuli were provided by a stimulation generator (model 48, Grass Instruments, W. Warwick, R.I.) and delivered to the heart through a stimulus isolation unit as square wave pulses of 3 ms duration and at least twice the threshold intensity.

A His bundle electrogram was recorded using a Teflon-coated unipolar electrode placed in the right side of the interatrial septum adjacent to the AV junction. The signal was displayed continuously in real time on an oscilloscope screen (Tektronix Inc., Beaverton, Oreg.) at a sweep speed of 10 ms/cm and on a computer monitor. The duration of time from the first pacing artifact to the maximum upward deflection of the His bundle signal was used as the S-H interval.

Experimental Protocol for Isolated, Perfused Heart Experiments

At the beginning of an experiment, a heart was perfused with saline until either the heart rate or the S-H interval, and the CPP remained constant for at least 5-10 minutes.

Dronedarone (Dron), ranolazine or the combination at various concentrations was infused to the hearts. Each concentration of Dron was infused for about 20 min to allow a steady-state response to be recorded, whereas each concentration of ranolazine (Ran) was infused for 10 min to allow a steady-state response to be recorded. Then drug administration was discontinued and saline administration was initiated to begin drug washout

Measurement of the Amplitude of the Delayed After-Depolarizations (DADs) Induced by Isoproterenol in Single Myocytes Isolated from the Guinea Pig Left Ventricle Myocytes were isolated from guinea pig hearts by collagenase digestion. Myocyte action potentials were recorded using the patch clamp technique in current clamp mode. Action potentials were stimulated using a train of 8 depolarizing pulses at a frequency of 1 Hz, applied every 10 sec. DADs were elicited by perfusion of myocytes with 50 nM isoproterenol (ISO). The amplitudes of DADs were measured electronically. To determine if a drug treatment was able to reduce the amplitude of DADs in the presence of ISO, test article (either ranolazine, dronedarone, or the combination) was added to the myocyte perfusion bath in the continued presence of ISO.

Part 2. Efficacy and Safety of Dronedarone and Ranolazine Alone and in Combination, in Female Rabbit Isolated Hearts

Experimental Preparation

Each rabbit was sedated using intramuscular injections of 6 mg/kg xylazine and 40 mg/kg ketamine and then anesthetized using a "cocktail" of ketamine (15 mg/kg)+xylazine (4 mg/kg) in 1.5 ml saline. The ketamine/xylazine cocktail was administered as an i.v. bolus via the marginal ear vein. After anesthesia was confirmed, the thorax was opened and the heart was quickly excised. The heart was placed in a modified Krebs-Henseleit (K-H) physiological saline solution at room temperature. The K-H solution contained (in mmol/L): NaCl 118, KCl 2.8, $KH_2PO_4$ 1.2, $CaCl_2$ 2.5, $MgSO_4$ 0.5, pyruvate 2.0, glucose 5.5, $Na_2EDTA$ 0.57 and $NaHCO_3$ 25. The solution was continuously gassed with 95% $O_2$ and 5% $CO_2$, and its pH was adjusted to 7.4. The aorta was rapidly catheterized and the heart was perfused by the method of Langendorff with K-H solution warmed to 36-36.5° C. at a rate of 20 mL/min with a roller pump (Gilson Minipuls3, Middleton, Wis.). CPP was measured (with a Biopac MP 150 pressure transducer, Goleta, Calif.) from a side port of the aortic catheter. To facilitate exit of fluid from the chamber of the left ventricle (LV), the leaflets of the mitral valve were trimmed with fine spring-handled scissors. The right atrial wall was partially removed.

Complete AV block was induced by themo-ablation of the AV nodal area. The spontaneous ventricular rate (i.e., the ventricular escape rhythm) was a few beats per minute after successful AV nodal ablation. A bipolar Teflon-coated electrode was placed on the right ventricular septum to pace the heart. Electrical stimuli 3 ms in width and 3-fold threshold amplitude were delivered to the pacing electrode at a frequency of 1 Hz throughout the experiments using a Grass S48 stimulator (W. Warwick, R.I.).

After initiation of ventricular pacing, a 30-40 min equilibration delay was allowed for heart rate (and CPP) to achieve a steady state, an essential experimental condition for recording a good quality monophasic action potential (MAP) recording. The total duration of the experimental protocol was limited to 2.5 h, the time during which the preparation exhibited good stability.

Signal Recording and Processing

Monophasic action potential (MAP) and ECG electrodes from Harvard Apparatus Inc. (Holliston, Mass.) were used to record heart rate (in beats per minute, or bpm), left ventricular MAPs and a bipolar ECG MAP electrodes were pressure contact Ag—AgCl cells attached to a circular holder with springs to keep the electroides in contact with the LV epicardial surface. Two MAP electrodes were placed on the epicardial ventricular free wall below the level of the atrial-ventricular valves, one at the base to record a basal MAP and one at the apex to record an apical MAP. Electrode signals were amplified and displayed on an oscilloscope for visual monitoring throughout the experiments. To ensure that each response to drug had achieved a steady state before a drug concentration was changed, the MAP duration (from onset of depolarization to 100% repolarization) was measured using an on-screen caliper throughout each drug infusion period.

Signals were saved on a computer hard disk for subsequent analysis. Bipolar electrocardiograms (ECG) were generated using an isolated-heart ECG apparatus (Harvard Apparatus, Holliston, Mass.) attached to Biopac amplifier system. Coronary perfusion pressure was measured using a pressure transducer (Biopac or PowerLab pressure measuring system. MAPs, ECGs, and CPP signals were appropriately amplified, filtered, sampled, digitized in real time (using a Biopac MP 150, Goleta, Calif.), and displayed on a computer screen. All signals were saved on a computer hard disk for subsequent analysis.

Original MAP profiles were superimposed to get an average signal and then transferred into Spike-II (Cambridge Electronic Design, GB) software to measure the duration of the MAP at the level at which repolarization was 90% completed (i.e., the value of $MAPD_{90}$).

Exclusion Criteria for Rabbit Isolated Heart Studies

Any of the following problems were cause for excluding a preparation from study: (1) unstable CPP or heart rate; (2) persistent premature ventricular complexes (PVCs) or ventricular tachycardia after AV nodal ablation; (3) macroscopic anatomical damage to the heart; or (4) MAP signal instability. Approximately 10% of all preparations were excluded.

Statistical Analyses

Data were plotted and analyzed using Prism version 5 (Graph Pad Software, San Diego, Calif.) and expressed as mean±SEM. The significance of differences of measures before and after interventions in the same hearts was determined by repeated measure one-way analysis of variance (ANOVA) followed by Student-Newman-Kaul's test. When treatment values were obtained at different rates from different groups of hearts, two-way ANOVA of repeated measures was used. A paired or un-paired student t test was used to determine the statistical difference between values of two means obtained from the same or different experiments, respectively.

Results

Effects of Dronedarone, Ranolazine and the Combination on AV Nodal Conduction (S-H Interval) in Guinea Pig Hearts Ranolazine is a weak antagonist of beta-adrenergic receptors (activation of which can increase AV conduction) and a weak voltage- and rate-dependent sodium channel blocker, but has not been shown to alter AV nodal conduction. Dronedarone can decrease the L-type calcium current as well as the sodium current, and these actions may result in a slowing of AV conduction. To determine the effects of both drugs alone and in combination, the duration of the S-H interval (a surrogate for the velocity of electrical impulse conduction through the AV node) was measured in the absence and presence of drug(s). Either dronedarone or ranolazine caused a small slowing of AV conduction without causing second-degree AV block (i.e., dropped beats). As shown in FIG. 13, dronedarone (0.3 µM) or ranolazine (3 µM) caused a small but significant increase in the S-H interval compared to control (no drug) at pacing rate of 3, 4 and 5 Hz (n=14 and 13, p<0.05, FIG. 13A). The greatest effect of the drug combination was observed at the highest pacing rate (i.e., 5 Hz). A combination of dronedarone or ranolazine caused a much greater increase in the S-H interval (n=7, p<0.01 versus control, FIG. 13A). This increase of the S-H interval caused by the combination of ranolazine and dronedarone was significantly greater (p<0.01) than the calculated sum of the individual effects of both drugs (i.e., Σ(R+D), FIG. 13A). The results suggest that the combination of ranolazine and dronedarone may be have a greater effect to slow AV conduction when the atrial rate is high, as in atrial fibrillation. This action may be beneficial to provide control of the ventricular rate during atrial fibrillation.

The combination of ranolazine and dronedarone also decreased the atrial pacing rate at which second-degree block of AV conduction was observed to occur in the isolated heart. The data are expressed as the Wenckebach cycle length associated with second-degree AV nodal conduction block (FIG. 13B). Wenckebach cycle length was significantly increased by the combination of dronedarone and ranolazine (n=7 hearts, p<0.01 versus control (no drug), FIG. 13B). The finding confirms the effect of the drug combination to provide control of the ventricular rate when the atrial rate is increased, as during atrial fibrillation.

Figure 14:
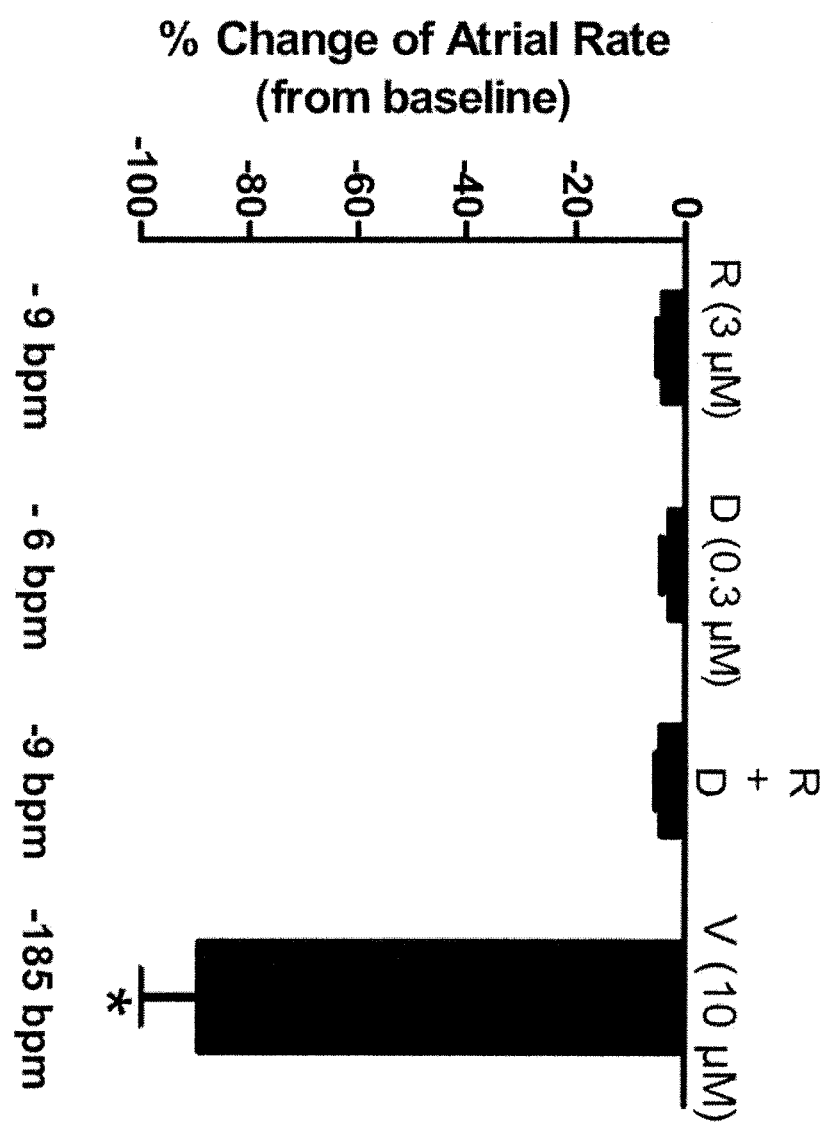
FIG. 14. Effect of dronedarone (D), ranolazine (R), dronedarone plus ranolazine (the combination of R+D) and verapamil (V) on spontaneous (intrinsic) atrial rate (SAR) in guinea pig isolated hearts. Values of the control (no drug) SAR were 225±7 (n=5), 231±6 (n=4), 240±9 (n=5) and 225±3 (n=3) beats/min (or bpm). for R, D, R+D, and V treatment groups, respectively, *, V significantly different from its own control, p<0.01.

Effect of Ranolazine and Dronedarone on Spontaneous Atrial Rate (Negative Chronotropic Effects) in Guinea Pig Hearts The average control atrial rate (n=17 hearts) in the absence of drug was 231±4 bpm (FIG. 14). Ranolazine (Ran or R, 3 µM), dronedarone (Dron or D, 0.3 µM) and the combination of the two caused small but not significant (p>0.05) decreases in the control spontaneous atrial rates recorded from the same hearts (FIG. 14). In contrast, the calcium channel inhibitor verapamil (V, 10 µM) significantly decreased spontaneous atrial rate from 225±3 to 25±24 beats/min (n=3, p<0.01, FIG. 14). The finding suggests that the combination of ranolazine and dronedarone will not decrease the heart rate during sinus rhythm.

Concentration-Response Relationships for Ranolazine and Dronedarone Alone and in Combination to Increase Monophasic Action Potential Duration (MAPD) in Female Rabbit Heart Dronedarone alone caused a small but significant increase in $MAPD_{90}$ (FIG. 15A). Ranolazine (0.1-100 µM) caused much greater increase in $MAPD_{90}$ by 22±6% from 177±10 to 215±6 ms (n=4, p<0.01, FIG. 15B). The sensitivity of the heart to the effect of ranolazine was not increased by dronedarone (FIGS. 15C, 16A). On the contrary, the effects of 6 and 10 µM ranolazine to increase the duration of the ventricular action potential were attenuated by dronedarone in a concentration-dependent manner (FIGS. 15D, 16B). This finding suggests that the combination of dronedarone and ranolazine may cause smaller prolongations of ventricular action potential duration and the QT interval than ranolazine alone. Thus, combining dronedarone with ranolazine may reduce any potential risk associated with prolongation by ranolazine of the QT interval (although prolongation of the QT interval by ranolazine has not yet been shown to be pro-arrhythmic).

Anti-Arrhythmic Effects of Ranolazine and Dronedarone Alone and in Combination in the Rabbit Isolated Heart Treated with E-4031

Figure 18:
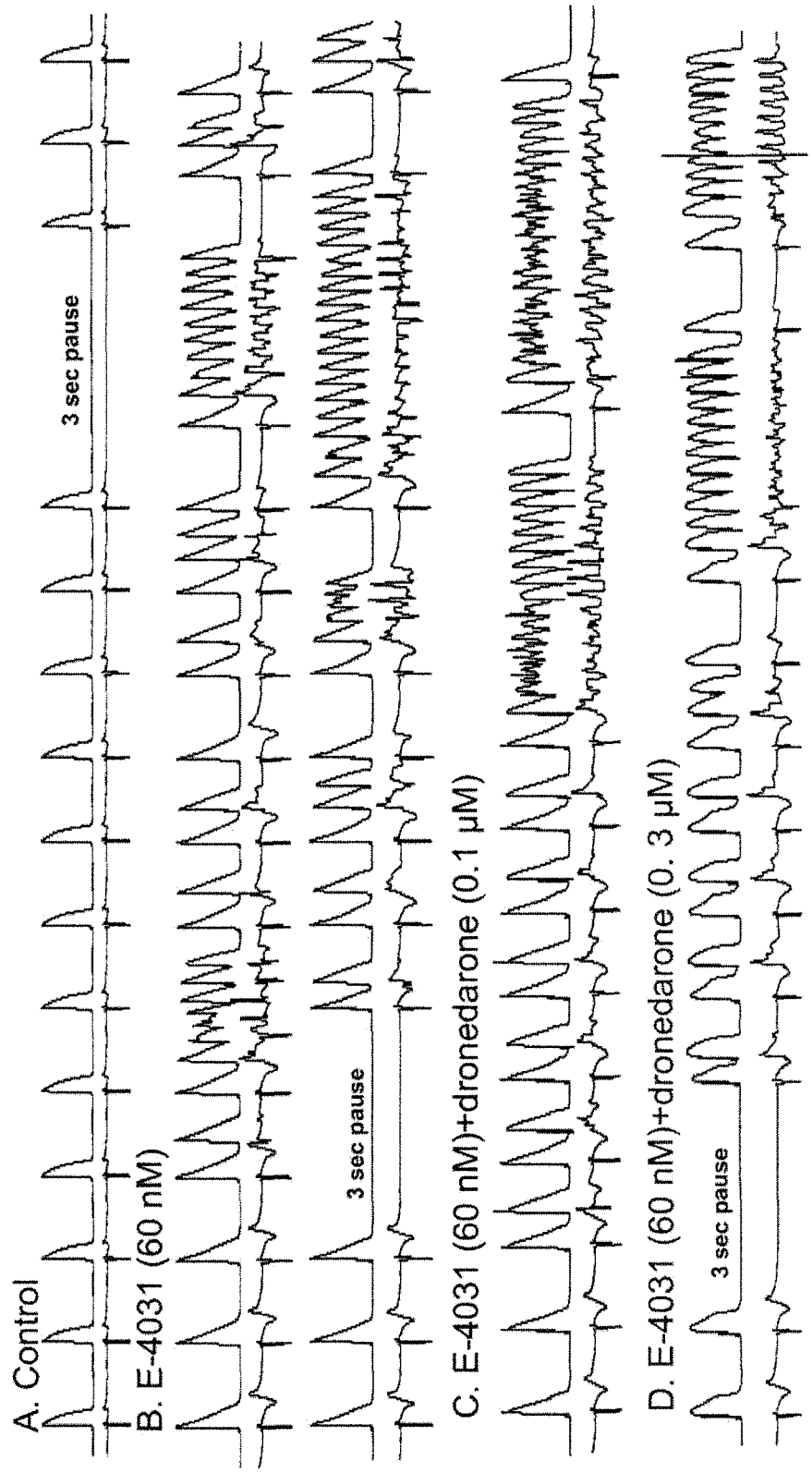
FIG. 18. E-4031 (60 nanomolar (nM)), an $I_{Kr}$ inhibitor, induced spontaneous and 3-sec pause-triggered episodes of TdP. Dronedarone (0.1-0.3 μM) did not terminate the TdP. A: Control; B: E-4031 (60 nM); C: E-4031 (60 nM) and dronedarone (0.1 μM); and D: E-4031 (60 nM) and dronedarone (0.3 μM).
Figure 19:
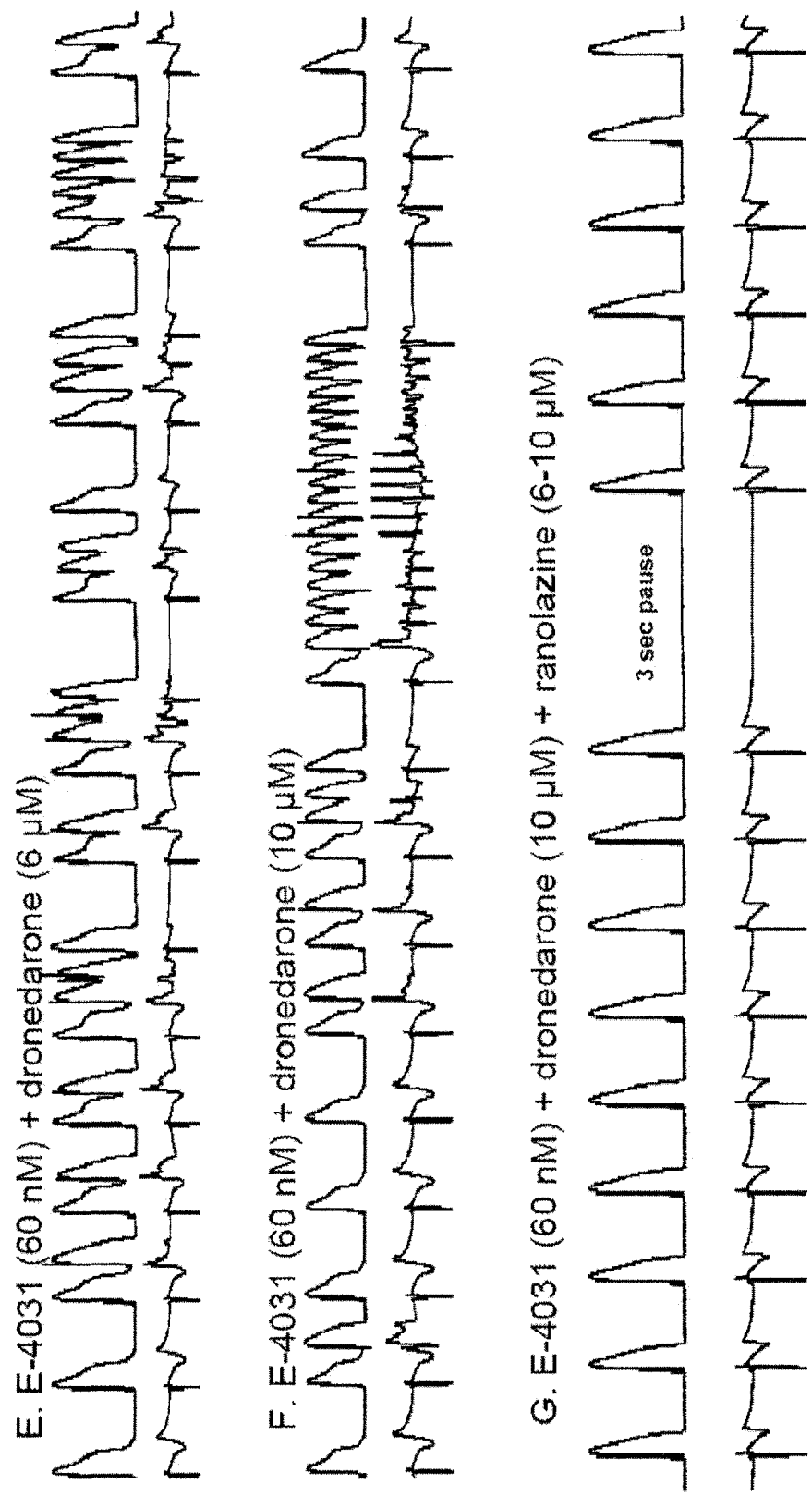
FIG. 19. TdP caused by E-4031 was not terminated by dronedarone (6-10 μM) in this heart. However, TdP was abolished when ranolazine (6-10 μM) was used in combination with dronedarone (10 μM). E: E-4031 (60 nM) and dronedarone (6 μM); F: E-4031 (60 nM) and dronedarone (10 μM); G: E-4031 (60 nM), dronedarone (10 μM), and ranolazine (6-10 μM).
Figure 20:
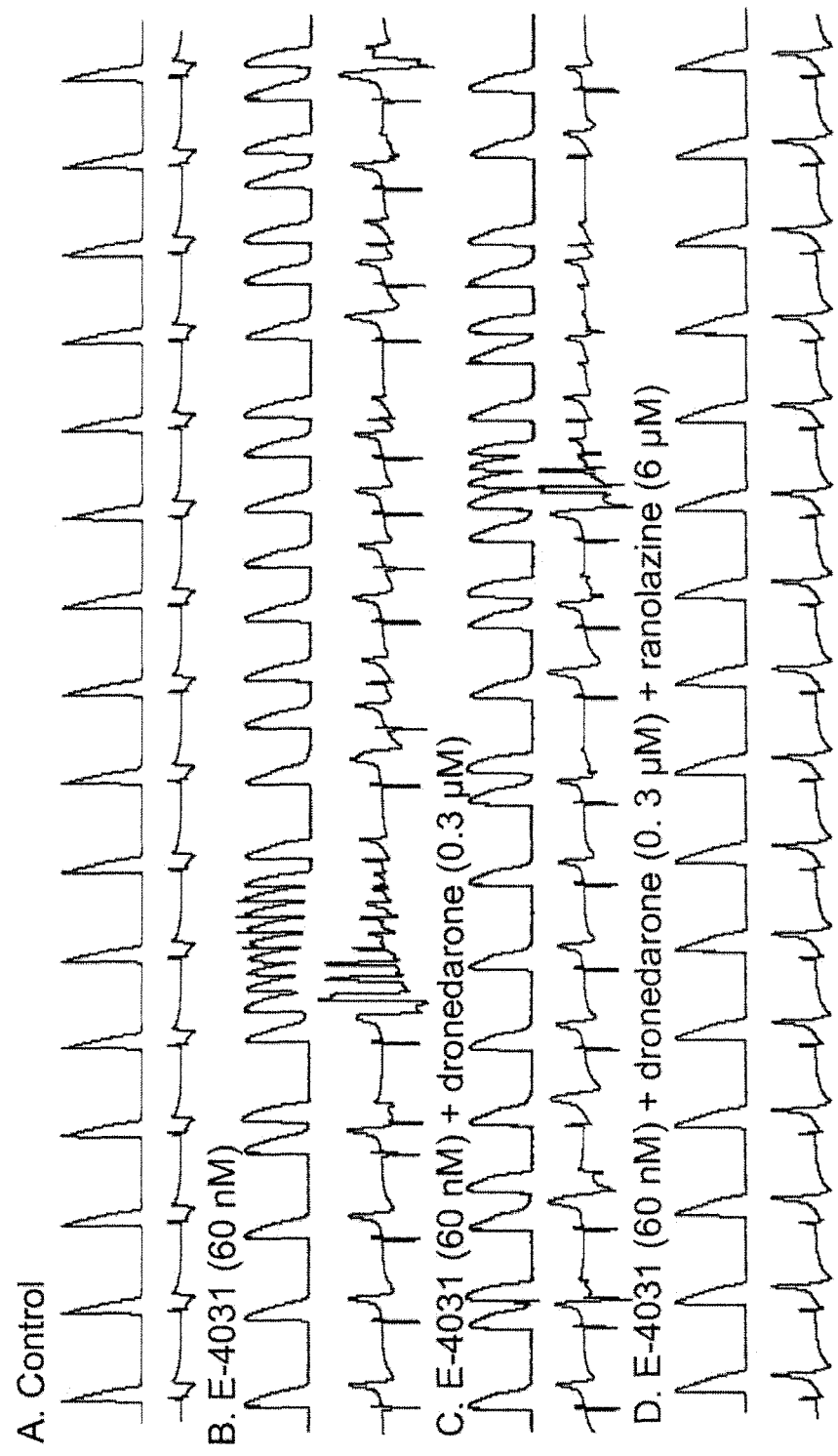
FIG. 20. TdP caused by E-4031 (60 nM) was not terminated by dronedarone (0.3 μM), but was abolished by a combination of ranolazine (6 μM) and dronedarone (0.3 μM). A: Control; B: E-4031 (60 nM); C: E-4031 (60 nM) and dronedarone (0.3 μM); D: E-4031 (60 nM), dronedarone (0.3 μM), and ranolazine (6 μM).

E-4031, an $I_{Kr}$ inhibitor named N-[4-[[1-[2-(6-Methyl-2-pyridinyl)ethyl]-4-piperidinyl]carbonyl]phenyl]methanesulfonamide (available from Tocris Bioscience, Ellisville, Mo.) markedly increased the incidence of torsades de pointes (TdP) ventricular tachycardias (which are not observed in the absence of drug) in female rabbit hearts at a concentration of 60 nM (FIGS. 17-20), and reduced occurrences of early after-depolarizations (EADs; seen in the MAP records as one or more depolarizations before final repolarization of the action potential) in the presence of E-4031 (FIGS. 18-20). Dronedarone (0.3-10 µM) decreased but did not abolish the incidence of TdP (FIG. 17A) and EADs (FIGS. 18C, D and 19F), especially TdP following a 3-sec pause in pacing of the heart (FIG. 18B, D). A combination of dronedarone and ranolazine (6 and 10 µM) further reduced and even abolished episodes of TdP in the presence of 60 nM E-4031 (FIGS. 17, 19, and 20) in hearts that did not respond maximally to dronedarone alone. The findings indicate that a combination of dronedarone and ranolazine is more effective to prevent the induction of TdP ventricular tachycardia than is dronedarone alone.

Figure 21:
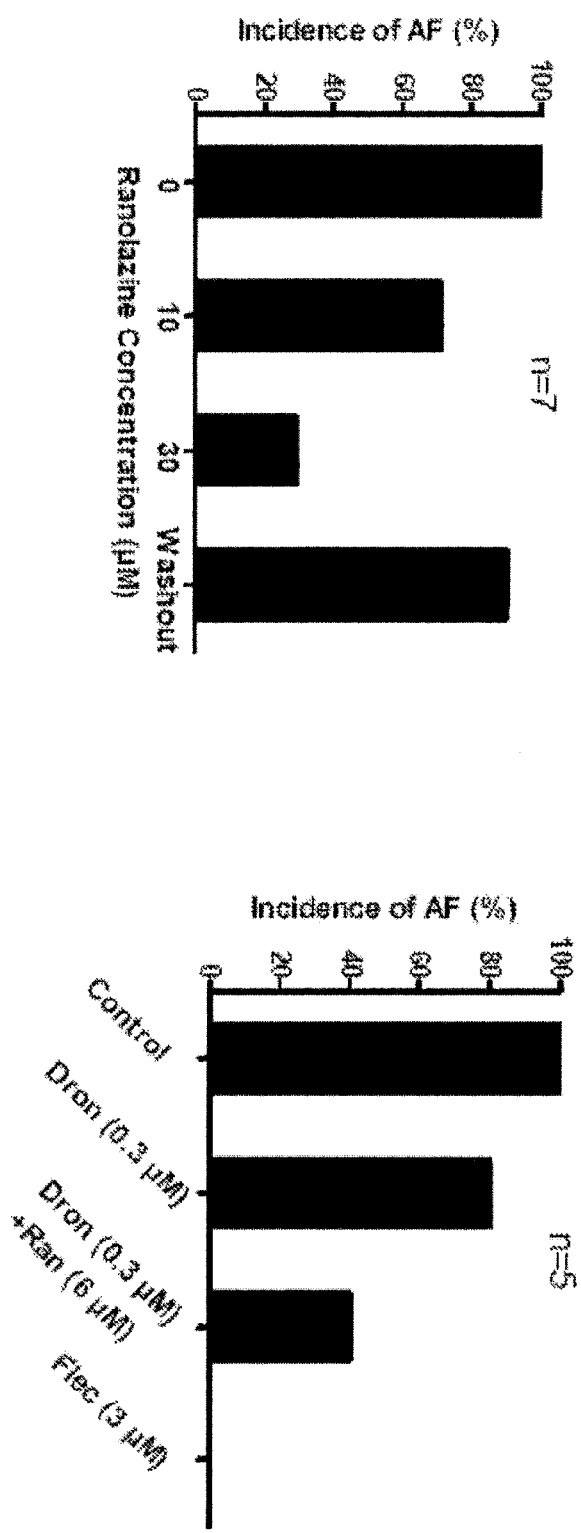
FIG. 21. Effects of ranolazine and dronedarone alone and in combination to reduce the incidence of electrically-induced atrial fibrillation (AF) in the presence of acetylcholine (ACh). A high concentration ranolazine (10-30 μM)

Effects of Ranolazine and Dronedarone Alone and in Combination on Atrial Fibrillation in the Rabbit Isolated Heart Treated with Acetylcholine Premature programmed atrial electrical stimulation (i.e., an S1S2 protocol) caused non-sustained atrial fibrillation (AF) in 12 out of 12 (100%) hearts exposed to acetylcholine (0.6-1 µM) (FIGS. 21, 22). Ranolazine alone decreased the inducibility of episodes of AF only at high concentrations of 10 and 30 µM (FIG. 21, left panel). Dronedarone (0.3 µM) alone abolished the inducible AF only in 1 out of 5 hearts (FIG. 21, right panel). In the presence of 0.3 µM dronedarone (FIG. 21, right panel), ranolazine (6 µM) further decreased the inducibility of AF to 40% (2 of 5 hearts) and reduced the duration of AF (FIG. 22). Flecainide (used here as a positive control known to terminate ACh-induced AF) abolished all episodes of AF in the presence of ACh in all 5 hearts studied (FIG. 21, right panel). The findings suggest that the combination of ranolazine and dronedarone was much more effective in preventing the action of acetylcholine to induce AF than was either drug alone. Because acetylcholine is the cardiac parasympathetic neurotransmitter, and because the acetylcholine-activated hyperpolarizing current $I_{KAch, Ado}$ is reportedly increased in atrial cells of patients with AF, the combination of dronedarone and ranolazine may be beneficial to reduce the incidence of AF in patients susceptible to the disease.

Effect of Dronedarone to Reduce Late Sodium Current (Late $I_{Na}$)

Ranolazine has been demonstrated to reduce late $I_{Na}$ in the heart, and this is accepted as the primary mechanism of its antianginal and anti-arrhythmic effects. The effect of dronedarone on late $I_{Na}$ has not been reported. Therefore we determined the effect of dronedarone on late $I_{Na}$ induced by incubation of HEK293 cells expressing the human heart sodium channel gene $Na_V1.5$ with the late $I_{Na}$ enhancer tefluthrin. Dronedarone reduced the tefluthrin-induced late $I_{Na}$ in a concentration-dependent manner (FIG. 23). The result indicates that dronedarone, like ranolazine, can reduce late $I_{Na}$. Thus, the combination of dronedarone and ranolazine may be anticipated to reduce late $I_{Na}$. A reduction of late $I_{Na}$ in the heart has been associated with a reduction of atrial arrhythmias in patients and in animal models of atrial fibrillation.

Effects of Ranolazine and Dronedarone Alone and in Combination to Reduce the Amplitude of Delayed After-Depolarizations (DADs) Induced by Isoproterenol (Iso)

The catecholamine and β-adrenergic receptor agonist isoproterenol is known to cause increases of L-type calcium channel current and late $Na^+$ current (late $I_{Na}$) that may lead to $Na^+$ and $Ca^{2+}$ overload in cardiac myocytes. A recognized pro-arrhythmic consequence of $Ca^{2+}$ overload is the propensity for occurrences of delayed after-depolarizations (DADs). DADs are known triggers of ectopic arrhythmic activity in the heart. Both dronedarone (FIG. 24) and ranolazine (FIG. 25) alone and in combination (FIG. 26) reduced the amplitude of isoproterenol (50 nM)-induced DADs in myocytes isolated from ventricles of guinea pig hearts. The effects of dronedarone (100 nM) and ranolazine (3 µM) were additive. Similarly, the effects of 30 nM dronedarone and 3 µM ranolazine were additive (not shown). The finding indicates that the combination of ranolazine and dronedarone may have a beneficial action to reduce one of the triggers of ectopic electrical activity (i.e., DADs) that leads to both atrial and ventricular arrhythmias. Because catecholamine-induced tachyarrhythmias are common in patients with heart failure and ischemic heart disease, the combination of ranolazine and dronedarone may reduce the incidence of arrhythmias in patients with these diseases.

REFERENCE LIST

1. Go A S, Hylek E M, Phillips K A, Chang Y, Henault L E, Selby J V, Singer D E. Prevalence of diagnosed atrial fibrillation in adults: national implications for rhythm management and stroke prevention: the AnTicoagulation and Risk Factors in Atrial Fibrillation (ATRIA) Study. *JAMA.* 2001; 285:2370-2375.
2. Zimetbaum P J. Dronedarone for atrial fibrillation—an odyssey. *N Engl J Med.* 2009; 360:1811-1813.
3. Piccini J P, Hasselblad V, Peterson E D, Washam J B, Califf R M, Kong D F. Comparative efficacy of dronedarone and amiodarone for the maintenance of sinus rhythm in patients with atrial fibrillation. *J Am Coll Cardiol.* 2009; 54:1089-1095.
4. Touboul P, Brugada J, Capucci A, Crijns H J, Edvardsson N, Hohnloser S H. Dronedarone for prevention of atrial fibrillation: a dose-ranging study. *Eur Heart J.* 2003; 24:1481-1487.
5. Singh B N, Connolly S J, Crijns H J, Roy D, Kowey P R, Capucci A, Radzik D, Aliot E M, Hohnloser S H. Dronedarone for maintenance of sinus rhythm in atrial fibrillation or flutter. *N Engl J Med.* 2007; 357:987-999.
6. Davy J M, Herold M, Hoglund C, Timmermans A, Alings A, Radzik D, Van K L. Dronedarone for the control of ventricular rate in permanent atrial fibrillation: the Efficacy and safety of dRonedArone for the cOntrol of ventricular rate during atrial fibrillation (ERATO) study. *Am Heart J.* 2008; 156:527.e1-527.e9.
7. Kober L, Torp-Pedersen C, McMurray J J, Gotzsche O, Levy S, Crijns H, Amlie J, Carlsen J. Increased mortality after dronedarone therapy for severe heart failure. *N Engl J Med.* 2008; 358:2678-2687.
8. Hohnloser S H, Crijns H J, van E M, Gaudin C, Page R L, Torp-Pedersen C, Connolly S J. Effect of dronedarone on cardiovascular events in atrial fibrillation. *N Engl J Med.* 2009; 360:668-678.
9. Burashnikov A, Di Diego J M, Zygmunt A C, Belardinelli L, Antzelevitch C. Atrium-selective sodium channel block as a strategy for suppression of atrial fibrillation: differences in sodium channel inactivation between atria and ventricles and the role of ranolazine. *Circulation.* 2007; 116:1449-1457.
10. Burashnikov A, Di Diego J M, Sicouri S, Ferreiro M, Carlsson L, Antzelevitch C. Atrial-selective effects of chronic amiodarone in the management of atrial fibrillation. *Heart Rhythm.* 2008; 5:1735-1742.
11. Sicouri S, Glass A, Belardinelli L, Antzelevitch C. Antiarrhythmic effects of ranolazine in canine pulmonary vein sleeve preparations. *Heart Rhythm.* 2008; 5:1019-1026.
12. Sicouri S, Belardinelli L, Carlsson L, Antzelevitch C. Potent antiarrhythmic effects of chronic amiodarone in canine pulmonary vein sleeve preparations. *J Cardiovasc Electrophysiol.* 2009; 20:803-810.
13. Kumar K, Nearing B D, Carvas M, Nascimento B C, Acar M, Belardinelli L, Verrier R L. Ranolazine exerts potent effects on atrial electrical properties and abbreviates atrial fibrillation duration in the intact porcine heart. *J Cardiovasc Electrophysiol.* 2009; 20:796-802.
14. Sicouri S, Burashnikov A, Belardinelli L, Antzelevitch C. Synergistic electrophysiologic and antiarrhythmic effects of the combination of ranolazine and chronic amiodarone in canine atria. Circ Arrhythm Electrophysiol. In press 2009.
15. Antzelevitch C, Belardinelli L, Zygmunt A C, Burashnikov A, Di Diego J M, Fish J M, Cordeiro J M, Thomas G P. Electrophysiologic effects of ranolazine: a novel anti-anginal agent with antiarrhythmic properties. *Circulation.* 2004; 110:904-910.
16. Burashnikov A, Mannava S, Antzelevitch C. Transmembrane action potential heterogeneity in the canine isolated arterially-perfused atrium: effect of $I_{Kr}$ and $I_{to}/I_{Kur}$ block. *Am J Physiol.* 2004; 286:H2393-H2400.
17. Patterson E, Po S S, Scherlag B J, Lazzara R. Triggered firing in pulmonary veins initiated by in vitro autonomic nerve stimulation. *Heart Rhythm.* 2005; 2:624-631.
18. Patterson E, Lazzara R, Szabo B, Liu H, Tang D, Li Y H, Scherlag B J, Po S S. Sodium-calcium exchange initiated by the Ca2+ transient: an arrhythmia trigger within pulmonary veins. *J Am Coll Cardiol.* 2006; 47:1196-1206.
19. Chen Y J, Chen S A, Chang M S, Lin C I. Arrhythmogenic activity of cardiac muscle in pulmonary veins of the dog: implication for the genesis of atrial fibrillation. *Cardiovasc Res.* 2000; 48:265-273.
20. Chen Y J, Chen S A. Electrophysiology of pulmonary veins. *J Cardiovasc Electrophysiol.* 2006; 17:220-224.
21. Fuster V, Ryden L E, Cannom D S, Crijns H J, Curtis A B, Ellenbogen K A, Halperin J L, Le Heuzey J Y, Kay G N, Lowe J E, Olsson S B, Prystowsky E N, Tamargo J L, Wann S, Smith S C, Jr., Jacobs A K, Adams C D, Anderson J L, Antman E M, Hunt S A, Nishimura R, Ornato J P, Page R L, Riegel B, Priori S G, Blanc J J, Budaj A, Camm A J, Dean V, Deckers J W, Despres C, Dickstein K, Lekakis J, McGregor K, Metra M, Morais J, Osterspey A, Zamorano J L. ACC/AHA/ESC 2006 guidelines for the management of patients with atrial fibrillation—executive summary: a report of the American College of Cardiology/American Heart Association Task Force on Practice Guidelines and the European Society of Cardiology Committee for Practice Guidelines (Writing Committee to Revise the 2001 Guidelines for the Management of Patients With Atrial Fibrillation). *J Am Coll Cardiol.* 2006; 48:854-906.
22. Reiffel, J. A. Rate versus rhythm control pharmacotherapy for atrial fibrillation: where are we in 2008?<[11] Journal>. 2008; 1:31-47.
23. Naccarelli G V, Gonzalez M D. Atrial fibrillation and the expanding role of catheter ablation: do antiarrhythmic drugs have a future? *J Cardiovasc Pharmacol.* 2008; 52:203-209.
24. Cain M E, Curtis A B. Rhythm control in atrial fibrillation—one setback after another. *N Engl J Med.* 2008; 358: 2725-2727.
25. Savelieva I, Camm J. Anti-arrhythmic drug therapy for atrial fibrillation: current anti-arrhythmic drugs, investigational agents, and innovative approaches. *Europace.* 2008; 10:647-665.
26. Haissaguerre M, Jais P, Shah D C, Takahashi A, Hocini M, Quiniou G, Garrigue S, Le Mouroux A, Le Metayer P, Clementy J. Spontaneous initiation of atrial fibrillation by ectopic beats originating in the pulmonary veins. *N Engl J Med.* 1998; 339:659-666.
27. Shah D C, Haissaguerre M, Jais P, Clementy J. High-resolution mapping of tachycardia originating from the superior vena cava: evidence of electrical heterogeneity, slow conduction, and possible circus movement reentry. *J Cardiovasc Electrophysiol.* 2002; 13:388-392.
28. Nattel S, Shiroshita-Takeshita A, Brundel B J, Rivard L. Mechanisms of atrial fibrillation: lessons from animal models. *Prog Cardiovasc Dis.* 2005; 48:9-28.
29. Antzelevitch C, Burashnikov A. Atrial-selective sodium channel block as a novel strategy for the management of atrial fibrillation. *J Electrocardiol.* 2009; 42:543-548.
30. Varro A, Takacs J, Nemeth M, Hala O, Virag L, Iost N, Balati B, Agoston M, Vereckei A, Pastor G, Delbruyere M, Gautier P, Nisato D, Papp J G. Electrophysiological effects of dronedarone (SR 33589), a noniodinated amiodarone derivative in the canine heart: comparison with amiodarone. *Br J Pharmacol.* 2001; 133:625-634.
31. Gautier P, Guillemare E, Marion A, Bertrand J P, Tourneur Y, Nisato D. Electrophysiologic characterization of dronedarone in guinea pig ventricular cells. *J Cardiovasc Pharmacol.* 2003; 41:191-202.
32. Sun W, Sarma J S, Singh B N. Electrophysiological effects of dronedarone (SR33589), a noniodinated benzofuran derivative, in the rabbit heart: comparison with amiodarone. *Circulation.* 1999; 100:2276-2281.
33. Sun W, Sarma J S, Singh B N. Chronic and acute effects of dronedarone on the action potential of rabbit atrial muscle preparations: comparison with amiodarone. *J Cardiovasc Pharmacol.* 2002; 39:677-684.
34. Moro S, Ferreiro M, Celestino D, Medei E, Elizari M V, Sicouri S. In vitro effects of acute amiodarone and dronedarone on epicardial, endocardial, and M cells of the canine ventricle. *J Cardiovasc Pharmacol Ther.* 2007; 12:314-321.
35. Manning A, Thisse V, Hodeige D, Richard J, Heyndrickx J P, Chatelain P. SR 33589, a new amiodarone-like antiarrhythmic agent: electrophysiological effects in anesthetized dogs. *J Cardiovasc Pharmacol.* 1995; 25:252-261.
36. Verduyn S C, Vos M A, Leunissen H D, van Opstal J M, Wellens H J. Evaluation of the acute electrophysiologic effects of intravenous dronedarone, an amiodarone-like agent, with special emphasis on ventricular repolarization and acquired torsade de pointes arrhythmias. *J Cardiovasc Pharmacol.* 1999; 33:212-222.
37. Finance O, Manning A, Chatelain P. Effects of a new amiodarone-like agent, SR 33589, in comparison to amiodarone, D,L-sotalol, and lignocaine, on ischemia-induced ventricular arrhythmias in anesthetized pigs. *J Cardiovasc Pharmacol.* 1995; 26:570-576.
38. Singh B N. Amiodarone as paradigm for developing new drugs for atrial fibrillation. *J Cardiovasc Pharmacol.* 2008; 52:300-305.
39. Scirica B M, Morrow D A, Hod H, Murphy S A, Belardinelli L, Hedgepeth C M, Molhoek P, Verheugt F W, Gersh B J, McCabe C H, Braunwald E. Effect of ranolazine, an antianginal agent with novel electrophysiological properties, on the incidence of arrhythmias in patients with non ST-segment elevation acute coronary syndrome: results from the Metabolic Efficiency With Ranolazine for Less Ischemia in Non ST-Elevation Acute Coronary Syndrome Thrombolysis in Myocardial Infarction 36 (MERLIN-TIMI 36) randomized controlled trial. *Circulation.* 2007; 116:1647-1652.
40. Murdock D K, Overton N, Kersten M, Kaliebe J, Devecchi F. The effect of ranolazine on maintaining sinus rhythm in patients with resistant atrial fibrillation. *Indian Pacing Electrophysiol J.* 2008; 8:175-181.
41. Murdock D K, Kersten M, Kaliebe J, Larrian G. The use of oral ranolazine to convert new or paroxysmal atrial fibrillation: a reveiw of experience with implications for possible "pill in the pocket" approach to atrial fibrillation. *Indian Pacing Electrophysiol J.* 2009; 9:260-267.
42. Goldschlager N, Epstein A E, Naccarelli G V, Olshansky B, Singh B, Collard H R, Murphy E. A practical guide for clinicians who treat patients with amiodarone: 2007. *Heart Rhythm.* 2007; 4:1250-1259.
43. Bardy G H, Lee K L, Mark D B, Poole J E, Packer D L, Boineau R, Domanski M, Troutman C, Anderson J, Johnson G, McNulty S E, Clapp-Channing N, vidson-Ray L D, Fraulo E S, Fishbein D P, Luceri R M, Ip J H. Amiodarone or an implantable cardioverter-defibrillator for congestive heart failure. *N Engl J Med.* 2005; 352:225-237.
44. Connolly S J, Crijns H J, Torp-Pedersen C, van E M, Gaudin C, Page R L, Hohnloser S H. Analysis of stroke in ATHENA: a placebo-controlled, double-blind, parallel-arm trial to assess the efficacy of dronedarone 400 mg BID for the prevention of cardiovascular hospitalization or death from any cause in patients with atrial fibrillation/atrial flutter. *Circulation.* 2009; 120:1174-1180.
45. Koren M J, Crager M R, Sweeney M. Long-term safety of a novel antianginal agent in patients with severe chronic stable angina: the Ranolazine Open Label Experience (ROLE). *J Am Coll Cardiol.* 2007; 49:1027-1034.
46. Chaitman B R. Ranolazine for the treatment of chronic angina and potential use in other cardiovascular conditions. *Circulation.* 2006; 113:2462-2472.
47. Maltsev V A, Sabbah H N, Undrovinas A I. Late sodium current is a novel target for amiodarone: studies in failing human myocardium. *J Mol Cell Cardiol.* 2001; 33:923-932.
48. Antzelevitch C. Electrical heterogeneity, cardiac arrhythmias, and the sodium channel. *Circ Res.* 2000; 87:964-965.
49. Antzelevitch C, Belardinelli L, Wu L, Fraser H, Zygmunt A C, Burashnikov A, Di Diego J M, Fish J M, Cordeiro J M, Goodrow R J, Scornik F S, Perez G J. Electrophysiologic properties and antiarrhythmic actions of a novel anti-anginal agent. *J Cardiovasc Pharmacol Therapeut.* 2004; 9 Suppl 1:S65-S83.
50. Shryock J C, Belardinelli L. Inhibition of late sodium current to reduce electrical and mechanical dysfunction of ischaemic myocardium. *Br J Pharmacol.* 2008; 153:1128-1132.
51. Burashnikov A, Antzelevitch C. Atrial-selective sodium channel block for the treatment of atrial fibrillation. *Expert Opin Emerg Drugs.* 2009; 14:233-249.
52. Pappone C, Santinelli V, Manguso F, Vicedomini G, Gugliotta F, Augello G, Mazzone P, Tortoriello V, Landoni G, Zangrillo A, Lang C, Tomita T, Mesas C, Mastella E, Alfieri O. Pulmonary vein denervation enhances long-term benefit after circumferential ablation for paroxysmal atrial fibrillation. *Circulation.* 2004; 109:327-334.

We claim:
1. A pharmaceutical formulation comprising dronedarone or a pharmaceutically acceptable salt thereof, ranolazine, and a pharmaceutically acceptable carrier or diluent.
2. The formulation of claim 1, formulated for intravenous administration.
3. The formulation of claim 2, formulated for oral administration.
4. The formulation of claim 3, wherein the formulation is in tablet form.
5. The formulation of claim 4, wherein the tablet comprises from about 10 mg to about of 800 mg of dronedarone or a pharmaceutically acceptable salt thereof.
6. The formulation of claim 5, wherein the tablet comprises from about 25 mg to about 600 mg of dronedarone or a pharmaceutically acceptable salt thereof.
7. The formulation of claim 6, wherein the tablet comprises from about 25 mg to about 400 mg of dronedarone or a pharmaceutically acceptable salt thereof.
8. The formulation of claim 7, wherein the tablet comprises from about 50 mg to about 200 mg of dronedarone or a pharmaceutically acceptable salt thereof.
9. The formulation of claim 4, wherein the tablet comprises from about 50 mg to about 1000 mg of ranolazine.
10. The formulation of claim 9, wherein the tablet comprises from about 100 mg to about 750 mg of ranolazine.
11. The formulation of claim 10, wherein the tablet comprises from about 150 mg to about 375 mg of ranolazine.
12. The formulation of claim 4, wherein the ranolazine is formulated for sustained release.
13. The formulation of claim 4, wherein the salt of dronedarone is a phosphoric acid addition salt.
14. The formulation of claim 4, wherein the tablet comprises a first layer comprising dronedarone or a pharmaceutically acceptable salt thereof and a second layer comprising ranolazine formulated for sustained release.
15. A method for treating or preventing atrial fibrillation or atrial flutter in a human patient in need thereof, comprising administering to the patient an effective amount of the formulation of claim 1.
16. A method for modulating ventricular or atrial rate in a human patient in need thereof, comprising administering to the patient an effective amount of the formulation of claim 1.
17. A bilayer tablet comprising a first layer comprising a phosphoric acid addition salt of dronedarone and a second layer comprising ranolazine formulated for sustained release.
18. The tablet of claim 17, comprising from about 10 mg to about 800 mg of phosphoric acid addition salt of dronedarone.
19. The tablet of claim 17, comprising from about 25 mg to about 600 mg of phosphoric acid addition salt of dronedarone.
20. The tablet of claim 17, comprising from about 25 mg to about 400 mg of phosphoric acid addition salt of dronedarone.
21. The tablet of claim 17, comprising from about 50 mg to about 200 mg of phosphoric acid addition salt of dronedarone.
22. The tablet of claim 17, comprising from about 50 mg to about 1000 mg of ranolazine.
23. The tablet of claim 17, comprising from about 100 mg to about 750 mg of ranolazine.
24. The table of claim 17, further comprising a pharmaceutically acceptable diluent or carrier.

* * * * *